United States Patent
Jantz et al.

(10) Patent No.: US 10,662,440 B2
(45) Date of Patent: May 26, 2020

(54) SELF-LIMITING VIRAL VECTORS ENCODING NUCLEASES

(71) Applicants: Precision BioSciences, Inc., Durham, NC (US); Derek Jantz, Durham, NC (US); James Jefferson Smith, Morrisville, NC (US); Michael G. Nicholson, Chapel Hill, NC (US)

(72) Inventors: Derek Jantz, Durham, NC (US); James Jefferson Smith, Morrisville, NC (US); Michael G. Nicholson, Chapel Hill, NC (US)

(73) Assignee: Precision BioSciences, Inc., Durham, NC (US)

( * ) Notice: Subject to any disclaimer, the term of this patent is extended or adjusted under 35 U.S.C. 154(b) by 0 days.

(21) Appl. No.: 15/737,918

(22) PCT Filed: Jun. 20, 2016

(86) PCT No.: PCT/US2016/038434
§ 371 (c)(1),
(2) Date: Dec. 19, 2017

(87) PCT Pub. No.: WO2016/205825
PCT Pub. Date: Dec. 22, 2016

(65) Prior Publication Data
US 2018/0171357 A1 Jun. 21, 2018

Related U.S. Application Data

(60) Provisional application No. 62/182,186, filed on Jun. 19, 2015.

(51) Int. Cl.
| | | |
|---|---|---|
| *C12N 15/63* | (2006.01) | |
| *C12N 15/85* | (2006.01) | |
| *C07H 21/04* | (2006.01) | |
| *C12N 15/86* | (2006.01) | |
| *C12N 9/22* | (2006.01) | |
| *A61K 38/00* | (2006.01) | |

(52) U.S. Cl.
CPC .............. *C12N 15/86* (2013.01); *C12N 9/22* (2013.01); *A61K 38/00* (2013.01); *C12N 15/63* (2013.01); *C12N 2740/10041* (2013.01); *C12N 2750/14041* (2013.01); *C12N 2750/14143* (2013.01); *C12N 2830/008* (2013.01); *C12N 2830/42* (2013.01)

(58) Field of Classification Search
CPC .............. C12N 15/63; C12N 15/86; C12N 2740/10041; C12N 2750/14041; C12N 2750/14143; C12N 2830/42; C07H 21/04
USPC ............ 435/320.1, 455; 536/23.1, 23.2, 24.1
See application file for complete search history.

(56) References Cited

U.S. PATENT DOCUMENTS

2013/0023033 A1   1/2013   Wilson et al.

FOREIGN PATENT DOCUMENTS

| EP | 2788489 A1 | 6/2013 |
| WO | WO 2007/047859 A2 | 4/2007 |
| WO | WO 2009/059195 A2 | 5/2009 |
| WO | WO 2015/089351 A1 | 6/2015 |
| WO | WO 2016/186772 A2 | 11/2016 |
| WO | WO 2016/205728 A1 | 12/2016 |
| WO | WO 2017/136335 A1 | 8/2017 |

OTHER PUBLICATIONS

Smith et al., 2018, US 20180344817 A1, effective filing date, May 1, 2015.*
Beetham et al., 2016, US 20160289691 A1, effective filing date, Mar. 15, 2013.*
PCT/US2016/038434, Sep. 16, 2016, International Search Report and Written Opinion.
PCT/US2016/038434, Dec. 28, 2017, International Preliminary Report on Patentability.
International Search Report and Written Opinion for Application No. PCT/US2016/038434 dated Sep. 16, 2016.
International Preliminary Report on Patentability for Application. No. PCT/US2016/038434 dated Dec. 28, 2017.
Arnould et al., Engineering of large numbers of highly specific homing endonucleases that induce recombination on novel DNA targets. J Mol Biol. Jan. 20, 2006;355(3):443-58. Epub Nov. 15, 2005.
Beurdeley et al., Compact designer TALENs for efficient genome engineering. Nat Commun. 2013;4:1762. doi: 10.1038/ncomms2782.
Carter, Adeno-Associated Virus and Adeno-Associated Virus Vectors for Gene Delivery. DD Lassie & N Smyth Templeton. Gene Therapy: Therapeutic Mechanisms and Strategies. 2000:41-59.
Chames et al, In vivo selection of engineered homing endonucleases using double-strand break induced homologous recombination. Nucleic Acids Res. Nov. 23, 2005;33(20):e178.

(Continued)

*Primary Examiner* — Shin Lin Chen
(74) *Attorney, Agent, or Firm* — Wolf, Greenfield & Sacks, P.C.

(57) ABSTRACT

Disclosed herein are viral vectors for use in recombinant molecular biology techniques. In particular, the present disclosure relates to self-limiting viral vectors comprising genes encoding site-specific endonucleases as well as recognition sequences for site-specific endonucleases such that expression of the endonuclease in a cell cleaves the viral vector and limits its persistence time. In some embodiments, the viral vectors disclosed herein also carry directives to delete, insert, or change a target sequence.

21 Claims, 15 Drawing Sheets
Specification includes a Sequence Listing.

(56) References Cited

OTHER PUBLICATIONS

Chevalier et al., Homing endonucleases: structural and functional insight into the catalysts of intron/intein mobility. Nucleic Acids Res. Sep. 15, 2001;29(18):3757-74.
Daya et al., Gene therapy using adeno-associated virus vectors. Clin Microbiol Rev. Oct. 2008;21(4):583-93. doi: 10.1128/CMR.00008-08.
Deyle et al., Adeno-associated virus vector integration. Curr Opin Mol Ther. Aug. 2009;11(4):442-7. Author manuscript.
Durai et al., Zinc finger nucleases: custom-designed molecular scissors for genome engineering of plant and mammalian cells. Nucleic Acids Res. Oct. 26, 2005;33(18):5978-90. Print 2005.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013. Author manuscript.
Gao et al., Exploiting natural diversity of AAV for the design of vectors with novel properties. Methods Mol Biol. 2011;807:93-118. doi: 10.1007/978-1-61779-370-7_4.
Grieger et al., Adeno-associated virus as a gene therapy vector: vector development, production and clinical applications. Adv Biochem Eng Biotechnol. 2005;99:119-45.
Grizot et al., Efficient targeting of a SCID gene by an engineered single-chain homing endonuclease. Nucleic Acids Res. Sep. 2009;37(16):5405-19. doi: 10.1093/nar/gkp548. Epub Jul. 7, 2009.
Kyöstiö et al., Analysis of adeno-associated virus (AAV) wild-type and mutant Rep proteins for their abilities to negatively regulate AAV p5 and p19 mRNA levels. J Virol. May 1994;68(5):2947-57.
Li et al., Generation of single-chain LAGLIDADG homing endonucleases from native homodimeric precursor proteins. Nucleic Acids Res. Apr. 2009;37(5):1650-62. doi: 10.1093/nar/gkp004. Epub Jan. 19, 2009.
Maguire et al., Safety and efficacy of gene transfer for Leber's congenital amaurosis. N Engl J Med. May 22, 2008;358(21):2240-8. doi: 10.1056/NEJMoa0802315. Epub Apr. 27, 2008. Author manuscript.
Mak et al., TAL effectors: function, structure, engineering and applications. Curr Opin Struct Biol. Feb. 2013;23(1):93-9. doi: 10.1016/j.sbi.2012.11.001. Epub Dec. 22, 2012. Author manuscript.
Mali et al., Cas9 as a versatile tool for engineering biology. Nat Methods. Oct. 2013;10(10):957-63. doi: 10.1038/nmeth.2649. Author manuscript.
Matsushita et al., Adeno-associated virus vectors can be efficiently produced without helper virus. Gene Ther. Jul. 1998;5(7):938-45.
McCarty et al., Self-complementary recombinant adeno-associated virus (scAAV) vectors promote efficient transduction independently of DNA synthesis. Gene Ther. Aug. 2001;8(16):1248-54.
Mitchell et al., AAV's anatomy: roadmap for optimizing vectors for translational success. Curr Gene Ther. Oct. 2010;10(5):319-340. Author manuscript.
Muralidhar et al., Site-directed mutagenesis of adeno-associated virus type 2 structural protein initiation codons: effects on regulation of synthesis and biological activity. J Virol. Jan. 1994;68(1):170-6.
Nony et al., Novel cis-acting replication element in the adeno-associated virus type 2 genome is involved in amplification of integrated rep-cap sequences. J Virol. Oct. 2001;75(20):9991-4.
Rabinowitz et al., Building a better vector: the manipulation of AAV virions. Virology. Dec. 20, 2000;278(2):301-8.
Ran et al., Genome engineering using the CRISPR-Cas9 system. Protoc. Nov. 2013;8(11):2281-2308. doi: 10.1038/nprot.2013.143. Epub Oct. 24, 2013. Author manuscript.
Seligman et al., Mutations altering the cleavage specificity of a homing endonuclease. Nucleic Acids Res. Sep. 1, 2002;30(17):3870-9.
Stoddard, Homing endonuclease structure and function. Q Rev Biophys. Feb. 2005;38(1):49-95. Epub Dec. 9, 2005.
Sussman et al., Isolation and characterization of new homing endonuclease specificities at individual target site positions. J Mol Biol. Sep. 3, 2004;342(1):31-41.
Warrington et al., Adeno-associated virus type 2 VP2 capsid protein is nonessential and can tolerate large peptide insertions at its N terminus. J Virol. Jun. 2004;78(12):6595-609.
Xie et al., The atomic structure of adeno-associated virus (AAV-2), a vector for human gene therapy. Proc Natl Acad Sci USA. Aug. 6, 2002;99(16):10405-10. Epub Jul. 22, 2002.
Extended European Search Report for Application No. EP 16812645.6 dated Oct. 25, 2018.
Cox et al., Therapeutic genome editing: prospects and challenges. Nat Med. Feb. 2015;21(2):121-31. doi: 10.1038/nm.3793.
Epstein et al., 119. Engineering a Self-Inactivating CRISPR System for AAV Vectors. Mol Ther. May 2016;24(S1):S50.
Gürlevik et al., Meganuclease-mediated virus self-cleavage facilitates tumor-specific virus replication. Mol Ther. Sep. 2013;21(9):1738-48. doi: 10.1038/mt.2013.117. Epub Jun. 11, 2013.
Rivière et al., Variable correction of Artemis deficiency by I-Sce1-meganuclease-assisted homologous recombination in murine hematopoietic stem cells. Gene Ther. May 2014;21(5):529-32. doi: 10.1038/gt.2014.20. Epub Mar. 13, 2014.

* cited by examiner

SELF-LIMITING VIRAL VECTORS ENCODING NUCLEASES

CROSS REFERENCE TO RELATED APPLICATIONS

This application is a national stage filing under 35 U.S.C. § 371 of international application number PCT/US2016/038434, filed Jun. 20, 2016, which was published under PCT Article 21(2) in English and claims the benefit under 35 U.S.C. § 119(e) of U.S. provisional application Ser. No. 62/182,186, filed Jun. 19, 2015, each of which is herein incorporated by reference in its entirety.

FIELD OF THE INVENTION

The invention relates to the field of molecular biology and recombinant nucleic acid technology. In particular, the invention relates to self-limiting viral vectors comprising genes encoding site-specific endonucleases as well as recognition sequences for site-specific endonucleases such that expression of the endonuclease in a cell cleaves the viral vector and limits its persistence time. Such viral vectors may also carry directives to delete, insert, or change a target sequence. Moreover the self-limiting viral vectors may be engineered to address kinetic balancing (i.e., ensuring adequate expression of the endonuclease before that endonuclease finds its recognition sequence within the viral vector).

BACKGROUND OF THE INVENTION

AAV. Adeno-associated virus (AAV) is a small virus, which infects humans and several other primate species. AAV is not known to cause disease, and generally causes only a mild immune response. The virus infects both dividing and quiescent cells and can be engineered to persist in an extrachromosomal state without integrating into the genome of the host cell (Russel D W, Deyle D R (2010) *Current Opinion in Molecular Therapy.* 11: 442-447; Grieger J C, Samulski R J (2005) *Advances in Biochemical Engineering/Biotechnology* 99: 119-45P). These features make AAV a very attractive candidate for creating viral vectors for gene therapy. Recent human clinical trials using AAV for gene therapy in the retina have shown promise (Maguire A M, et al. (2008) *New England Journal of Medicine* 358: 2240-8). Moreover, AAV presents a well-known system with an established safety record with the completion of over sixty clinical trials. (Mitchell A M, Nicolson S C, Warischalk J K, and Samulski R J (2010) *Curr Gene Ther.* 10(5): 319-40).

Wild-type AAV has the ability to stably integrate into the host cell genome at a specific site (designated AAVS1) in the human chromosome 19. This feature makes it somewhat more predictable than other viral vectors such as retroviruses, which present the threat of random insertion and of mutagenesis. Gene therapy vectors based on AAV, however, generally eliminate this integrative capacity by removal of the rep and cap genes from the DNA of the vector. In their place, a gene of interest can be cloned under the control of a promoter between the viral inverted terminal repeats (ITRs) that aid in concatamer formation in the nucleus after the single-stranded vector DNA is converted by host cell DNA polymerase complexes into double-stranded DNA. AAV-based gene therapy vectors form episomal concatamers in the host cell nucleus. In non-dividing cells, these concatemers remain intact for the life of the host cell. In dividing cells, AAV DNA is lost through cell division, since the episomal DNA is not replicated along with the host cell DNA. Random integration of AAV DNA into the host genome is detectable but occurs at very low frequency.

AAV presents disadvantages as well. The cloning capacity of the vector is relatively limited and most therapeutic genes require the complete replacement of the virus's 4.7 kilobase genome. Large genes are, therefore, not suitable for use in a standard AAV vector. Options are currently being explored to overcome the limited coding capacity. The AAV ITRs of two genomes can anneal to form head to tail concatamers, almost doubling the capacity of the vector. Insertion of splice sites allows for the removal of the ITRs from the transcript, alleviating concatamer formation.

Because of AAV's specialized gene therapy advantages, researchers have created an altered version of AAV termed self-complementary adeno-associated virus (scAAV). Whereas AAV packages a single strand of DNA, and must wait for its second strand to be synthesized, scAAV packages two shorter strands that are complementary to each other. By avoiding second-strand synthesis, scAAV can express more quickly, but although as a caveat, scAAV can only encode half of the already limited capacity of AAV (McCarty D M, Monahan P E, Samulski R J (2001) *Gene Therapy* 8: 1248-54)

The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. The former is composed of four overlapping genes encoding Rep proteins required for the AAV life cycle, and the latter contains overlapping nucleotide sequences of capsid proteins: VP1, VP2 and VP3, which interact together to form a capsid of an icosahedral symmetry (Carter, B J (2000) In *DD Lassic & N Smyth Templeton. Gene Therapy: Therapeutic Mechanisms and Strategies.* New York City: Marcel Dekker, Inc. pp. 41-59).

The Inverted Terminal Repeat (ITR) sequences comprise approximately 145 bases each. The first 125 nucleotides of the ITR sequence are palindromic, folding in on itself to create a T-shaped hairpin structure (Daya, Shyam (2008) *Clin. Microbiol. Rev.* 21(4) 583-593). The other 20 bases of the ITR remain unpaired and are known as the D sequence. The origin of replication is the ITR and serves as a primer for second-strand synthesis.

With regard to gene therapy, ITRs seem to be the only sequences required in cis next to the therapeutic gene: structural (cap) and packaging (rep) proteins can be delivered in trans. With this assumption, many methods have been established for the efficient production of recombinant AAV (rAAV) vectors containing a reporter, or therapeutic gene. However, it was also published that the ITRs are not the only elements required in cis for effective replication and encapsidation. Some research groups have identified a sequence designated cis-acting Rep-dependent element (CARE) inside the coding sequence of the rep gene. CARE was shown to augment amplification, when present in cis (Nony P, Tessier J, Chadeuf G, et al. (2001) *Journal of Virology* 75: 9991-4).

On the "left side" of the genome, the rep genes are transcribed from two promoters, p5 and p19, from which two overlapping messenger ribonucleic acids (mRNAs) of different length can be produced. Each of these contains an intron, which may or may not be spliced out. Given these possibilities generated by such a system, four various mRNAs, and consequently, four various Rep proteins with overlapping sequence can be synthesized. Their names depict their sizes in kilodaltons (kDa): Rep78, Rep68, Rep52 and Rep40 (Kyostio S R, et al. (1994) *Journal of Virology* 68: 2947-57). Rep78 and 68 can specifically bind the hairpin formed by the ITR in the self-priming act and cleave at a specific region, designated terminal resolution site, within the hairpin. They were also shown to be necessary for the AAVS1-specific integration of the AAV genome. All four Rep proteins bind ATP and possess helicase activity. As demonstrated, Rep proteins upregulate the transcription from the p40 promoter (mentioned below), but downregulate both p5 and p19 promoters.

The "right side" of a positive-sensed AAV genome encodes overlapping sequences of three capsid proteins, VP1, VP2 and VP3, which start from one promoter, designated p40. The molecular weights of these proteins are 87,72 and 62 kiloDaltons, respectively. All three are translated from one mRNA, the unspliced transcript producing VP1. After this mRNA is synthesized, it can be spliced in two different manners: either a longer or shorter intron can be excised resulting in the formation of two pools of mRNAs: a 2.3 kb- and a 2.6 kb-long mRNA pool. Generally, especially in the presence of adenovirus, the longer intron is preferred, so the 2.3-kb-long mRNA represents the so-called "major splice." In this form, the first AUG codon that initiates synthesis of VP1 protein is cut out, resulting in a reduced overall level of VP1 protein synthesis. The first AUG codon that remains in the major splice is the initiation codon for VP3 protein. However, upstream of that codon in the same open reading frame lies an ACG sequence (encoding threonine, and serving as the initiation codon for VP2) surrounded by an optimal Kozak context. This contributes to a low level of synthesis of VP2 protein, which is actually VP3 protein with additional N terminal residues, as is VP1. Since the bigger intron is preferred to be spliced out, and since in the major splice the ACG codon is a much weaker translation initiation signal, the ratio at which the AAV structural proteins are synthesized in vivo is about 1:1:20, which is the same as in the mature virus particle (Rabinowitz J E, Samulski R J (2000) Virology 278: 301-8).

The unique fragment at the N terminus of VP1 protein possesses phospholipase A2 (PLA2) activity, likely required for releasing the AAV particles from late endosomes. VP2 and VP3 are crucial for correct virion assembly (Muralidhar S, Becerra S P, Rose J A (1994), *Journal of Virology* 68: 170-6). More recently, however, Warrington et al. have shown VP2 to be not only unnecessary for the complete virus particle formation and an efficient infectivity, but that VP2 can tolerate large insertions in its N terminus (Warrington K H, et al. (2004), *Journal of Virology* 78: 6595-609). In contrast. VP1 shows no such tolerance, probably because of the presence of the PLA2 domain (Id.). The AAV capsid is composed of 60 capsid protein subunits, VP1, VP2, and VP3, that are arranged in an icosahedral symmetry in a ratio of 1:1:10, with an estimated size of 3.9 MegaDaltons. The crystal structure of the VP3 protein was determined by Xie, Bue, et al. (Xie Q, Bu W, Bhatia S, et al. (2002) *Proceedings of the National Academy of Sciences of the United States of America* 99: 10405-10)

Currently, 12 AAV serotypes and nearly 100 variants have been identified in human and nonhuman primate populations. (Gao G, Zhong L, Danos 0 (2011) *Methods Mol. Biol.* 807:93-118). Serotypes can infect cells from multiple diverse tissue types. Tissue specificity, as determined by the capsid serotype and pseudotyping of AAV vectors to alter their tropism range, will likely impact to their efficacy and use in therapy.

Serotype 2 (AAV2) has been the most extensively examined to date. AAV2 presents a natural tropism towards skeletal muscles, neurons, vascular smooth muscle cells, and hepatocytes. Three cell receptors have been described for AAV2: heparan sulfate proteoglycan (HSPG), aVβ35 integrin, and fibroblast growth factor receptor 1 (FGFR-1). The first functions as a primary receptor, while the latter two have a co-receptor activity and enable AAV to enter the cell by receptor-mediated endocytosis.

Although AAV2 is the most popular serotype in various AAV-based research, it has been shown that other serotypes can be more effective as gene delivery vectors. For instance AAV6 appears much better in infecting airway epithelial cells, AAV7 presents very high transduction rate of murine skeletal muscle cells (similarly to AAV1 and AAV5), AAV8 is superb in transducing hepatocytes, and AAV1 and 5 were shown to be very efficient in gene delivery to vascular endothelial cells. In the brain, most AAV serotypes show neuronal tropism, while AAV5 also transduces astrocytes. AAV6, a hybrid of AAV1 and AAV2, also shows lower immunogenicity than AAV2. Serotypes can differ with the respect to the receptors they are bound to. For example AAV4 and AAV5 transduction can be inhibited by soluble sialic acids (of different form for each of these serotypes), and AAV5 was shown to enter cells via the platelet-derived growth factor receptor. Currently, rAAV8 and rAAV9 show the most prominent features relevant to therapeutic use relative to all other serotypes and under undisturbed physiological conditions. (Gao, G, Zhong L, and Danos O (2011) *Methods Mol. Biol.* 807:93-118).

There are several steps in the AAV infection cycle, from infecting a cell to producing new infectious particles. These are:

1. attachment to the cell membrane
2. receptor-mediated endocytosis
3. endosomal trafficking
4. escape from the late endosome or lysosome
5. translocation to the nucleus
6. uncoating
7. formation of double-stranded DNA replicative form of the AAV genome
8. expression of rep genes
9. genome replication
10. expression of cap genes, synthesis of progeny ssDNA particles
11. assembly of complete virions, and
12. release from the infected cell.

These steps may differ depending on the host cell type, which, in part, contributes to the defined and quite limited native tropism of AAV. Replication of the virus can also, even in regards to the same cell type, be dependent on the cell's cycle phase at the time of infection.

The characteristic feature of the adeno-associated virus is a deficiency in replication and thus, its inability to multiply in unaffected cells. The first factor described as providing successful generation of new AAV particles was the adenovirus, from which the AAV name originated. It was then shown that AAV replication is facilitated by selected proteins derived from the adenovirus genome, by other viruses such as HSV, or by genotoxic agents, such as UV irradiation or hydroxyurea. The minimal set of the adenoviral genes required for efficient generation of progeny AAV particles were discovered by Matsushita, Ellinger et al. (Matsushita T, Elliger S, Elliger C, et al. (1998) *Gene Therapy* 5: 938-45). This discovery paved the way for new production methods of recombinant AAV, which do not require adenoviral co-infection of the AAV-producing cells. In the absence of helper virus or genotoxic factors, AAV DNA can either integrate into the host genome, or persist in episomal form. In the former case integration is mediated by Rep78 and Rep68 proteins and requires the presence of ITRs flanking the region being integrated. In mice, the AAV genome has been observed persisting for long periods in quiescent tissues, such as skeletal muscles, in episomal form (a circular head-to-tail conformation).

Engineered Site-Specific Endonucleases. The present invention relates to the use of rAAV vectors to deliver engineered, site-specific endonucleases. Site-specific, rare-cutting endonucleases can be used to "edit" the genomes of living cells or organisms by targeting a double-stranded DNA break to a specific site in the genome that is then repaired by the cell's DNA repair machinery. This process can often result in DNA repair errors that, if they occur in the coding sequence of a gene, can disrupt or frameshift the gene and thereby disable (knock-out) the gene. Alternatively, chromosomal DNA breaks are highly recombinigenic and, so, site-specific endonucleases can be used to promote homologous recombination between the chromosomal DNA sequence and a transgenic sequence provided to the cell. This can result in, for example, the targeted insertion of a transgene or the repair of a mutant gene that is responsible for disease.

Methods for producing engineered, site-specific endonucleases are known in the art. For example, zinc-finger nucleases (ZFNs) can be engineered to recognize and cut pre-determined sites in a genome. ZFNs are chimeric proteins comprising a zinc finger DNA-binding domain fused to the nuclease domain of the FokI restriction enzyme. The zinc finger domain can be redesigned through rational or experimental means to produce a protein which binds to a pre-determined DNA sequence ~18 basepairs in length. By fusing this engineered protein domain to the FokI nuclease, it is possible to target DNA breaks with genome-level specificity. ZFNs have been used extensively to target gene addition, removal, and substitution in a wide range of eukaryotic organisms (reviewed in Durai S, et al. (2005) *Nucleic Acids Res* 33, 5978).

Likewise, TAL-effector nucleases (TALENs) can be generated to cleave specific sites in genomic DNA. Like a ZFN, a TALEN comprises an engineered, site-specific DNA-binding domain fused to the FokI nuclease domain (reviewed in Mak, et al. (2013) *Curr Opin Struct Biol.* 23:93-9). In this case, however, the DNA binding domain comprises a tandem array of TAL-effector domains, each of which specifically recognizes a single DNA basepair. The large size of a TALEN makes it difficult to package in rAAV, limiting the utility of TALENs for compositions of the present invention comprising rAAV vectors. Thus, vectors created using lentiviruses and/or retroviruses present an attractive candidate when using ZFNs and TALENs.

Compact TALENs are an alternative endonuclease architecture that avoids the need for dimerization (Beurdeley, et al. (2013) *Nat Commun.* 4:1762). A Compact TALEN comprises an engineered, site-specific TAL-effector DNA-binding domain fused to the nuclease domain from the I-TevI homing endonuclease. Unlike FokI, I-Teel does not need to dimerize to produce a double-strand DNA break so a Compact TALEN is functional as a monomer. Thus, it is possible to co-express two Compact TALENs in the same cell. Moreover, the Compact TALEN is smaller in size, making it much more attractive in vector design. (Id.).

Engineered endonucleases based on the CRISPR/Cas9 system are also known in the art (Ran, et al. (2013) *Nat Protoc.* 8:2281-2308; Mali et al. (2013) *Nat Methods.* 10:957-63). A CRISPR endonuclease comprises two components: (1) a caspase effector nuclease, typically microbial Cas9; and (2) a short "guide RNA" comprising a ~20 nucleotide targeting sequence that directs the nuclease to a location of interest in the genome. By expressing multiple guide RNAs in the same cell, each having a different targeting sequence, it is possible to target DNA breaks simultaneously to multiple sites in in the genome. The primary drawback of the CRISPR/Cas9 system is its reported high frequency of off-target DNA breaks, which could limit the utility of the system for treating human patients (Fu, et al. (2013) *Nat Biotechnol.* 31:822-6).

In the preferred embodiment of the invention, the DNA break-inducing agent is an engineered homing endonuclease (also called a "meganuclease"). Homing endonucleases are a group of naturally-occurring nucleases, which recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006) *Q. Rev. Biophys.* 38: 49-95).

Homing endonucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif (see Chevalier et al. (2001) *Nucleic Acids Res.* 29(18): 3757-3774). The LAGLIDADG homing endonucleases with a single copy of the LAGLIDADG motif form homodimers, whereas members with two copies of the LAGLIDADG motif are found as monomers.

I-CreI (SEQ ID NO: 1) is a member of the LAGLIDADG family of homing endonucleases, which recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004) *J Mol. Biol.* 342: 31-41; Chames et al. (2005) *Nucleic Acids Res.* 33: e178; Seligman et al. (2002) *Nucleic Acids Res.* 30: 3870-9; Arnould et al. (2006) *J Mol. Biol.* 355: 443-58). More recently, a method of rationally-designing mono-LAGLIDADG homing endonucleases capable of comprehensively redesigning I-CreI and other homing endonucleases to target widely-divergent DNA sites, including sites in mammalian, yeast, plant, bacterial, and viral genomes has been described (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li, et al. (2009) *Nucleic Acids Res.* 37:1650-62; Grizot, et al. (2009) *Nucleic Acids Res.* 37:5405-19.) Thus, a functional "single-chain" meganuclease can be expressed from a single transcript. By delivering genes encoding two different single-chain meganucleases to the same cell, it is possible to simultaneously cut two different sites. This, coupled with the extremely low frequency of off-target cutting observed with engineered meganucleases, makes them the preferred endonuclease for the present invention.

For many applications, it is necessary to deliver (a) gene(s) encoding engineered endonuclease(s) to the target cell or organism. For in vivo applications, rAAV is a preferred delivery vector. However, rAAV vectors have long persistence times in many cell types, particularly non-dividing cells. Such persistence can activate immune response within the cell and cause disruption. Genome editing using engineered endonucleases requires only a short burst of endonuclease expression such that the endonuclease protein accumulates to a sufficient intracellular concentration to cut its recognition sequence in the genome. Long-term expression of an endonuclease can result in unintended off-target DNA cutting or in an immune response directed toward cells expressing the foreign nuclease protein. Thus, there is a need for rAAV vectors encoding site-specific gene editing endonucleases in which the persistence time of the vector is limited.

SUMMARY OF THE INVENTION

The present invention is a self-limiting rAAV vector having limited persistence time in a cell or organism due to the presence of a recognition sequence for a site-specific endonuclease within the vector. Thus, in one embodiment, the invention provides a general method for limiting the persistence time of a vector. In another embodiment, the invention provides self-limiting viral vectors with reduced persistence time. In a third embodiment, the invention provides methods for using self-limiting viral vectors for genome editing applications.

It is understood that any of the embodiments described below can be combined in any desired way, and any embodiment or combination of embodiments can be applied to each of the aspects described below, unless the context indicates otherwise.

In some embodiments, the self-limiting viral vector is an adeno-associated virus (AAV) engineered to provide coding for a promoter, an endonuclease, and an endonuclease recognition site within the ITRs. The self-limiting viral vector delivers the endonuclease gene to a cell, tissue, or organism such that the endonuclease is expressed and able to cut the genome of the cell at a recognition site for the endonuclease endogenously within the genome. The delivered endonuclease will also find its target site within the self-limiting viral vector, and cut the vector at this target site. Once cut, the 5' and 3' ends of the viral genome will be exposed and degraded by exonucleases, thus killing the virus and ceasing production of the exogenous endonuclease.

In some aspects, the endonuclease of the self-limiting viral vector is a meganuclease, ZFN, TALEN, Compact TALEN, or CRISPR/Cas9, the endonuclease being either engineered or wild-type.

In more aspects, the location of the endonuclease recognition sequence may vary within the self-limiting viral vector. In these aspects the general construction of the self-limiting viral vector comprises from a 5' region of the ITRs: a promoter, a coding sequence for the endonuclease and polyA. The recognition sequence varies in its position. For example, in one aspect, the recognition sequence may follow, be 3' from, the coding for the endonuclease and polyA. Alternatively, in other aspects, the recognition sequence may be placed upstream, or 5' from, of the promoter in the self-limiting viral vector. Moreover, in some aspects, the recognition sequence may be placed within an intron of the endonuclease sequence. Additionally, in another aspect, the endonuclease recognition sequence may be placed between the promoter and the endonuclease coding sequence. The endonuclease recognition sequence may be placed within the self-limiting viral vector in any position where it will be recognized by the endonuclease and result in termination of transcription of the viral genome.

In some embodiments it is advantageous to modify the endonuclease recognition sequence such that recognition by the endonuclease is sub-optimal. In one aspect, an engineered meganuclease recognition sequence may have 1-2 basepair changes selected from bases 1, 10, 11, 12, 13, or 22 within the recognition sequence.

In some embodiments, the expressed endonuclease of the self-limiting viral vector is engineered to recognize a gene sequence of interest in the host genome, such that the endonuclease recognizes and cuts the genome at a specific site within the gene of interest, and wherein the cut initiates non-homologous end joining (NHEJ) such that mutations are introduced into the gene, and the gene of interest can no longer be translated correctly. In these embodiments, the endonuclease also recognizes the endonuclease recognition sequence within the self-limiting viral vector and cuts the vector genome, thus ceasing the transcription of the endonuclease and the persistence of the viral vector.

In other embodiments, the self-limiting viral vector can remove a region of interest within the cell genome. In these embodiments, the self-limiting viral vector contains coding for multiple endonucleases and the endonuclease recognition sequence is placed between the 3' end of one endonuclease sequence, and before the promoter of a second endonuclease sequence, the endonuclease recognition site recognized by one of the expressed endonucleases, and each endonuclease identifying and introducing a break in the genome of the cell at a site on either the 5' or 3' end of a region of interest within the cell genome. Once broken, the region of interest being excised from the genome, and the resulting ends being religated in the genome, the region of interest having been removed from the cell genome.

In some aspects, where more than one endonuclease is contained within the self-limiting viral vector, the endonuclease recognition site may be placed in variable places within the self-limiting viral vector that do not disrupt the functioning of the self-limiting viral vector, and the recognition site is specific to at least one of the endonucleases within the self-limiting viral vector. Moreover, the endonuclease recognition site capable of modification such that detection by the transcribed endonuclease is sub-optimal, as is described in other embodiments.

In other aspects, the self-limiting viral vector may be used to deliver a transgene to a region of interest within the cell genome. In these aspects, the self-limiting viral vector contains with in the ITRs from a 5' position: a promoter, endonuclease sequence, endonuclease recognition site, and a transgene flanked by homologous DNA sequences to the locus of interest. In further aspects, the expressed endonuclease recognizes and cuts a region of interest within the genome, and also recognizes and cuts at the endonuclease recognition site within the self-limiting viral vector. Furthermore, in these aspects, the 5' end of the homologous DNA sequence adjacent to the transgene coded in the self-limiting viral vector is then integrated into the 5' end of the region of interest and the 3' end of the homologous DNA sequence adjacent to the transgene coded in the self-limiting viral vector is integrated into the 3; end of the region of interest by homologous recombination, thus providing the transgene within the genome of the cell.

In other aspects, the self-limiting viral vector contains within the ITRs from a 5' position: a promoter, endonuclease sequence, endonuclease recognition site, and a gene sequence. In these aspects, the expressed endonuclease cuts a gene sequence within the genome, and cuts at the endonuclease recognition site within the self-limiting viral vector. Furthermore, in these aspects, the 5' end of gene sequence in the self-limiting viral vector is then integrated into the 5' end of gene sequence within the host cell genome containing a mutation and the 3' of the gene sequence in the self-limiting viral vector integrated into the 3' end of the gene sequence of the host cell genome by homologous recombination.

In one aspect the rAAV containing the self-limiting viral vector is produced using triple-transfection, wherein the packaging cell line is transfected with: 1. a plasmid containing "helper components," 2. a plasmid containing the cap and rep genes, and 3. a plasmid containing the self-limiting viral vector. In this aspect, the transfected packaging cell allowing for formation of the formed virus, that is then purified for infection of a cell, tissue, or organism.

In another aspect, the endonuclease coded for within the self-limiting viral vector is controlled by a tissue-specific promoter; the promoter inactive in the transfected packaging cell.

In further aspects, the self-limiting viral vector may be packaged in cells not endogenously expressing endonuclease (i.e., the use of mammalian promoters in microbial, plant, or insect cells).

The endonuclease gene of the self-limiting viral vector may also be operably linked to an inducible promoter, thus introducing the requirement of a small molecule for expression in some embodiments.

In some embodiments, the rAAV particles may be produced in mammalian cell lines expressing a transcription repressor, preventing the expression of the endonuclease gene within the self-limiting viral vector, wherein the transcription repressor can be encoded on a separate vector, the packaging vector outside of the ITRs, into the cap/rep vector, or stably integrated into the genome of the packaging cell.

In another aspect, the self-limiting viral vectors may be used as therapeutic agents for the treatment of genetic disorders. In some embodiments, the self-limiting viral vectors may be delivered by intravenous injection, injected into tissues (e.g., intramuscular or subretinal injection), hydrodynamic injection, intracranial injection, or direct injection.

In other embodiments, the self-limiting viral vectors are adenoviral or lentiviral/retroviral vectors to limit persistence times of the vector in cells.

In one aspect, the invention provides a viral vector comprising: (a) a first nucleic acid sequence encoding a first engineered nuclease; (b) a first promoter operably linked to the first nucleic acid sequence, wherein the first promoter is positioned 5' upstream of the first nucleic acid sequence and drives expression of the first engineered nuclease in a target cell; and (c) a first vector recognition sequence which is recognized and cleaved by the first engineered nuclease.

In one embodiment, the viral vector can have a lower persistence time in the target cell when compared to a viral vector which does not comprise the recognition sequence but is otherwise identical.

In another embodiment, the recognition sequence can be identical to a first chromosomal recognition sequence present in the genome of the target cell.

In another embodiment, the recognition sequence can be a sub-optimal recognition sequence which is recognized and cleaved by the first engineered nuclease. In some embodiments, the sub-optimal recognition sequence differs by up to 2 nucleotides from an optimal recognition sequence. In another such embodiment, wherein the sub-optimal recognition sequence is a meganuclease recognition sequence, the 2 differing nucleotides can be at base positions 1, 10, 11, 12, 13, or 22 (from 5' to 3') of the sub-optimal recognition sequence.

In another embodiment, the first vector recognition sequence can be positioned 5' upstream of the first promoter.

In another embodiment, the first vector recognition sequence can be positioned 3' downstream of the first promoter and 5' upstream of the first nucleic acid sequence.

In another embodiment, the first vector recognition sequence can be positioned 3' downstream of the first nucleic acid sequence.

In another embodiment, the first nucleic acid sequence can comprise, from 5' to 3', a first exon, an intron, and a second exon. In one such embodiment, the first vector recognition sequence can be positioned within the intron of the first nucleic acid sequence. In a particular embodiment, the intron can be a human growth hormone intron (SEQ ID NO: 2) or an SV40 large T antigen intron (SEQ ID NO: 3).

In another embodiment, the viral vector can further comprise a first polyA sequence positioned 3' downstream of the first nucleic acid sequence. In one such embodiment, the first vector recognition sequence can be positioned 3' downstream of the first nucleic acid sequence and 5' upstream of the first polyA sequence. In another such embodiment, the first vector recognition sequence can be positioned 3' downstream of the first polyA sequence.

In another embodiment, the viral vector can further comprise a transgene sequence.

In one such embodiment, the transgene sequence can be positioned 3' downstream of the first nucleic acid sequence. In another such embodiment, the transgene sequence can be positioned 5' upstream of the first promoter In another such embodiment, the transgene sequence can be flanked by sequences homologous to sequences flanking a region of interest in the genome of the target cell.

In another such embodiment, the first chromosomal recognition sequence can be positioned within the region of interest in the genome of the target cell.

In another such embodiment, the first vector recognition sequence can be positioned 5' upstream of the transgene sequence.

In another such embodiment, the first vector recognition sequence can be positioned 3' downstream of the transgene sequence.

In another embodiment, the viral vector can further comprise a corrected gene.

In one such embodiment, the corrected gene sequence can be positioned 3' downstream of the first nucleic acid sequence.

In another such embodiment, the corrected gene sequence can be positioned 5' upstream of the first promoter.

In another such embodiment, the corrected gene sequence does not comprise the first vector recognition sequence.

In another such embodiment, the corrected gene sequence can correspond to a mutated gene sequence present in the genome of the target cell, wherein the mutated gene sequence can differ from the corrected gene sequence by at least one nucleotide and can comprise the first chromosomal recognition sequence.

In another such embodiment, the first vector recognition sequence can be positioned 5' upstream of the corrected gene sequence.

In another such embodiment, the first vector recognition sequence can be positioned 3' downstream of the corrected gene sequence.

In another embodiment, the viral vector can further comprise a second nucleic acid sequence encoding a second engineered nuclease.

In one such embodiment, the second nucleic acid sequence can be positioned 5' upstream of the first nucleic acid sequence, and 3' downstream of the first promoter, such that the first promoter drives expression of both the first engineered nuclease and the second engineered nuclease.

In another such embodiment, the viral vector can further comprise a second promoter operably linked to the second nucleic acid sequence, wherein the second promoter can be positioned 5' upstream of the second nucleic acid sequence and drives expression of the second engineered nuclease in the target cell.

In another such embodiment, the second promoter and the second nucleic acid sequence can be positioned 5' upstream of the first promoter.

In another such embodiment, the second promoter and the second nucleic acid sequence can be positioned 3' downstream of the first nucleic acid sequence.

In another such embodiment, the second engineered nuclease can recognize and cleave a second chromosomal recognition sequence present in the genome of the target cell.

In another such embodiment, the second promoter can be identical to the first promoter. In another such embodiment, the second promoter can differ from the first promoter.

In another such embodiment, the first chromosomal recognition sequence and the second chromosomal recognition sequence can flank the 5' end and the 3' end of a region of interest in the genome of the target cell.

In another such embodiment, the first chromosomal recognition sequence and the second chromosomal recognition sequence can be positioned on the same chromosome.

In another such embodiment, the first chromosomal recognition sequence and the second chromosomal recognition sequence can be positioned on different chromosomes.

In another such embodiment, the first vector recognition sequence can be positioned 5' upstream of the second nucleic acid sequence.

In another such embodiment, the first vector recognition sequence can be positioned 3' downstream of the second promoter (if present) and 5' upstream of the second nucleic acid sequence.

In another such embodiment, the first vector recognition sequence can be positioned 3' downstream of the second nucleic acid sequence.

In another such embodiment, the second nucleic acid sequence can comprise, from 5' to 3', a first exon, an intron, and a second exon. In one such embodiment, the first vector recognition sequence can be positioned within the intron of the second nucleic acid sequence. In a particular embodiment, the intron can be a human growth hormone intron (SEQ ID NO: 2) or an SV40 large T antigen intron (SEQ ID NO: 3).

In another such embodiment, the viral vector can further comprise a second polyA sequence positioned 3' downstream of the second nucleic acid sequence. In one such embodiment, the first vector recognition sequence can be positioned 3' downstream of the second nucleic acid sequence and 5' upstream of the second polyA sequence. In another such embodiment, the first vector recognition sequence can be positioned 3' downstream of the second polyA sequence.

In another embodiment, the viral vector can be an adeno-associated virus (AAV) vector, a retroviral vector, a lentiviral vector, or an adenoviral vector. In various embodiments, the viral vector can be any viral vector suitable for use in the invention, including but not limited to, viral vectors of the families Adenoviridae, Baculoviridae, Hepadnaviridae, Herpesviridae, Iridoviridae, Papillomaviridae, Parvoviridae, Polyomaviridae, and Poxviridae.

In a particular embodiment, the viral vector can be an AAV vector comprising a 5' inverted terminal repeat and a 3' inverted terminal repeat. In some such embodiments, the AAV vector can be a single-stranded AAV vector or a self-complementary AAV vector.

In another embodiment, the first promoter can be a tissue-specific promoter, a species-specific promoter, or an inducible promoter.

In another embodiment, the first engineered nuclease and/or the second engineered nuclease can be an engineered meganuclease, a zinc finger nuclease (ZFN), a TALEN, a compact TALEN, or a CRISPR/Cas9. In a particular embodiment, the first engineered nuclease and/or the second engineered nuclease is an engineered meganuclease.

In another embodiment, the first promoter can comprise one or more binding sites for a transcription repressor that binds to and silences the first promoter. In one such embodiment, the transcription repressor can be a Tet repressor, a Lac repressor, a Cre repressor, or a Lambda repressor.

In another embodiment, the first promoter can be an inducible promoter. In one such embodiment, the viral vector can further comprise a nucleic acid sequence encoding a ligand-inducible transcription factor which regulates activation of the first promoter.

In all embodiments, it is understood that the viral vector can comprise only one vector recognition sequence, but may comprise two or more vector recognition sequences which are recognized by the first engineered nuclease and/or any additional engineered nucleases encoded by the viral vector.

In another aspect, the invention provides a recombinant DNA construct encoding any viral vector of the invention.

In one embodiment, the recombinant DNA construct can encode a viral vector wherein the first promoter comprises one or more binding sites for a transcription repressor that binds to and silences the first promoter. In one such embodiment, the recombinant DNA construct can further comprise a nucleic acid sequence encoding the transcription repressor. In a particular embodiment, the nucleic acid sequence encoding the transcription repressor can be positioned outside of the coding sequence of the viral vector.

In another embodiment, the recombinant DNA construct can encode an AAV vector, a retroviral vector, a lentiviral vector, or an adenoviral vector. In a particular embodiment, the recombinant DNA construct encodes an AAV vector.

In another aspect, the invention provides a cell comprising any recombinant DNA construct of the invention.

In another aspect, the invention provides a method for producing a viral vector, the method comprising transforming a packaging cell with any recombinant DNA construct of the invention which encodes a viral vector, wherein the packaging cell produces the viral vector.

In one embodiment of the method, the viral vector can be a self-limiting viral vector which has a lower persistence time in the target cell when compared to a control viral vector that is not self-limiting and does not comprise a recognition sequence for a first engineered nuclease.

In another embodiment of the method, the packaging cell can be transformed with a recombinant DNA construct of the invention which comprises a first promoter comprising one or more binding sites for a transcription repressor that binds to and silences the first promoter. In one such embodiment of the method, the recombinant DNA construct can further comprise a nucleic acid sequence encoding the transcription repressor. In another such embodiment of the method, the nucleic acid sequence encoding the transcription repressor is positioned on the recombinant DNA construct outside of the coding sequence of the viral vector. In another such embodiment of the method, the packaging cell is further transformed with a second recombinant DNA construct comprising a nucleic acid sequence encoding the transcription repressor. In another such embodiment of the method, the packaging cell comprises in its genome a nucleic acid sequence encoding the transcription repressor, wherein the packaging cell stably expresses the transcription repressor.

In another embodiment of the method, the first promoter of the recombinant DNA construct can be a tissue-specific promoter that is inactive in the packaging cell; i.e., the tissue for which the promoter has specificity differs from the tissue from which the packaging cell is derived.

In another embodiment of the method, the first promoter of the recombinant DNA construct can be a species-specific promoter that is inactive in the packaging cell; i.e., the species for which the promoter has specificity differs from the species of the packaging cell. In one such embodiment of the method, the first promoter can be a mammalian promoter and the packaging cell can be a microbial cell, an insect cell, or a plant cell.

In another such embodiment of the method, the packaging cell can be an insect cell, and the first nucleic acid sequence encoding the first engineered nuclease can comprise a mammalian intron that prevents expression of the first engineered nuclease in the packaging cell.

In one particular embodiment of the method, the intron can be a human growth hormone intron (SEQ ID NO: 2) or an SV40 large T antigen intron (SEQ ID NO: 3).

In another embodiment of the method, the first promoter of the recombinant DNA construct can be an inducible-promoter which is regulated by a ligand-inducible transcription factor. In one such embodiment of the method, the recombinant DNA construct can further comprise a nucleic acid sequence encoding the ligand-inducible transcription factor. In a particular embodiment of the method, the nucleic acid sequence encoding the ligand-inducible transcription factor can be positioned within the coding sequence of the viral vector.

In another embodiment of the method, the viral vector can be an AAV vector, a retroviral vector, a lentiviral vector, or an adenoviral vector.

In a particular embodiment of the method, the viral vector can be an AAV vector. In such an embodiment, the method can further comprise transforming the packaging cell with: (a) a second recombinant DNA construct comprising a cap gene and a rep gene; and (b) a third recombinant DNA construct comprising adenoviral helper components.

In another aspect, the invention provides a method for producing a genetically-modified eukaryotic cell by disrupting a target sequence in a chromosome of the eukaryotic cell. In such an aspect, the method comprises transducing the eukaryotic cell with any viral vector of the invention; wherein the first engineered nuclease is expressed in the eukaryotic cell; wherein the first engineered nuclease produces a first cleavage site at a first chromosomal recognition sequence positioned within the target sequence; and wherein the target sequence is disrupted by non-homologous end-joining at the first cleavage site, and wherein the first engineered nuclease recognizes and cleaves the first vector recognition sequence in the viral vector.

In one embodiment of the method, the viral vector can have a lower persistence time in the target cell when compared to a viral vector which does not comprise the recognition sequence, but is otherwise identical.

In another embodiment, the target sequence can comprise any gene of interest.

In another aspect, the invention provides a method for producing a genetically-modified eukaryotic cell including an exogenous sequence of interest inserted in a chromosome of the eukaryotic cell. In such an aspect, the method comprises: (a) transducing the eukaryotic cell with any viral vector of the invention, wherein the first engineered nuclease encoded by the viral vector is expressed in the eukaryotic cell; and (b) introducing into the eukaryotic cell a nucleic acid comprising the exogenous sequence of interest; wherein the first engineered nuclease produces a first cleavage site in the chromosome at a first chromosomal recognition sequence; and wherein the exogenous sequence of interest is inserted into the chromosome at the first cleavage site; and wherein the first engineered nuclease recognizes and cleaves the first vector recognition sequence in the viral vector.

In one embodiment of the method, the viral vector can have a lower persistence time in the target cell when compared to a viral vector which does not comprise the recognition sequence but is otherwise identical.

In one embodiment of the method, the nucleic acid comprising the exogenous sequence of interest can further comprise sequences homologous to sequences flanking the first cleavage site, and the exogenous sequence of interest is inserted at the first cleavage site by homologous recombination.

In another embodiment of the method, the nucleic acid comprising the exogenous sequence of interest can lack substantial homology to sequences flanking the first cleavage site, and the exogenous sequence of interest can be inserted at the first cleavage site by non-homologous end-joining.

In another aspect, the invention provides a method for producing a genetically-modified eukaryotic cell including an exogenous sequence of interest (i.e., a transgene sequence) inserted in a chromosome of the eukaryotic cell. In such an aspect, the method comprises transducing the eukaryotic cell with any viral vector of the invention which comprises a transgene sequence; wherein the first engineered nuclease is expressed in the eukaryotic cell; and wherein the first engineered nuclease produces a first cleavage site in the chromosome at the first chromosomal recognition sequence; and wherein the exogenous sequence of interest (i.e., the transgene sequence) is inserted into the chromosome at the first cleavage site; and wherein the first engineered nuclease recognizes and cleaves the first vector recognition sequence in the viral vector.

In one embodiment of the method, the viral vector can have a lower persistence time in the target cell when compared to a viral vector which does not comprise the recognition sequence but is otherwise identical.

In another embodiment of the method, the exogenous sequence of interest (i.e., the transgene sequence) on the viral vector can be flanked by sequences homologous to sequences flanking the first cleavage site, and the exogenous sequence of interest can be inserted at the first cleavage site by homologous recombination.

In another embodiment of the method, the exogenous sequence of interest (i.e., the transgene sequence) on the viral vector can lack flanking sequences having substantial homology to the first cleavage site, and the exogenous sequence of interest can be inserted at the first cleavage site by non-homologous end-joining.

In another aspect, the invention provides a method for producing a genetically-modified eukaryotic cell including a corrected gene in a chromosome of the eukaryotic cell. In such an aspect, the method comprises transducing the eukaryotic cell with any viral vector of the invention comprising a corrected gene sequence; wherein the first engineered nuclease is expressed in the eukaryotic cell; and wherein the eukaryotic cell comprises a mutated gene, wherein the mutated gene comprises the first chromosomal recognition sequence; and wherein the first engineered nuclease produces a first cleavage site at the first chromosomal recognition sequence; and wherein the mutated gene is replaced with the corrected gene sequence of the viral vector by homologous recombination to produce a corrected gene in the eukaryotic cell; and wherein the first engineered nuclease recognizes and cleaves the first vector recognition sequence in the viral vector.

In one embodiment of the method, the viral vector can have a lower persistence time in the target cell when compared to a viral vector which does not comprise the recognition sequence but is otherwise identical.

In another embodiment of the method, the mutation present within the mutated gene sequence can be positioned within the first chromosomal recognition sequence. In another embodiment of the method, the mutation present within the mutated gene sequence can be positioned within 10 bases, 100 bases, or up to 1000 bases of the first chromosomal recognition sequence. Preferably, the mutation is positioned less than 25 bases from the first chromosomal recognition sequence.

In another embodiment of the method, the corrected gene sequence in the viral vector does not comprise the first vector recognition sequence.

In another aspect, the invention provides a method for producing a genetically-modified eukaryotic cell including a deletion of a sequence of interest in a chromosome of the eukaryotic cell. In such an aspect, the method comprises transducing the eukaryotic cell with any viral vector of the invention comprising a first nucleic acid sequence encoding a first engineered nuclease and a second nucleic acid sequence encoding a second engineered nuclease; wherein the first engineered nuclease and the second engineered nuclease are expressed in the eukaryotic cell; and wherein the first chromosomal recognition sequence and the second chromosomal recognition sequence flank the sequence of interest on the chromosome; and wherein the first engineered nuclease produces a first cleavage site in the chromosome at the first chromosomal recognition sequence; and wherein the second engineered nuclease produces a second cleavage site in the chromosome at the second chromosomal recognition sequence; and wherein the intervening DNA fragment between the first cleavage site and the second cleavage site is excised; and wherein the chromosome is repaired by re-ligation of the first cleavage site and the second cleavage site; and wherein the first engineered nuclease recognizes and cleaves the first vector recognition sequence in the viral vector.

In one embodiment of the method, the viral vector can have a lower persistence time in the target cell when compared to a viral vector which does not comprise the recognition sequence but is otherwise identical.

In another aspect, the invention provides a method for producing a genetically-modified eukaryotic cell including an exogenous sequence of interest inserted in a chromosome of the eukaryotic cell. In such an aspect, the method comprises: (a) transducing the eukaryotic cell with any viral vector of the invention comprising a first nucleic acid sequence encoding a first engineered nuclease and a second nucleic acid sequence encoding a second engineered nuclease; wherein the first engineered nuclease and the second engineered nuclease are expressed in the eukaryotic cell; and (b) transforming the eukaryotic cell with a nucleic acid comprising the exogenous sequence of interest; wherein the first engineered nuclease produces a first cleavage site in the chromosome at the first chromosomal recognition sequence; and wherein the second engineered nuclease produces a second cleavage site in the chromosome at the second chromosomal recognition sequence; and wherein the exogenous sequence of interest is inserted into the chromosome between the first cleavage site and the second cleavage site; and wherein the first engineered nuclease recognizes and cleaves the first vector recognition sequence in the viral vector.

In one embodiment of the method, the viral vector can have a lower persistence time in the target cell when compared to a viral vector which does not comprise the recognition sequence but is otherwise identical.

In another embodiment of the method, the exogenous sequence of interest can be flanked on the nucleic acid by a sequence homologous to the region 5' upstream of the first cleavage site and a sequence homologous to the region 3' downstream of the second cleavage site, and the exogenous sequence of interest can be inserted between the first cleavage site and the second cleavage site by homologous recombination.

In another embodiment of the method, the nucleic acid comprising the exogenous sequence of interest can lack substantial homology to sequences flanking the first cleavage site and the second cleavage site, and the exogenous sequence of interest can be inserted into the chromosome between the first cleavage site and the second cleavage site by non-homologous end-joining.

In another aspect, the invention provides a method for producing a genetically-modified eukaryotic cell by disrupting a first target sequence and a second target sequence in the genome of the eukaryotic cell. In such an aspect, the method comprises transducing the eukaryotic cell with any viral vector of the invention comprising a first nucleic acid sequence encoding a first engineered nuclease and a second nucleic acid sequence encoding a second engineered nuclease; wherein the first engineered nuclease and the second engineered nuclease are expressed in the eukaryotic cell; and wherein the first engineered nuclease produces a first cleavage site at a first chromosomal recognition sequence positioned within the first target sequence; and wherein the second engineered nuclease produces a second cleavage site at a second chromosomal recognition sequence positioned within the second target sequence; and wherein the first target sequence and the second target sequence are disrupted by non-homologous end-joining at the first cleavage site and at the second cleavage site; and wherein the first engineered nuclease recognizes and cleaves the first vector recognition sequence in the viral vector.

In another embodiment of the method, the viral vector can have a lower persistence time in the target cell when compared to a viral vector which does not comprise the recognition sequence but is otherwise identical.

In one embodiment of the method, the first target sequence and/or the second target sequence in the genome can be any gene of interest.

In another embodiment of the method, the first target sequence and the second target sequence can be on the same chromosome. In another embodiment of the method, the first target sequence and the second target sequence can be on different chromosomes.

In another aspect, the invention provides a method for producing a genetically-modified eukaryotic cell including a first exogenous sequence of interest inserted in the genome of the eukaryotic cell. In such an aspect, the method comprises: (a) transducing the eukaryotic cell with any viral vector of the invention comprising a first nucleic acid sequence encoding a first engineered nuclease and a second nucleic acid sequence encoding a second engineered nuclease; and (b) introducing into the eukaryotic cell a first nucleic acid comprising a first exogenous sequence of interest; wherein the first engineered nuclease and the second engineered nuclease are expressed in the eukaryotic cell; and wherein the first engineered nuclease produces a first cleavage site at a first chromosomal recognition sequence positioned within a first target sequence; and wherein the second engineered nuclease produces a second cleavage site at a second chromosomal recognition sequence positioned within a second target sequence; and wherein the first exogenous sequence of interest is inserted into the genome at the first cleavage site; and wherein the first engineered nuclease recognizes and cleaves the recognition sequence in the viral vector; and wherein the first engineered nuclease recognizes and cleaves the first vector recognition sequence in the viral vector.

In one embodiment of the method, the viral vector can have a lower persistence time in the target cell when compared to a viral vector which does not comprise the recognition sequence but is otherwise identical.

In another embodiment of the method, the first target sequence can be disrupted by insertion of the first exogenous sequence of interest into the first cleavage site.

In another embodiment of the method, the first nucleic acid can comprise sequences flanking the first exogenous sequence of interest which are homologous to sequences flanking the first cleavage site, and the first exogenous sequence of interest can be inserted at the first cleavage site by homologous recombination.

In another embodiment of the method, the first nucleic acid comprising the first exogenous sequence of interest can lack substantial homology to sequences flanking the first cleavage site, and the first exogenous sequence of interest can be inserted into the first cleavage site by non-homologous end-joining.

In another embodiment of the method, the second target sequence can be disrupted by non-homologous end-joining following the production of the second cleavage site. Thus, in a particular embodiment, the first target sequence can be disrupted following insertion of the first exogenous sequence of interest into the first cleavage site, and the second target sequence can be disrupted by non-homologous end-joining following the production of the second cleavage site.

In another embodiment of the method, the first nucleic acid can comprise a first copy and a second copy of the first exogenous sequence of interest. In one such embodiment, the first copy can be inserted into the genome at the first cleavage site and the second copy can be inserted into the genome at the second cleavage site. In such an embodiment, the first target sequence and the second target sequence can each be disrupted by insertion of each copy of the first exogenous sequence of interest.

In one such embodiment of the method, the first nucleic acid can comprise sequences flanking the first copy which are homologous to sequences flanking the first cleavage site, and/or can comprise sequences flanking the second copy which are homologous to sequences flanking the second cleavage site. In such embodiments, the first copy and/or the second copy can be inserted at the first cleavage site and/or the second cleavage site by homologous recombination.

In another such embodiment of the method, the first nucleic acid comprising the first exogenous sequence of interest can lack substantial homology to sequences flanking the first cleavage site and/or the second cleavage site, and the first copy and/or the second copy can be inserted into the first cleavage site and/or the second cleavage site by non-homologous end-joining.

In another embodiment of the method, the first nucleic acid can comprise both the first exogenous sequence of interest and a second exogenous sequence of interest. In one such embodiment of the method, the first exogenous sequence of interest can be inserted into the first cleavage site, and the second exogenous sequence of interest can be inserted into the second cleavage site. In such an embodiment, the first target sequence and/or the second target sequence can be disrupted following insertion of the first exogenous sequence of interest and/or the second exogenous sequence of interest.

In one such embodiment of the method, the first nucleic acid can comprise sequences flanking the first exogenous sequence of interest which are homologous to sequences flanking the first cleavage site. The first nucleic acid can also comprise sequences flanking the second exogenous sequence of interest which are homologous to sequences flanking the second cleavage site. In such an embodiment, the first exogenous sequence of interest can be inserted at the first cleavage site and the second exogenous sequence of interest can be inserted at the second cleavage site by homologous recombination.

In another such embodiment of the method, the first nucleic acid comprising the first exogenous sequence of interest and the second exogenous sequence of interest can lack substantial homology to sequences flanking the first cleavage site and/or the second cleavage site, and the first exogenous sequence of interest can be inserted into the first cleavage site, and the second exogenous sequence of interest can be inserted into the second cleavage site, by non-homologous end-joining.

In another embodiment, the method can further comprise introducing into the eukaryotic cell a second nucleic acid comprising a second exogenous sequence of interest.

In one such embodiment, the first exogenous sequence of interest can be inserted into the first cleavage site and the second exogenous sequence of interest can be inserted into the second cleavage site. In a particular embodiment, the first target sequence can be disrupted by insertion of the first exogenous sequence of interest into the first cleavage site, and the second target sequence can be disrupted by insertion of the second exogenous sequence of interest into the second cleavage site.

In another such embodiment of the method, the first nucleic acid can comprise sequences flanking the first exogenous sequence of interest which are homologous to sequences flanking the first cleavage site, and/or the second nucleic acid can comprise sequences flanking the second exogenous sequence of interest which are homologous to sequences flanking the second cleavage site. In such an embodiment, the first exogenous sequence of interest can be inserted at the first cleavage site, and/or the second exogenous sequence of interest can be inserted at the second cleavage site by homologous recombination.

In another such embodiment of the method, the first nucleic acid comprising the first exogenous sequence of interest can lack substantial homology to sequences flanking the first cleavage site, and/or the second nucleic acid comprising the second exogenous sequence of interest can lack substantial homology to sequences flanking the second cleavage site. In such an embodiment, the first exogenous sequence of interest can be inserted into the first cleavage site, and/or the second exogenous sequence of interest can be inserted in the second cleavage site, by non-homologous end-joining.

In some such embodiments of the method, the first target sequence and the second target sequence can be on the same chromosome. In other such embodiments of the method, the first target sequence and the second target sequence can be on different chromosomes.

In each embodiment of the method, the first target sequence and/or the second target sequence can be any gene of interest. In such embodiments, disruption of the first target sequence and/or disruption of the second target sequence can result in reduced expression of the gene.

In another aspect, the invention provides a method for producing a genetically-modified non-human organism comprising: (a) producing a genetically-modified eukaryotic cell of the invention, wherein the eukaryotic cell is a non-human eukaryotic cell; and (b) growing the genetically-modified non-human eukaryotic cell to produce the genetically-modified non-human organism.

In one embodiment, the non-human eukaryotic cell is selected from the group consisting of a gamete, a zygote, a blastocyst cell, an embryonic stem cell, and a protoplast cell.

In another aspect, the invention provides a method for treating a disease in a subject in need thereof. In such an aspect, the method comprises administering to the subject a pharmaceutical composition comprising any viral vector of the invention and a pharmaceutically acceptable carrier.

In one embodiment, the disease can be cancer. In another embodiment, the disease can be a genetic disorder. In such an embodiment, the disease can be a hereditary or a non-hereditary genetic disorder.

In another aspect, the invention provides a viral vector described herein for use as a medicament. The invention further provides the use of a viral vector described herein in the manufacture of a medicament for treating a disease in a subject in need thereof.

In a particular aspect, the invention provides any AAV vector described herein for use as a medicament. The invention further provides the use of an AAV vector in the manufacture of a medicament for treating a disease in a subject in need thereof.

In another aspect, the invention provides any genetically-modified cell of the invention for use as a medicament. The invention further provides the use of any genetically-modified cell of the invention in the manufacture of a medicament for treating a disease in a subject in need thereof.

BRIEF DESCRIPTION OF THE FIGURES

FIGS. 1A-1D show example embodiments of vector compositions wherein the recognition site is positioned in variable locations relative to the endonuclease gene and its associated promoter.

FIG. 6A) The OLR plasmid DNA vector (SEQ ID NO: 4) is illustrated. The OLR vector comprises a coding sequence for an MDX 1/2 meganuclease operably-linked to a CMV promoter. The CMV promoter is modified to include three Lac operon sequences. The OLR vector further comprises a cassette including a Lad coding sequence for expression of a Lac repressor that binds to the Lac operons and suppresses expression of the nuclease gene. FIG. 6B) The 3×Oi plasmid DNA vector (SEQ ID NO: 5) is illustrated. The 3×Oi vector comprises the same elements as the OLR vector but lacks the cassette comprising the LacI coding sequence. Thus, no Lac repressor would be expressed and the nuclease gene would not be suppressed.

FIG. 9A) Vector map of the pDS CMV RHO 1/2—HGH plasmid DNA vector (SEQ ID NO: 7). This vector comprises a RHO 1/2 meganuclease coding sequence which includes a human growth hormone intron 1 (SEQ ID NO: 2) within its sequence. FIG. 9B) Vector map of the pDS CMV RHO 1/2-SV40LT plasmid DNA vector (SEQ ID NO: 8). This vector comprises a RHO 1/2 meganuclease coding sequence which includes an SV40 large T intron 1 (SEQ ID NO: 2) within its sequence.

FIG. 10A) Vector map of the pDS CMV 3×Oi RHO 1/2 L514 LacI plasmid DNA vector (SEQ ID NO: 9). FIG. 10B) Vector map of the pDS CMV 3×Oi RHO 1/2 L514 plasmid DNA vector (SEQ ID NO: 10).

BRIEF DESCRIPTION OF THE SEQUENCES

Figure 1A:
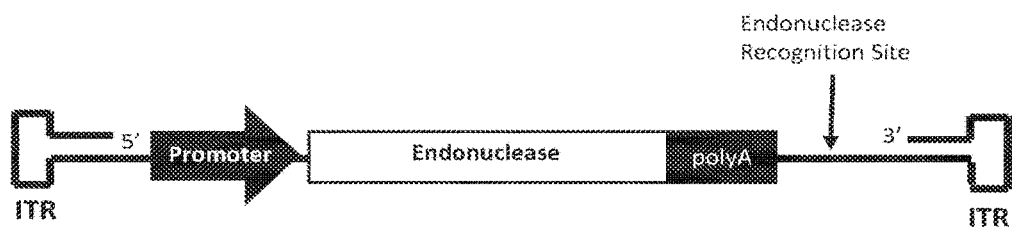
FIGS. 1A-1D. Diagrams of example self-limiting rAAV vectors. The vector genome is shown with ITRs at the ends. Each vector encodes a site-specific endonuclease and a recognition site for the endonuclease in the genome.
Figure 1B:
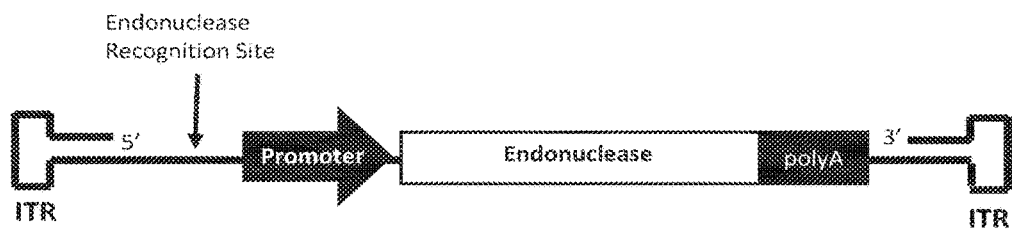
Figure 1C:
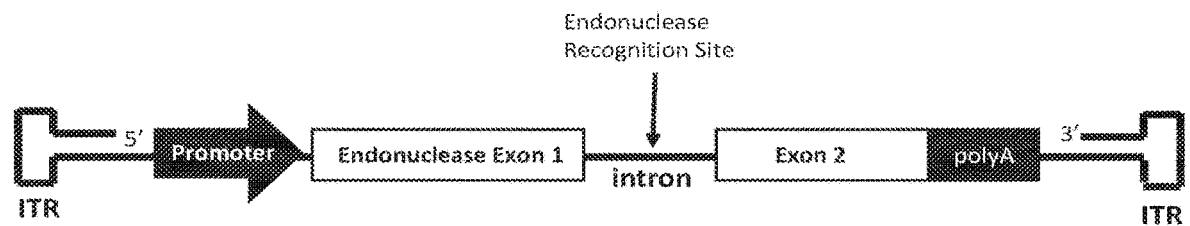
Figure 1D:
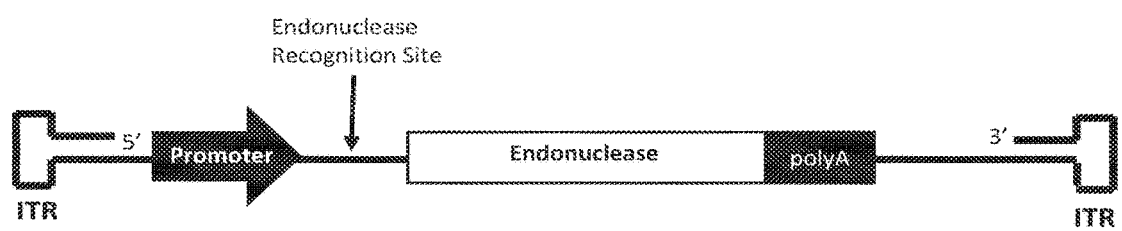

SEQ ID NO: 1 sets forth the amino acid sequence of the wild-type I-CreI meganuclease.
SEQ ID NO: 2 sets forth the nucleic acid sequence of the human growth hormone intron 1.
SEQ ID NO: 3 sets forth the nucleic acid sequence of the SV40 large T antigen intron.
SEQ ID NO: 4 sets forth the nucleic acid sequence of the OLR DNA plasmid.
SEQ ID NO: 5 sets forth the nucleic acid sequence of the 3×Oi plasmid.
SEQ ID NO: 6 sets forth the nucleic acid sequence of the pDS GRK1 RH1/2 L5-14 plasmid.
SEQ ID NO: 7 sets forth the nucleic acid sequence of the pDS CMV RHO 1/2-HGH plasmid.
SEQ ID NO: 8 sets forth the nucleic acid sequence of the pDS CMV RHO 1/2-SV40LT plasmid.
SEQ ID NO: 9 sets forth the nucleic acid sequence of the pDS CMV 3×Oi RHO 1/2 L514 Lad plasmid.
SEQ ID NO: 10 sets forth the nucleic acid sequence of the pDS CMV 3×Oi RHO 1/2 L514 plasmid.

DETAILED DESCRIPTION OF THE INVENTION

1.1 References and Definitions

The patent and scientific literature referred to herein establishes knowledge that is available to those of skill in the art. The entire disclosures of the issued U.S. patents, pending applications, published foreign applications, and references, including GenBank database sequences, that are cited herein are hereby incorporated by reference to the same extent as if each was specifically and individually indicated to be incorporated by reference.

Reference will now be made in detail to the preferred embodiments of the self-limiting viral vector, examples of which are illustrated in the accompanying drawings.

As used herein, the term "cell" refers to a cell, whether it be part of a cell line, tissue, or organism. "Cell" may refer to microbial, plant, insect, or animalian (mammalian, reptilian, avian, or otherwise) type, and where necessary, is specified.

As used herein, the term "meganuclease" refers to an endonuclease that is derived from I-CreI. The term meganuclease, as used herein, refers to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (i.e. WO 2007/047859). A meganuclease may bind to double-stranded DNA as a homodimer, as is the case for wild-type I-CreI, or it may bind to DNA as a heterodimer. A meganuclease may also be a "single-chain meganuclease" in which a pair of DNA-binding domains derived from I-CreI are joined into a single polypeptide using a peptide linker.

As used herein, the term "single-chain meganuclease" refers to a polypeptide comprising a pair of meganuclease subunits joined by a linker. A single-chain meganuclease has the organization: N-terminal subunit—Linker—C-terminal subunit. The two meganuclease subunits, each of which is derived from I-CreI, will generally be non-identical in amino acid sequence and will recognize non-identical DNA sequences. Thus, single-chain meganucleases typically cleave pseudo-palindromic or non-palindromic recognition sequences. A single chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "site specific endonuclease" means a meganuclease, TALEN, Compact TALEN, Zinc-Finger Nuclease, or CRISPR.

As used herein, the term "Compact TALEN" refers to an endonuclease comprising a DNA-binding domain with 16-22 TAL domain repeats fused in any orientation to any portion of the I-TevI homing endonuclease.

As used herein, the term "Zinc-Finger Nuclease" refers to an endonuclease comprising a DNA-binding domain comprising 3-5 zinc-finger domains fused to any portion of the FokI nuclease domain.

As used herein, the term "TALEN" refers to an endonuclease comprising a DNA-binding domain comprising 16-22 TAL domain repeats fused to any portion of the FokI nuclease domain.

As used herein, the term "CRISPR" refers to a caspase-based endonuclease comprising a caspase, such as Cas9, and a guide RNA that directs DNA cleavage of the caspase by hybridizing to a recognition site in the genomic DNA.

As used herein, with respect to a protein, the term "recombinant" means having an altered amino acid sequence as a result of the application of genetic engineering techniques to nucleic acids which encode the protein, and cells or organisms which express the protein. With respect to a nucleic acid, the term "recombinant" means having an altered nucleic acid sequence as a result of the application of genetic engineering techniques. Genetic engineering techniques include, but are not limited to: PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant. As used herein, the term "engineered" is synonymous with the term "recombinant."

As used herein, the term "wild-type" refers to any naturally-occurring form of a meganuclease. The term "wild-type" is not intended to mean the most common allelic variant of the enzyme in nature but, rather, any allelic variant found in nature. Wild-type homing endonucleases are distinguished from recombinant or non-naturally-occurring meganucleases.

As used herein, the term "recognition sequence" refers to a DNA sequence that is bound and cleaved by an endonuclease. In the case of a meganuclease, a recognition sequence comprises a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' "overhangs". "Overhangs", or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence. In the case of a Compact TALEN, the recognition sequence comprises a first CNNNGN sequence that is recognized by the I-TevI domain, followed by a non-specific spacer 4-16 basepairs in length, followed by a second sequence 16-22 bp in length that is recognized by the TAL-effector domain (this sequence typically has a 5' T base). Cleavage by a Compact TALEN produces two basepair 3' overhangs. In the case of a CRISPR, the recognition sequence is the sequence, typically 16-24 basepairs, to which the guide RNA binds to direct Cas9 cleavage. Cleavage by a CRISPR produces blunt ends. In the case of a zinc finger, the DNA binding domains typically recognize an 18-bp recognition sequence comprising a pair of nine basepair "half-sites" separated by 2-10 basepairs and cleavage by the nuclease creates a blunt end or a 5' overhang of variable length (frequently four basepairs).

As used herein, the term "target site" or "target sequence" refers to a region of the chromosomal DNA of a cell comprising a recognition sequence for a site specific endonuclease.

As used herein, the term "homologous recombination" or "HR" refers to the natural, cellular process in which a double-stranded DNA-break is repaired using a homologous DNA sequence as the repair template (see, e.g. Cahill et al. (2006) Front. Biosci. 11:1958-1976). The homologous DNA sequence may be an endogenous chromosomal sequence or an exogenous nucleic acid that was delivered to the cell. The term "homology" is used herein as equivalent to "sequence similarity" and is not intended to require identity by descent or phylogenetic relatedness.

As used herein, the term "non-homologous end-joining" or "NHEJ" refers to the natural, cellular process in which a double-stranded DNA-break is repaired by the direct joining of two non-homologous DNA segments (see, i.e. Cahill et al. (2006) Front. Biosci. 11:1958-1976). DNA repair by non-homologous end-joining is error-prone and frequently results in the untemplated addition or deletion of DNA sequences at the site of repair. The process of non-homologous end-joining occurs in both eukaryotes and prokaryotes such as bacteria.

As used herein, the term "re-ligation" refers to a process in which two DNA ends produced by a pair of double-strand DNA breaks are covalently attached to one another with the loss of the intervening DNA sequence but without the gain or loss of any additional DNA sequence. In the case of a pair of DNA breaks produced with single-strand overhangs, re-ligation can proceed via annealing of complementary overhangs followed by covalent attachment of 5' and 3' ends by a DNA ligase. Re-ligation is distinguished from NHEJ in that it does not result in the untemplated addition or removal of DNA from the site of repair.

As used herein, the term "concatamer" refers to long continuous DNA molecules that contain multiple copies of the same DNA sequence linked in series, As used herein, the term "persistence" or "persist" refers to the viability of the self-limiting viral vector in the cell, tissue, or organism of interest. Attenuating persistence time refers to the degradation of the vector, and thus, viral genome.

As used herein, unless specifically indicated otherwise, the word "or" is used in the inclusive sense of "and/or" and not the exclusive sense of "either/or."

2.1 Self-Limiting Viral Vectors

The present invention is based, in part, on the premise that a viral vector, such as a rAAV vector, will not persist in a cell after cleavage of the DNA by an endonuclease. rAAV is a preferred vector for delivery of genome editing endonucleases to cells and tissues, but its long persistence time in cells presents a problem. Genome editing applications using site-specific endonucleases generally do not require long-term expression of the endonuclease gene, and long-term expression may be harmful. Long-term expression of endonucleases may hinder cleavage specificity, thus introducing breakage in unintended sites, which may lead to detrimental consequences for cell health. Moreover, cell machinery is designed to detect and immunologically respond to the production of foreign proteins, such as endonucleases introduced by the rAAV vector. (Mingozzi F, and High K (2013) *Blood* 122(1):23-26). Thus, the invention provides vectors in which vector persistence time is "self-limited" through a recognition sequence for the genome editing endonuclease already incorporated into the vector.

The self-limiting viral vector is thus able to deliver the endonuclease gene to a cell or tissue such that the endonuclease is expressed and able to modify the genome of the cell. In addition, the same endonuclease will find its target site within the vector and will cut the genome of the virus, exposing free 5' and 3' ends and initiating degradation by exonucleases. It is taught herein that cleavage of the viral genome will prevent the virus from forming concatamers that can persist stably in the cell as episomes. Thus, the virus effectively "kills itself."

The precise location of the endonuclease recognition sequence may vary, as exemplified in FIG. 1. Certain configurations are preferred when possible. One preferred configuration is shown in FIG. 1C where the endonuclease recognition sequence is positioned within an intron in the endonuclease gene. Intracellular cleavage of such a vector is expected to separate the two endonuclease exons such that the endonuclease gene can no longer be expressed. This leads to a more rapid attenuation of endonuclease expression. Alternatively, it is possible to position the endonuclease recognition sequence between the endonuclease gene and its promoter (i.e. in the 5' UTR), as shown in FIG. 1D. This configuration will also quickly attenuate expression of the endonuclease while not adding as much additional size to the gene. Also depicted in FIG. 1A, the endonuclease recognition sequence may be placed after the endonuclease gene sequence and polyA, or the endonuclease recognition site may be placed before the promoter in the 5' position of the ITR as depicted in FIG. 1B. The endonuclease recognition site may be placed in various locations, as long as the site does not interfere with the proper expression of the endonuclease, and is accessible by the expressed nuclease.

Figure 2:
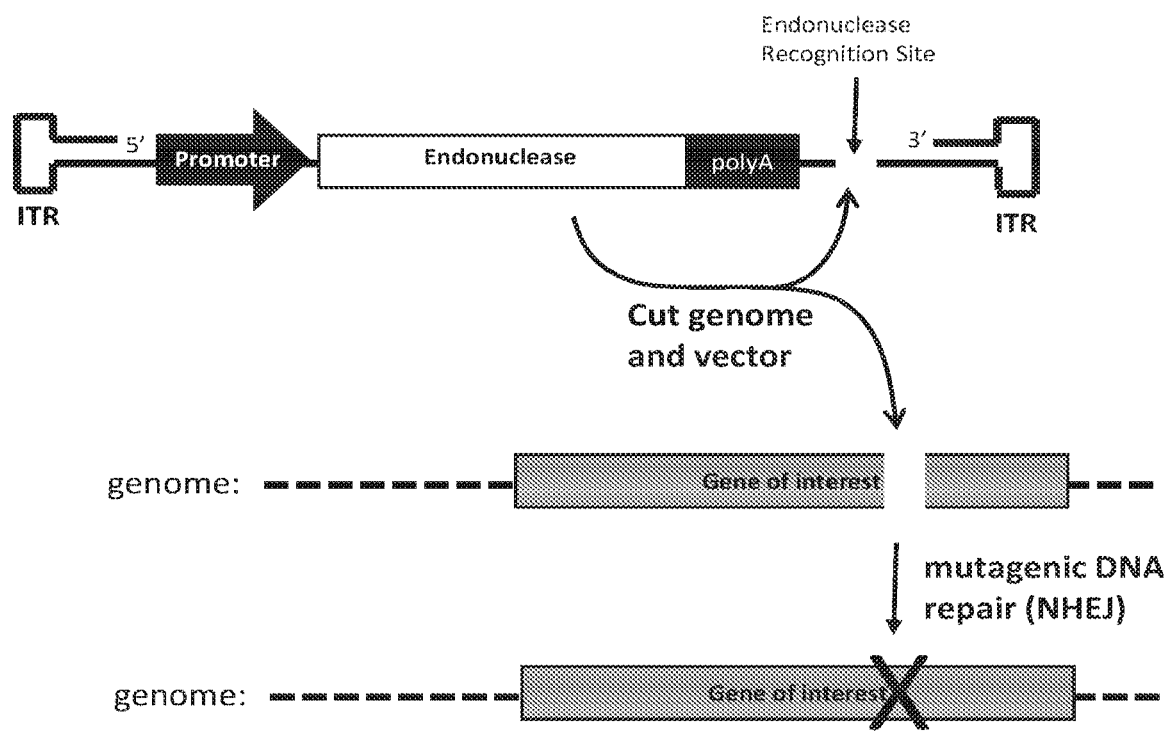
FIG. 2. General method for using a self-limiting rAAV vector to knock-out a gene. In this embodiment, a self-limiting viral vector is delivered to a cell or organism, the vector encoding a site-specific endonuclease that recognizes a target sequence in the coding sequence of a gene of interest within the cell. Following infection with the vector, the cell expresses the endonuclease. The endonuclease then cuts both the recognition site in the genome of the cell and the recognition site in the genome of the virus. The DNA break in the cell genome is repaired by non-homologous end-joining (NHEJ), which introduces mutations into the gene, thus disabling it. The cut virus is quickly degraded by exonucleases and ceases to persist in the cell or organism.

The self-limiting viral vectors created can be used to infect cells, tissues, or organisms to achieve a multitude of therapeutic results. For instance, as exemplified in FIG. 2, self-limiting viral vectors can be used to disable ("knock-out") a gene.]. In infected cells, the expressed endonuclease within the cell recognizes a target sequence within a coding sequence of a gene of interest within the cell (that cell being part of a cell line, tissue, or organism) and cuts the DNA. The DNA break in the cell's genome will then be repaired by non-homologous end-joining (NHEJ), such that mutations are introduced at the target site that disables the gene of interest's function. Subsequently, the expressed endonuclease recognizes and cuts the self-limiting viral vector at the endonuclease recognition sequence. Once cut, the self-limiting viral vector cannot produce concameters that may otherwise form and persist within the episomes. The self-limiting viral vector will cease to persist within the cell.

Figure 3:
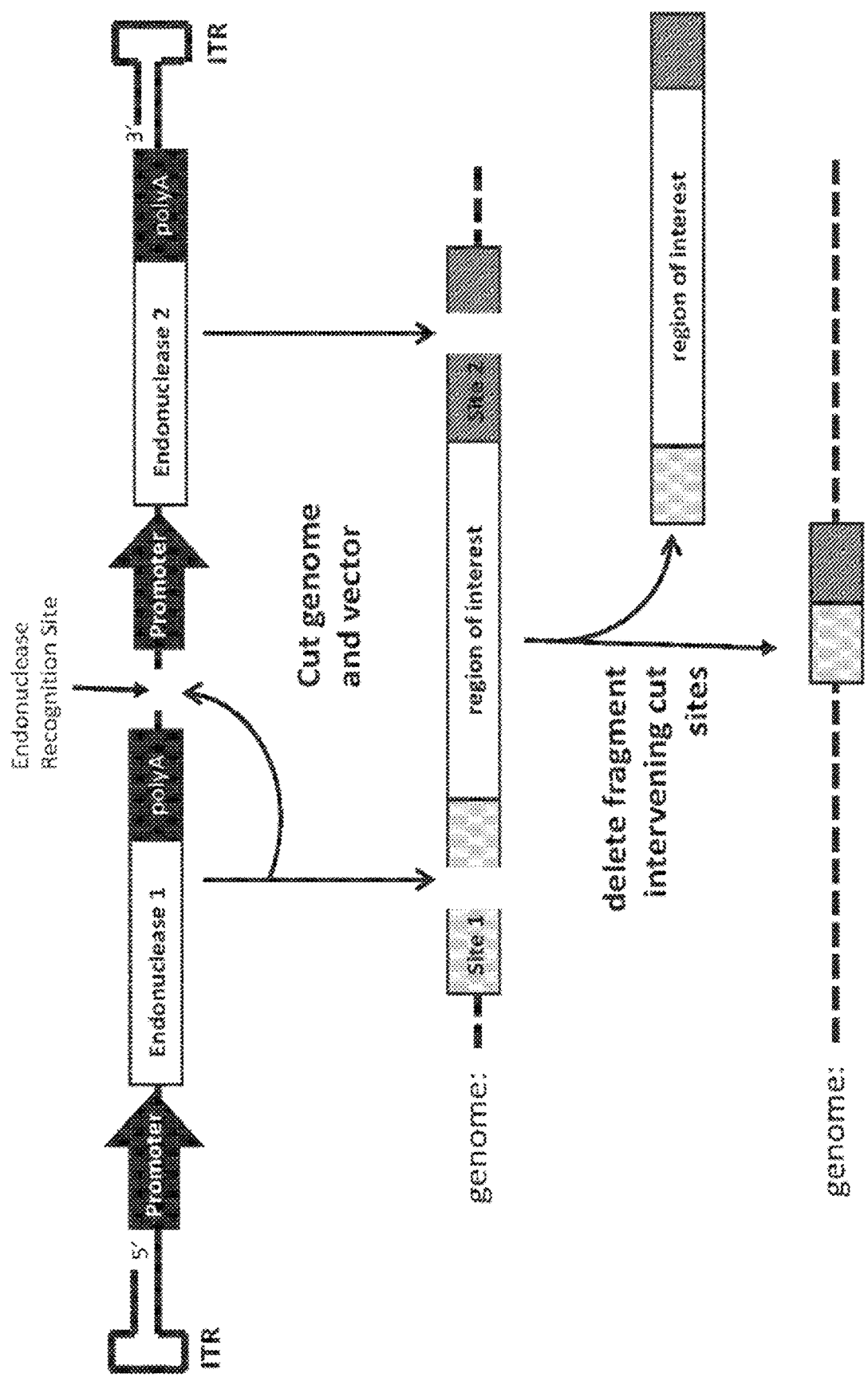
FIG. 3. General method for using a self-limiting rAAV to deliver a pair of endonucleases and excise a specific DNA fragment from the genome. In this embodiment, a self-limiting viral vector is delivered to a cell or organism, the vector encoding a pair of site-specific endonucleases that recognize different target sequences in a locus of interest. Following infection with the vector, the cell or organism expresses the endonucleases. The endonucleases then cut both of the recognition sites in the genome of the cell as well as a recognition site in the genome of the virus. The DNA breaks in the cell genome are repaired by deleting the fragment intervening the breaks, followed by subsequent re-ligation of the genomic ends. The cut virus is quickly degraded by exonucleases and ceases to persist in the cell or organism.

In other embodiments, described in FIG. 3, the self-limiting viral vector comprises, starting at a 5' position between the ITRs, a promoter, a first endonuclease coding sequence and polyA, an endonuclease recognitions site, a second promoter (which may be the same as the first), a second endonuclease with polyA followed by the 3' ITR. Notably, this configuration may be altered, specifically the location of the endonuclease recognition site (as discussed above and exemplified in FIG. 1). The endonuclease recognition site may be recognized by any one of the endonucleases coded for within the self-limiting viral vector. FIG. 3 shows the endonuclease recognition site as being recognized by the first endonuclease. Moreover, it is contemplated that more than two endonucleases, each recognizing a unique site within a cell genome, may be housed within the self-limiting viral vector. FIG. 3 depicts a vector coding for two endonucleases, which when expressed within an infected cell, will each recognize their own target site, where the first endonuclease recognizes a "site 1" and the second endonuclease recognizes a "site 2." The endonucleases cut the genome at each site, exposing the region of interest coded between each cut site. The region of interest fragment is excised and degraded by cell machinery, and the cell genome is repaired by re-ligation. As stated above, the ligation of the genome is achieved by cell processes that maintain the integrity of the sequence and does not introduce additional sequence to the genome. The endonuclease subsequently recognizes the endonuclease recognition site within the self-limiting viral vector and cuts the viral genome. Once cut, the self-limiting viral vector cannot produce concatamers that may otherwise form and persist within the episomes. The self-limiting viral vector will cease to persist within the cell.

The self-limiting viral vectors of the present invention may be employed to introduce a new transgene into the infected cell's genome. In these embodiments, the self-limiting viral vector comprises from a 5' position between the ITRs: a promoter, endonuclease coding sequence and polyA, an endonuclease recognition site, a homologous DNA sequence, the transgene, and another homologous sequence at the 3' position within the ITRs. Notably, this configuration may be altered, specifically the location of the endonuclease recognition site (as discussed above and exemplified in FIG. 1). For example, the endonuclease site could be positioned on the 3' end of the homologous DNA sequence of the transgene, or in an intron contained within the transgene sequence. After infection, the endonuclease is expressed within the cell, and recognizes a site within a region of interest. The endonuclease cleaves a site within the gene of interest, exposing 5' and 3' ends of the cell genome. The self-limiting viral vector contains matching homologous DNA for the exposed 5' and 3' ends of the cleaved cell genome. By homologous recombination, the homologous DNA regions flanking the 5' and 3' ends of the transgene recombine with the cleaved portion of the cell genome and the transgene of the self-limiting viral vector is inserted within the cell genome. The endonuclease subsequently recognizes the endonuclease recognition site within the self-limiting viral vector and cuts the viral genome. Once cut, the self-limiting viral vector cannot produce concameters that may otherwise form and persist within the episomes. The self-limiting viral vector will cease to persist within the cell.

Figure 5:
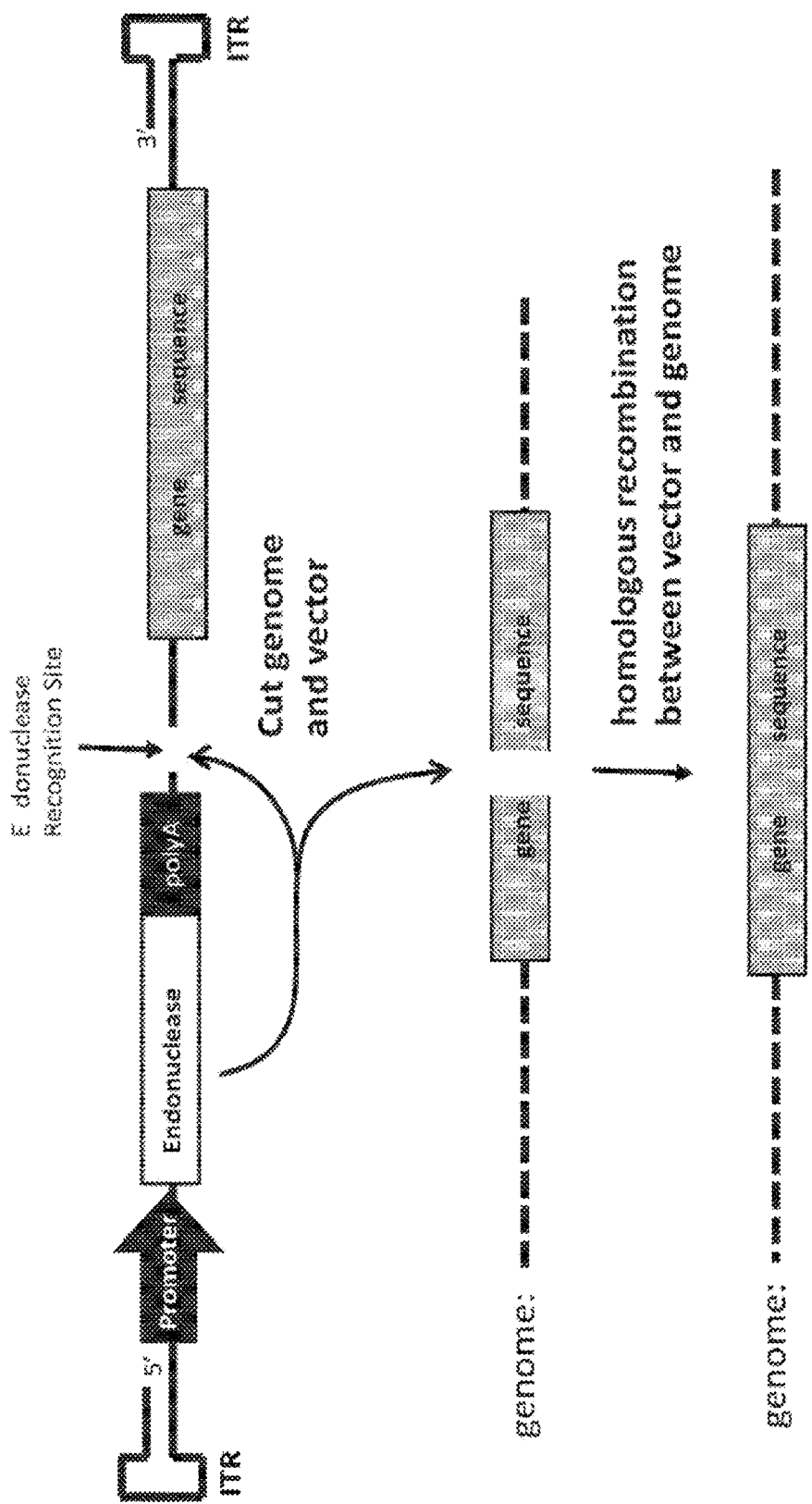
FIG. 5. General method for using a self-limiting rAAV to repair a mutation in the genome of a cell or organism. In this embodiment, a self-limiting viral vector is delivered to a cell or organism, the vector encoding a site-specific endonuclease that recognizes a target sequence in the genome of the cell near a mutation associated with disease. The self-limiting viral vector further comprises a partial "corrected" copy of the mutated gene. Following infection with the vector, the cell expresses the endonuclease. The endonucleases then cuts both the recognition site in the genome of the cell as well as the recognition site in the genome of the virus. The DNA break in the cell genome is repaired by homologous recombination with the viral vector, resulting in the "corrected" sequence being acquired by the genome of the cell. The cut virus is quickly degraded by exonucleases and ceases to persist in the cell or organism.

As shown in FIG. 5, the self-limiting viral vectors of the present invention may be dispatched to alter a gene sequence within a cell genome (as previously defined, that cell being part of a cell line, tissue, or organism). In these embodiments, the self-limiting viral vector comprises at a 5' position of the ITRs, a promoter, an endonuclease coding sequence with polyA, an endonuclease recognition site, a gene sequence and the 3' position within the ITRs. The expressed endonuclease recognizes and cuts a site within the gene sequence in the infected cell's genome. This cut exposes 5' and 3' ends of the infected cell's genome that can recombine with the 5' and 3' ends of the gene sequence encoded within the self-limiting viral vector. The gene sequence is inserted into the infected cell's genome through homologous recombination. The endonuclease subsequently recognizes the endonuclease recognition site within the self-limiting viral vector and cuts the viral genome. Once cut, the self-limiting viral vector cannot produce concameters that may otherwise form and persist within the episomes. The self-limiting viral vector will cease to persist within the cell 2.2 Kinetic Balancing In some cases, it may be advantageous to modify the recognition sequence in the self-limiting viral vector to make it sub-optimal. The viral vector should not be cut before a sufficient concentration of endonuclease has been accumulated in the cell to modify the cell's genome in the desired manner. Because the chromosomal target sequence of interest will be chromatainized, it is more difficult to access than an episomal vector sequence. Thus, higher concentrations of endonuclease are likely required to cut the chromosomal recognition site in the genome of the cell. If the transcribed endonuclease attacks the recognition sequence in the self-limiting viral vector before the appropriate amount of endonuclease is achieved, recognition of the target site within the cell may be unrealized. The use of sub-optimal recognition sequences in the viral vector is "kinetic balancing," because it is done to coordinate the timing of DNA cleavage such that the genome of the cell is cut first, followed by the genome of the virus.

In general, sub-optimal recognition sequences can be generated by deviating from the sequence that the endonuclease was engineered to recognize. An engineered meganuclease, for example, recognizes a 22 bp sequence but will tolerate certain 1-2 basepair changes in its preferred sequence. These modified sequences are typically cut less efficiently than the preferred sequence and, so, are suitable for incorporation into self-limiting viral vectors. In selecting a sub-optimal recognition sequence for incorporation into self-limiting viral vectors, it is critical that the sub-optimal site is still cut by the nuclease, albeit less efficiently than the preferred sequence. For each of the engineered endonuclease types, regions of a recognition sequence may be able to tolerate changes. For example, engineered meganucleases tolerate single-base changes at bases 1, 10, 11, 12, 13, and 22 of the recognition sequence (Jurica M S, Monnat R J Jr, Stoddard B L (1998) *Mol. Cell.* 2(4): 469-76).

Experimental methods to evaluate and quantify site-specific DNA cleavage may be performed, including in vitro DNA digests with purified endonuclease protein and cell-based reporter assays (Chevalier B, Turmel M, Lemieux C, Monnat R J Jr, Stoddard B L (2003) *J. Mol. Biol.* 329(2): 253-69). These methods can be used to evaluate a variety of sub-optimal recognition sequences to determine the sequences that are cut less efficiently than the preferred recognition sequence in the genome of the cell.

2.3 Methods for Producing Self-Limiting Viruses rAAV virus is typically produced in mammalian cell lines such as HEK-293. Because the viral cap and rep genes are removed from the vector to prevent its self-replication to make room for the therapeutic gene(s) to be delivered (e.g. the endonuclease gene), it is necessary to provide these in trans in the packaging cell line. In addition, it is necessary to provide the "helper" (e.g. adenoviral) components necessary to support replication (Cots D, Bosch A, Chillon M (2013) *Curr. Gene Ther.* 13(5): 370-81). Frequently, rAAV is produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because rAAV particles are typically produced (manufactured) in cells, precautions must be taken in practicing the current invention to ensure that the site-specific endonuclease is NOT expressed in the packaging cells. Because the viral genomes of the invention comprise a recognition sequence for the endonuclease, any endonuclease expressed in the packaging cell line will be capable of cleaving the viral genome before it can be packaged into viral particles. This will result in reduced packaging efficiency and/or the packaging of fragmented genomes. Several approaches can be used to prevent endonuclease expression in the packaging cells, including:

1. The endonuclease can be placed under the control of a tissue-specific promoter that is not active in the packaging cells. For example, if a self-limiting viral vector is developed for delivery of (an) endonuclease gene(s) to muscle tissue, a muscle-specific promoter can be used. Examples of muscle-specific promoters include C5-12 (Liu, et al. (2004) *Hum Gene Ther.* 15:783-92), the muscle-specific creatine kinase (MCK) promoter (Yuasa, et al. (2002) *Gene Ther.* 9:1576-88), or the smooth muscle 22 (SM22) promoter (Haase, et al. (2013) *BMC Biotechnol.* 13:49-54). Examples of CNS (neuron)-specific promoters include the NSE, Synapsin, and MeCP2 promoters (Lentz, et al. (2012) *Neurobiol Dis.* 48:179-88). Examples of liver-specific promoters include albumin promoters (such as Palb), human α1-antitrypsin (such as PalAT), and hemopexin (such as Phpx) (Kramer, M G et al., (2003) *Mol. Therapy* 7:375-85). Examples of eye-specific promoters include opsin, and corneal epithelium-specific K12 promoters (Martin K R G, Klein R L, and Quigley H A (2002) *Methods* (28): 267-75) (Tong Y, et al., (2007) *J Gene Med,* 9:956-66). These promoters, or other tissue-specific promoters known in the art, are not highly-active in HEK-293 cells and, thus, will not expected to yield significant levels of endonuclease gene expression in packaging cells when incorporated into self-limiting viral vectors of the present invention. Similarly, the self-limiting viral vectors of the present invention contemplate the use of other cell lines with the use of incompatible tissue specific promoters (i.e., the HeLa cell line (human epithelial cell) and using the liver-specific hemopexin promoter). Other examples of tissue specific promoters include: synovial sarcomas PDZD4 (cerebellum), C6 (liver), ASBS (muscle), PPP1R12B (heart), SLC5A12 (kidney), cholesterol regulation APOM (liver), ADPRHL1 (heart), and monogenic malformation syndromes TP73L (muscle). (Jacox E, et al., (2010) *PLoS One* v.5(8):e12274).

2. Alternatively, the vector can be packaged in cells from a different species in which the endonuclease is not likely to be expressed. For example, viral particles can be produced in microbial, insect, or plant cells using mammalian promoters, such as the cytomegalovirus- or SV40 virus-early promoters, which are not active in the non-mammalian packaging cells. In a preferred embodiment, viral particles are produced in insect cells using the baculovirus system as described by Gao, et al. (Gao, H., et al. (2007) *J. Biotechnol.* 131(2):138-43). An endonuclease under the control of a mammalian promoter is unlikely to be expressed in these cells (Airenne, K J, et al. (2013) *Mol. Ther.* 21(4):739-49). Moreover, insect cells utilize different mRNA splicing motifs than mammalian cells. Thus, it is possible to incorporate a mammalian intron, such as the human growth hormone (HGH) intron (SEQ ID NO: 2), or the SV40 large T antigen intron (SEQ ID NO:3), into the coding sequence of an endonuclease (see, for example, FIG. 1C). Because these introns are not spliced efficiently from pre-mRNA transcripts in insect cells, insect cells will not express a functional endonuclease and will package the full-length genome. In contrast, mammalian cells to which the resulting rAAV particles are delivered will properly splice the pre-mRNA and will express functional endonuclease protein. Haifeng Chen has reported the use of the HGH and SV40 large T antigen introns to attenuate expression of the toxic proteins barnase and diphtheria toxin fragment A in insect packaging cells, enabling the production of rAAV vectors carrying these toxin genes (Chen, H (2012) *Mol Ther Nucleic Acids.* 1(11): e57).

3. The endonuclease gene can be operably linked to an inducible promoter such that a small-molecule inducer is required for endonuclease expression. Examples of inducible promoters include the Tet-On system (Clontech; Chen H., et al., (2015) *BMC Biotechnol.* 15(1):4)) and the RheoSwitch system (Intrexon; Sowa G., et al., (2011) *Spine,* 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the endonuclease gene under the control of a promoter that responds to the corresponding transcription factor, the endonuclease gene having (a) binding site(s) for the transcription factor; and 2) including the gene encoding the transcription factor in the packaged viral genome. The latter step is necessary because the endonuclease will not be expressed in the target cells or tissues following rAAV delivery if the transcription activator is not also provided to the same cells. The transcription activator then induces endonuclease gene expression only in cells or tissues that are treated with the cognate small-molecule activator. This approach is advantageous because it enables endonuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

4. In another preferred embodiment, rAAV particles are produced in a mammalian cell line that expresses a transcription repressor that prevents expression of the endonuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the endonuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or, most preferably, it can be stably integrated into the genome of the packaging cell such that it is expressed constitutively. Some methods to modify common mammalian promoters to incorporate transcription repressor sites have been disclosed in the art. For example, Chang and Roninson modified the strong, constitutive CMV and RSV promoters to comprise operators for the Lac repressor and showed that gene expression from the modified promoters was greatly attenuated in cells expressing the repressor (Chang B D, and Roninson I B (1996) *Gene* 183:137-42). The use of a non-human transcription repressor ensures that transcription of the endonuclease gene will be repressed only in the packaging cells expressing the repressor and not in target cells or tissues transduced with the resulting self-limiting rAAV vector.

2.4 Methods for Delivering Self-Limiting Viral Vectors to Human Patients and Animals The self-limiting viral vectors of the invention, with their significant safety advantages relative to conventional gene-therapy vectors, will be used as therapeutic agents for the treatment of genetic disorders. For therapeutic applications, route of administration is an important consideration. These self-limiting viral vectors may be delivered systemically via intravenous injection, especially where the target tissues for the therapeutic are liver (e.g. hepatocytes) or vascular epithelium/endothelium. Alternatively, the self-limiting viral vectors of the invention may be injected directly into target tissues. For example, rAAV can be delivered to muscle cells via intramuscular injection (Maltzahn, et al. (2012) *Proc Natl Acad Sci USA.* 109:20614-9), or hydrodynamic injection (Taniyama, et al. (2012) *Curr Top Med Chem.* 12:1630-7 and Hegge, et al. (2010) *Hum Gene Ther.* 21:829-42). Delivery to CNS can be accomplished by systemic delivery or intracranial injection (Weinberg, et al. (2013) *Neuropharmacology.* 69:82-8, Bourdenx, et al. (2014) *Front Mol Neurosci.*7:50, and Ojala D S, et al. (2015) *Neuroscientist.* 21(1):84-98). Direct injection (e.g. subretinal injection) is the preferred route of administration for the eye (Willett K and Bennett J (2013) *Front Immunol.* 4:261 and Colella P and Auricchio A (2012) *Hum Gene Ther.* 23(8): 796-807.)

2.5 Self-Limiting Adenoviral and Retroviral Vectors

Figure 4:
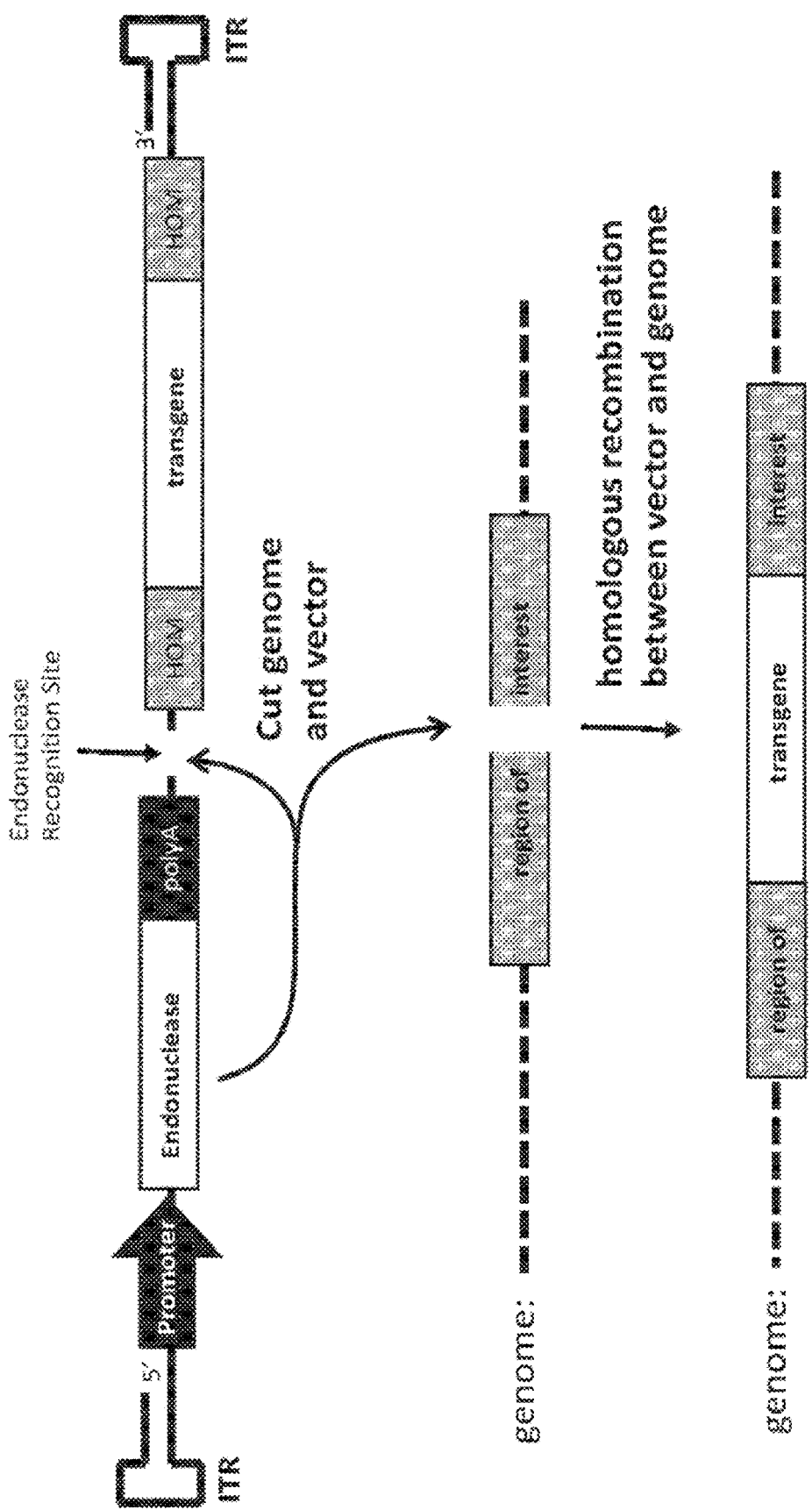
FIG. 4. General method for using a self-limiting rAAV to insert a transgene at a defined location within the genome of a cell. In this embodiment, a self-limiting viral vector is delivered to a cell or organism, the vector encoding a site-specific endonuclease that recognizes a target sequence in a locus of interest within the cell or organism's genome. The self-limiting viral vector contains a transgene flanked by a DNA sequence homologous to the locus of interest. Following infection with the vector, the cell expresses the endonuclease. The endonucleases then cuts both the recognition site in the genome of the cell, as well as the recognition site in the genome of the virus. The DNA break in the cell genome is repaired by homologous recombination with the viral vector, resulting in the insertion of the transgene at the site of the DNA break. The cut virus is quickly degraded by exonucleases and ceases to persist in the cell or organism.

While the preferred embodiments of the invention are self-limiting rAAV vectors, the same principles can be applied to adenoviral and lentiviral/retroviral vectors to limit the persistence times of these vectors in cells. These viral vectors have significantly larger genomes and, hence, larger "carrying capacities" than AAV which makes them preferable for the delivery of larger gene payloads to the cell. Indeed, for applications involving the use of a gene editing endonuclease to insert a transgene into the genome (as in FIG. 4), adenoviral or lentiviral/retroviral vectors are preferred when the transgene is larger than ~3.5 kb. For other applications (e.g. FIGS. 2, 3, and 5) adenoviral or lentiviral/retroviral vectors are preferred when the gene editing endonuclease is too large to be encoded by rAAV. This is particularly applicable when employing TALENs and most CRISPR/Cas9 endonucleases.

Adenovirus and lentiviruses/retroviruses naturally integrate into the genome of the host cell. To be useful for the present invention, the ability of the virus to integrate into the genome must be attenuated. For lentiviral/retroviral vectors, this is accomplished by mutating the int gene encoding the virus integrase. For example, Bobis-Wozowicz, et al. used an integration-deficient retroviral vector to deliver zinc-finger nucleases to human and mouse cells (Bobis-Wozowicz, et al (2014) *Nature Scientific Reports* 4:4656) (Qasim W, Vink C A, Thrasher A J (2010) *Mol. Ther.* 18(7):1263-67), (Wanisch K, Yáñez-Muñoz R J (2009) *Mol. Ther.* 17(8):1316-32), (Nowrouzi A, et al. (2011) *Viruses* 3(5):429-55).

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Promoter Silencing in Viral Packaging Cells

1. Rationale

In one example of the self-limiting system described herein, a nuclease is expressed from its gene on a viral vector. The nuclease then recognizes and cleaves a recognition sequence integrated within the viral vector at any number of positions. In some examples, the recognition sequence can be positioned within an intron that is integrated into the nuclease gene sequence. As a result, the viral vector is cleaved and degraded by the cell in a self-limiting manner.

A major obstacle to utilizing this concept to produce a packaged virus, such an as AAV virus, is preventing the nuclease from being expressed in the packaging cell line during the production of the viral vector. If expressed in the packaging cell line, the nuclease could prematurely cut the viral vectors, as well as the plasmid DNA encoding the viral vectors, preventing packaging of whole, intact genomes that contain an intact meganuclease gene. Thus, one goal of the present studies was to determine strategies for turning off expression of the nuclease in the packaging cell line, but allowing the nuclease to be expressed in cells transfected with the self-limiting virus.

2. Recombinant DNA Plasmids Comprising a Lac Repressor

In one approach, recombinant DNA plasmids were produced which comprised a Lac operator-repressor system. As reported by Cronin et al., three Lac operators within a mammalian promoter can inhibit transcription by binding Lac repressor and inhibiting RNA polymerase from processing through (Cronin, C. A., Gluba, W., and Scrable, H. (2001) *Genes Dev.* 15(12): 1506-1517). It was reasoned that placing three Lac operators between a CMV promoter and a nuclease gene would allow similar inhibition of expression in the presence of a Lac repressor.

Figure 6A:
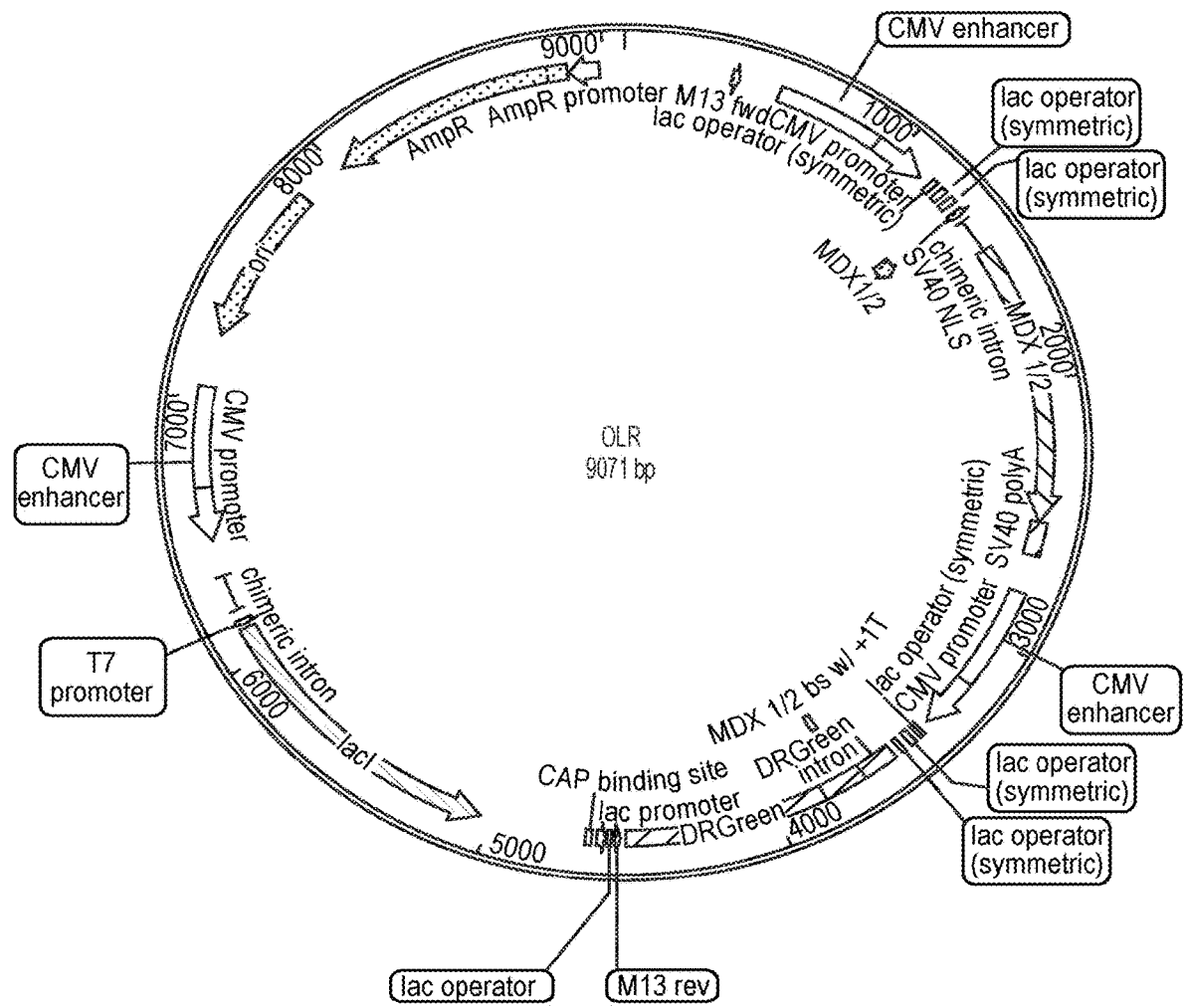
FIG. 6A-6B.

Thus, a DNA plasmid was produced which comprised a CMV promoter operably-linked to a nuclease gene encoding a meganuclease referred to as MDX 1/2. This plasmid, referred to herein as the OLR plasmid, is illustrated in FIG. 6A, and its nucleic acid sequence is set forth in SEQ ID NO: 4. As shown, the CMV promoter was modified to include three Lac operators. The naturally-occurring Lac operator sequences were substituted with ideal operator sequences because the Lac repressor binds more tightly to the ideal operator and, hence, should cause stronger resistance to the RNA polymerase and better repression. Further, a mammalian expression cassette was built for the Lac repressor consisting of a CMV promoter and SV40 poly A. The Lad gene was not codon-optimized for Lac repressor. The Lac repressor expression cassette was integrated into the plasmid backbone outside of the viral inverted terminal repeats (ITRs). This positioning was very important, as it allowed for expression of the Lac repressor in the packaging cell line to prevent expression of the meganuclease, but because the Lac repressor expression cassette is not packaged in the AAV virus, there should be no repression of the meganuclease in the target cells transfected with the AAV virus.

Figure 6B:
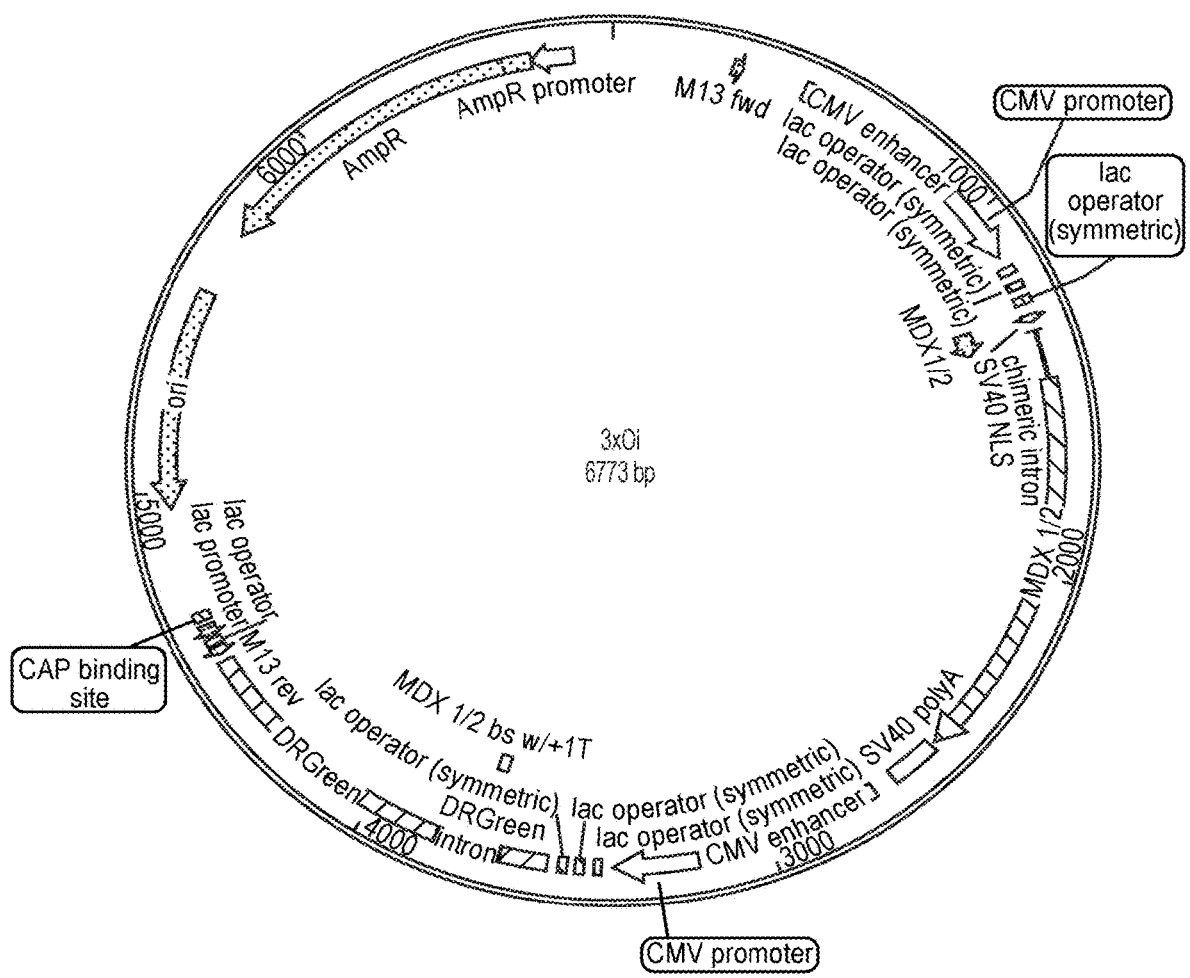

Additionally, a second DNA plasmid was produced which comprised a CMV promoter operably-linked to a nuclease gene encoding the MDX 1/2 meganuclease. This plasmid, referred to herein as the 3×Oi plasmid, is illustrated in FIG. 6B, and its nucleic acid sequence is set forth in SEQ ID NO: 5. As shown, the CMV promoter in the 3×Oi plasmid was also modified to include three Lac operators, but the 3×Oi plasmid did not comprise the Lad cassette to express the Lac repressor. Thus, it was expected that there would be no suppression of meganuclease expression in the viral packaging cells.

3. Nuclease protein expression in HEK293 cells

Experiments were conducted to determine whether nuclease protein expression was suppressed in viral packaging cells by using a Lac repressor. HEK293 cells were mock electroporated, or electroporated with 2 μg of the OLR plasmid, the 3×Oi plasmid, or a GFP (pMAX) RNA using a BioRad Gene Pulser Xcell according to the manufacturer's instructions. At 1, 2, 4, 8, and 24 hours post-transformation, cell lysates were prepared by removing media, washing cells with phosphate buffered saline, adding 150 μL of RIPA buffer, scraping cells from their wells, and freezing lysates at −80° C. Lysates from mock electroporated cells were obtained at 24 hours.

Nuclease protein expression was determined by Western blot analysis. Cell lysates were incubated at −80° C. for 15 minutes, thawed, re-frozen, re-thawed, and then centrifuged for 10 minutes at 16,000×g. Supernatants were collected and protein concentrations were determined by the BCA method in combination with a plate reader. 9 total protein per sample was electrophoresed under reducing conditions on a 12-well 4-12% polyacrylamide gel. Duplicate gels were also run. Proteins were transferred to PVDF membranes and blocked for 3 hours in TBST (0.1%) and 5% milk.

To stain for the meganuclease, one membrane was incubated with a rabbit anti-I-CRE antibody (1:8000) in TBST (0.1%) and 5% milk overnight (~18 hours) at 4° C. The membrane was washed 6 times for 5 minutes in TBST (0.1%). The membrane was then incubated with a peroxidase-labeled goat anti-rabbit antibody at 1:40k in TBST (0.1%) with 5% milk for 60 minutes at room temperature. The membrane was then washed 6 times for 5 minutes in TBST (0.1%) and incubated for 5 minutes in Amersham's ECL Prime Western Blotting Detection Reagent. The membrane was developed on Kodak's BioMax XAR film.

As a control, the second membrane was stained for β-actin. The second membrane was incubated with a monoclonal anti β-actin antibody (1:15,000) in TBST (0.1%) and 5% milk overnight (~18 hrs) at 4° C. The membrane was washed 6 times for 5 minutes in TBST (0.1%). The membrane was then incubated with a peroxidase-labeled goat anti-mouse antibody at 1:40k in TBST (0.1%) with 5% milk for 60 minutes at room temperature. The membrane was then washed 6 times for 5 minutes in TBST (0.1%) and incubated for 5 minutes in Amersham's ECL Prime Western Blotting Detection Reagent. The membrane was developed on Kodak's BioMax XAR film.

Figure 7:
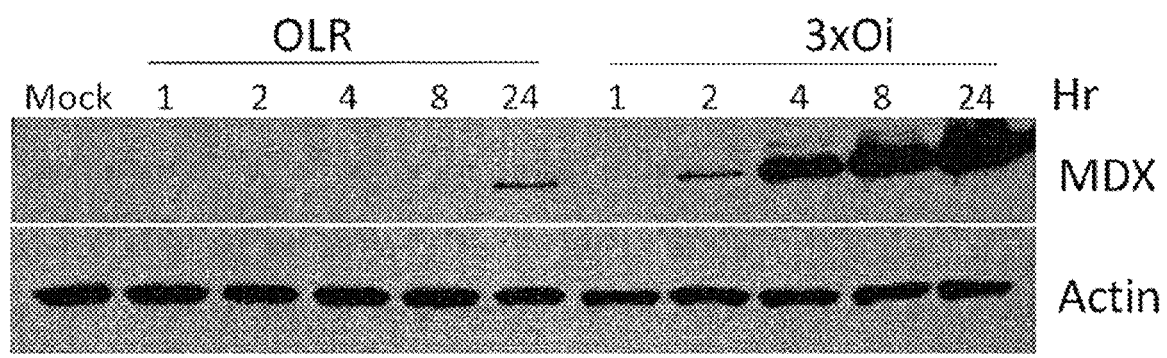
FIG. 7. Western blot for MDX 1/2 meganuclease expression. Experiments were conducted to determine whether nuclease protein expression was suppressed in viral packaging cells by using a Lac repressor. HEK293 cells were mock electroporated, or electroporated with 2 µg of the OLR plasmid, the 3×Oi plasmid, or a GFP (pMAX) RNA. At 1, 2, 4, 8, and 24 hours post-transformation, cell lysates were prepared and nuclease protein expression was determined by Western blot analysis.

The Western blot analysis showed that cells transformed with the 3×Oi plasmid, which did not comprise the Lac repressor sequence, showed an increase in MDX 1/2 protein expression throughout the course of the experiment (FIG. 7). By contrast, expression of MDX 1/2 protein was dramatically suppressed over 24 hours in HEK293 cells transformed with the OLR plasmid encoding the Lac repressor. Indeed, even at 24 hours, only a very small fraction of the MDX 1/2 meganuclease produced by the 3×Oi plasmid can be seen in cells transformed with the OLR plasmid.

4. Conclusion

It is clear from this study that the incorporation of a repressor sequence (such as the Lac repressor) into the DNA plasmid, as well as operators for the repressor in the promoter operably-linked to the nuclease gene, can effectively silence expression of a nuclease in a viral packaging cell line, such as HEK293.

Example 2

Suppression of Nuclease Expression in Viral Packaging Cells Using a Tissue-Specific Promoter 1. Rationale In another example, nuclease expression can be suppressed in viral packaging cells by the use of a tissue-specific promoter that is operably-linked to the nuclease gene. In this approach, the tissue-specific promoter is not active in the viral packaging cell but is active in the target cell into which the viral vector is ultimately transduced.

2. Recombinant DNA Construct with Tissue-specific Promoter

Figure 8:
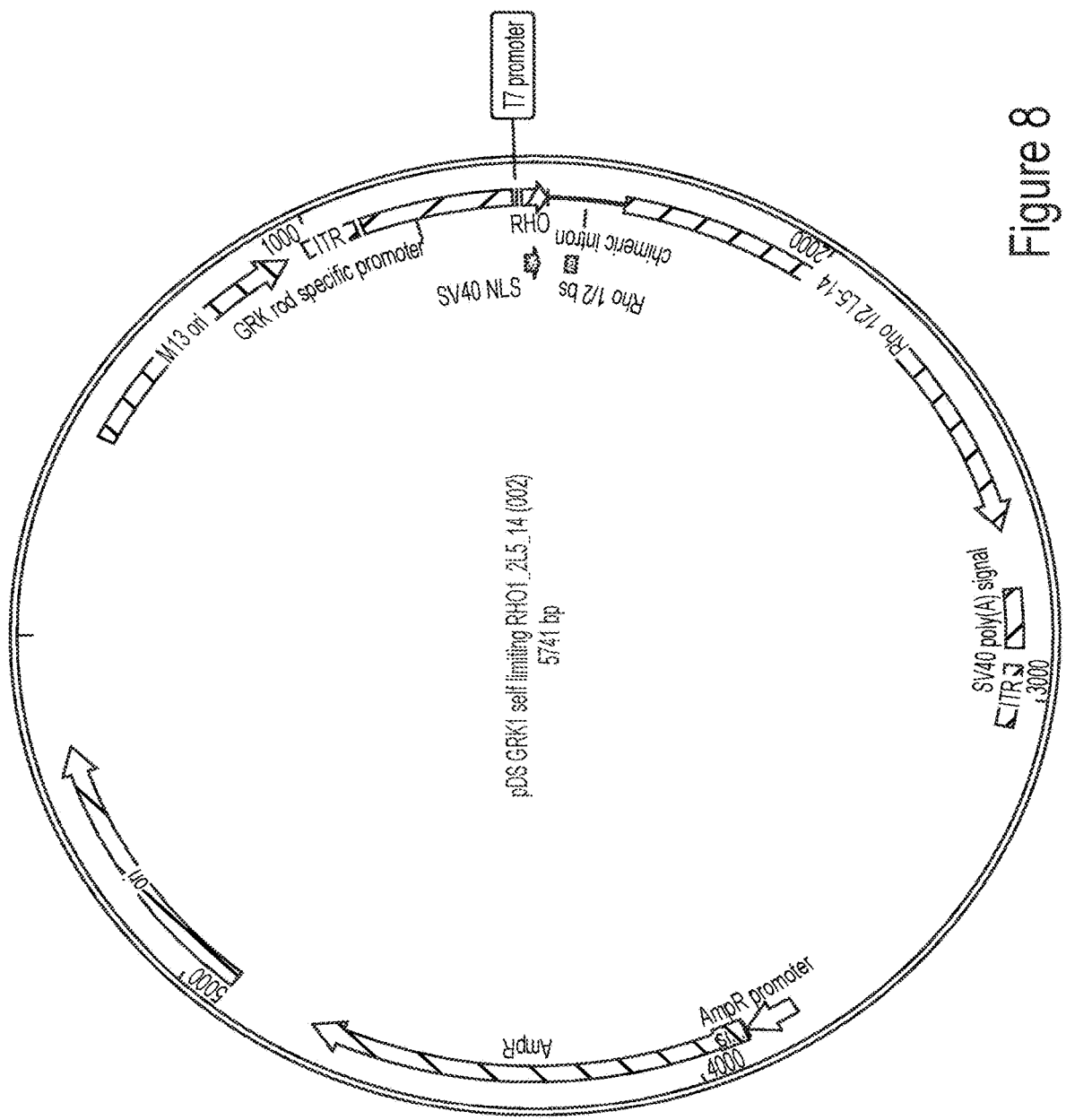
FIG. 8. Vector map for the pDS GRK1 RHO1/2 L5-14 plasmid DNA vector (SEQ ID NO: 6). This vector comprises a RHO 1/2 meganuclease coding sequence that is operably-linked to a GRK1 promoter, which is a tissue-specific promoter that is specifically active in human retinal cells (i.e., rod cells). Thus, the meganuclease gene should not be expressed in viral packaging cells such as HEK293 cells.

In this example, a DNA plasmid, referred to herein as pDS GRK1 RHO1/2 L5-14, was produced which has the nucleotide sequence of SEQ ID NO: 6 (see FIG. 8). This plasmid encodes a RHO 1/2 meganuclease. The RHO 1/2 meganuclease sequence is operably-linked to a GRK1 promoter, which is a tissue-specific promoter that is specifically active in human retinal cells (i.e., rod cells), but not in HEK293 cells used for packaging of viral vectors. Thus, the RHO 1/2 meganuclease will not be expressed in viral packaging cells but will be expressed in retinal cells transduced by the virus. Due to the presence of an intron comprising a recognition sequence for the RHO 1/2 meganuclease, the viral vector will be self-limiting in the retinal cells as the meganuclease is expressed and cleaves the viral genome.

Example 3

Suppression of Nuclease Expression in Insect Viral Packaging Cells Using a Mammalian Intron 1. Rationale In another example, nuclease expression can be suppressed in insect viral packaging cells by the inclusion of a mammalian intron into the nuclease gene. In this approach, the insect packaging cell cannot splice the mammalian intron and, consequently, cannot express the nuclease during packaging of the viral vector. However, mammalian target cells transduced with the viral vectors are capable of splicing the intron and expressing the nuclease, resulting in the degradation of the viral vector in a self-limiting manner.

2. Recombinant DNA Construct

Figure 9A:
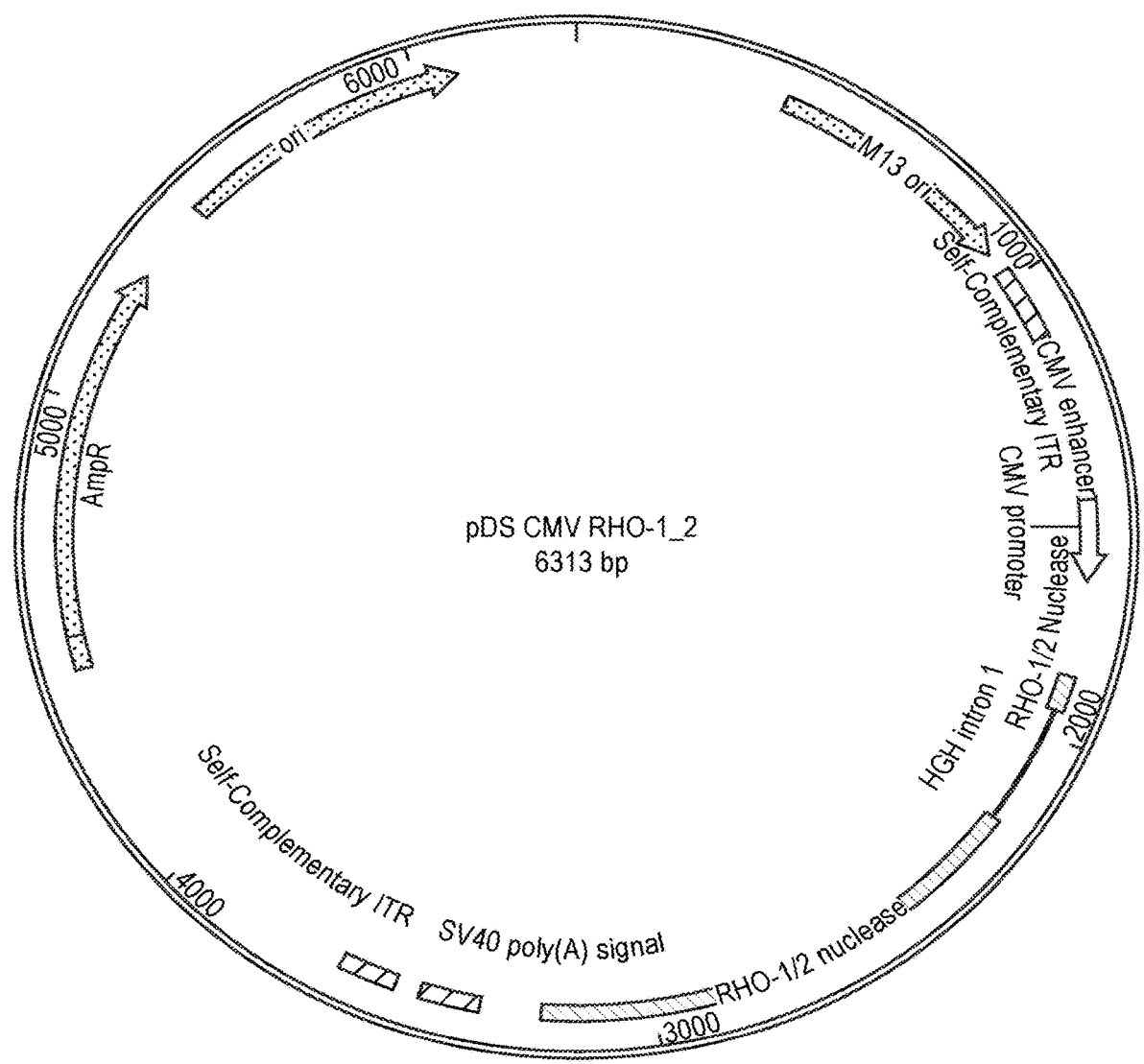
FIG. 9A-9B. Plasmid DNA vectors comprising introns within a nuclease coding sequence.
Figure 9B:
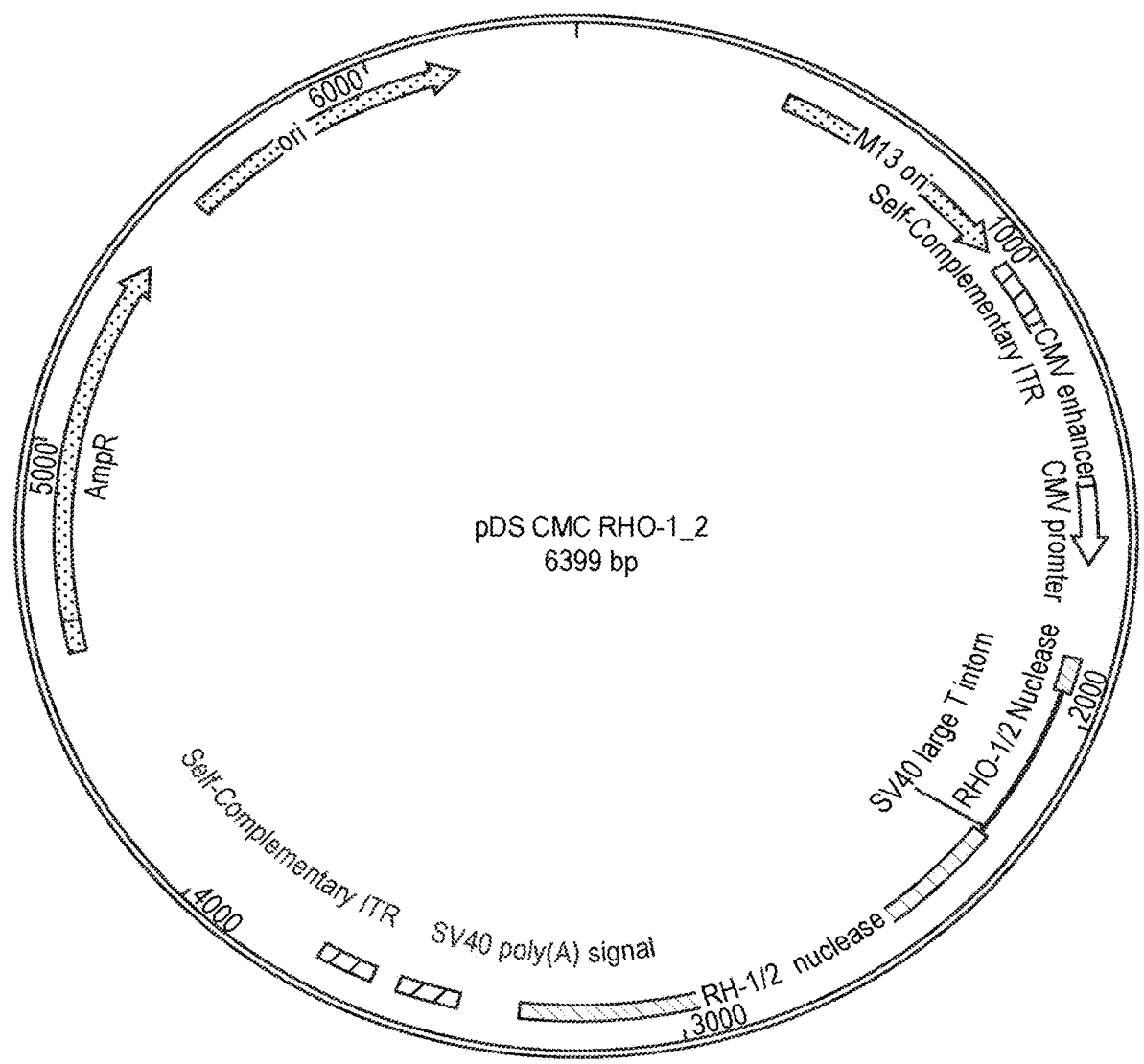

In this example, DNA plasmids were produced which are referred to herein as pDS CMV RHO 1/2-HGH (SEQ ID NO: 7; FIG. 9A) and pDS CMV RHO 1/2-SV40LT (SEQ ID NO: 8; FIG. 9B). Each of these DNA plasmids encodes a RHO 1/2 meganuclease comprising the mammalian human growth hormone intron (SEQ ID NO: 2), or an SV40 large T intron (SEQ ID NO: 3), respectively. Because insect cells utilize different mRNA splicing motifs than mammalian cells, these introns are not spliced efficiently from pre-mRNA transcripts in insect cells. Thus, insect cells will not express a functional nuclease and will package the full-length genome into a viral vector. Therefore, such DNA plasmids are useful for silencing nuclease expression in insect cell expression systems, such as a Baculovirus expression system, and allowing for the production of self-limiting viral vectors of the invention. In contrast, mammalian cells to which the resulting viral vectors are delivered will properly splice the pre-mRNA and will express functional nuclease protein.

Example 4

Promoter Silencing in Viral Packaging Cells Using a Repressor

1. Rationale

Experiments were conducted to further demonstrate that the self-limiting viral vectors of the invention could be successfully generated in viral packaging cells through the use of a transcription repressor or the use of a tissue-specific promoter. It was hypothesized that a higher titer of intact viral vectors could be achieved due to the suppression of nuclease activity and a subsequent lack of cleavage at the nuclease binding site in the viral genome.

2. Transfection of HEK293 viral packaging cells

Figure 10A:
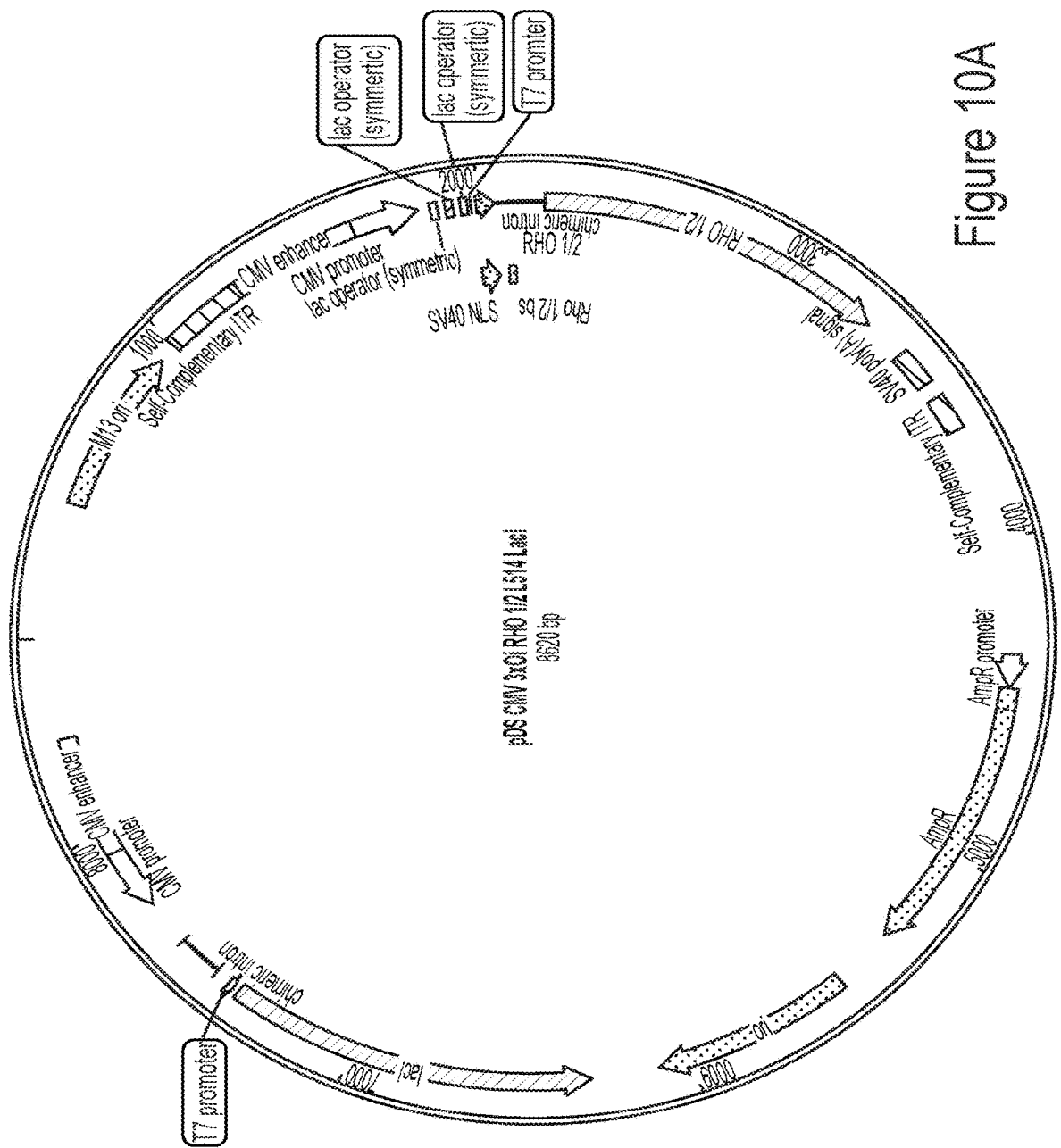
FIGS. 10A-10B.
Figure 10B:
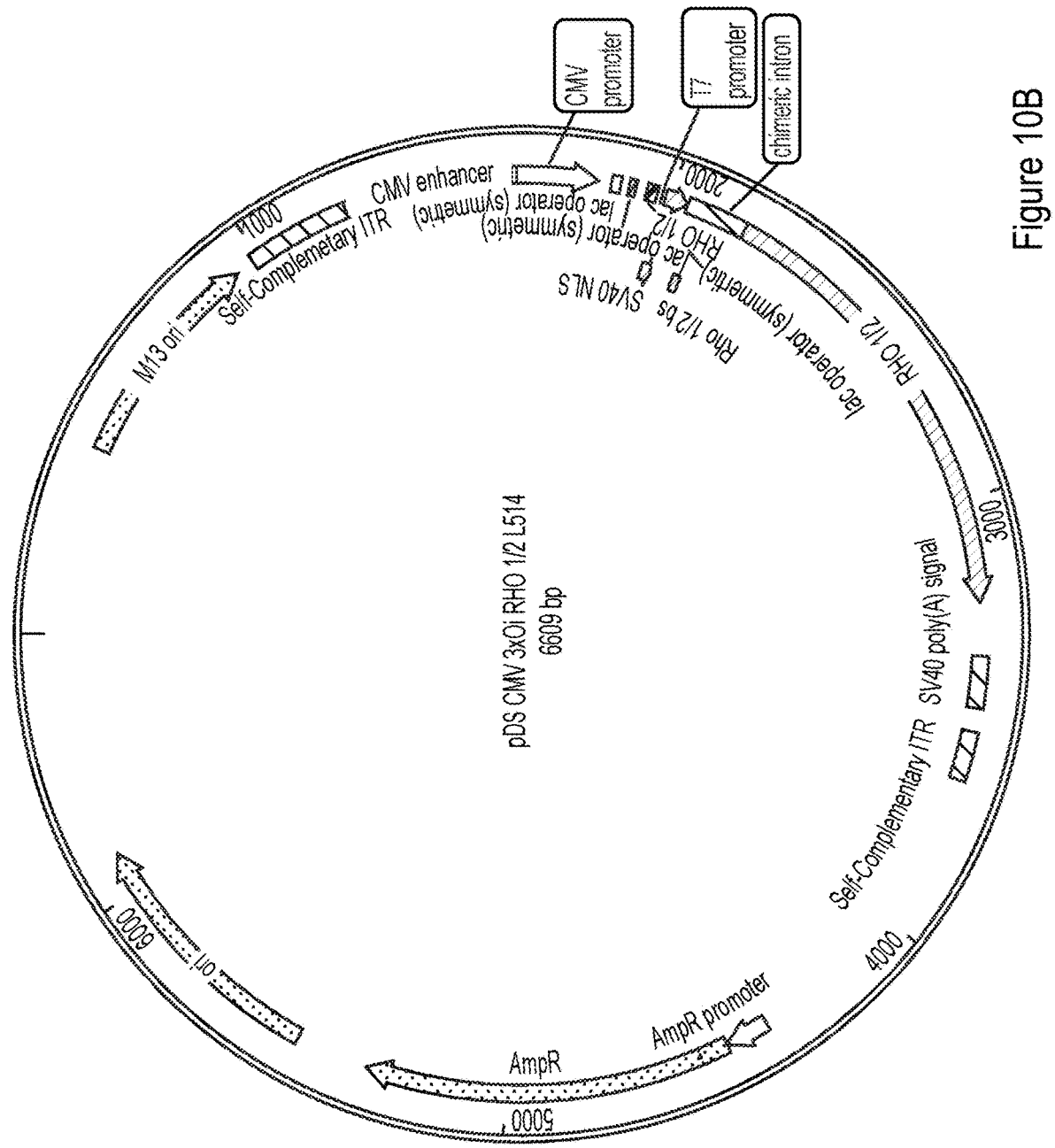

AAV vectors were produced in HEK293 cells using a standard triple transfection protocol. Briefly, the helper plasmid pXX680, the pRepCap2 plasmid encoding the rep and cap proteins, and a plasmid containing the intended vector genome flanked by AAV2 inverted terminal repeats were used for cell transfection according to standard protocols. A first group was transformed with the pDS CMV 3×Oi RHO 1/2 L514 LacI plasmid DNA vector (SEQ ID NO: 9), illustrated in FIG. 10A, which comprises an intron containing a RHO 1/2 binding site, three Lac operators in the CMV promoter, and a LacI coding sequence for a Lac repressor. A second group was transformed with the pDS CMV 3×Oi RHO 1/2 L514 plasmid DNA vector (SEQ ID NO: 10), illustrated in FIG. 10B, which comprises an intron containing a RHO 1/2 binding site, three Lac operators in the CMV promoter, but lacks a LacI coding sequence. A third group was transformed with the pDS GRK1 RHO1/2 L5-14 plasmid DNA vector (SEQ ID NO: 6), illustrated in FIG. 8, which comprises an intron containing a RHO 1/2 binding site and a tissue-specific GRK1 promoter that is specifically active in retinal cells (i.e., rod cells). Viral vectors were harvested from cell lysates after 72 hours in culture. Cesium chloride gradient centrifugation was used to purify AAV vectors from the lysate, which were then dialyzed in 1×PBS, aliquoted, and stored at −80° C.

3. AAV Vector Titers

Vector genome copy number (vg) produced in each group was determined by Southern dot blot analysis using standard protocols. Results are summarized in Table 1.

TABLE 1

| Virus Name | Titer Value |
| --- | --- |
| pDS CMV 3×Oi RHO 1/2 L514 | 2.40E+07 |
| pDS CMV 3×Oi RHO 1/2 L514 LacI | 1.10E+08 |
| pDS GRK1 RHO1/2 L5-14 | 8.4E+0.7 |

As shown, the pDS CMV 3×Oi RHO 1/2 L514 vector, which contained no mechanism for suppressing nuclease expression, had a viral titer of $2.4 \times 10^7$ viral particles. By contrast, the pDS CMV 3×Oi RHO 1/2 L514 LacI vector, which expressed a Lac repressor to suppress nuclease expression in the HEK293 packaging cells, had a viral titer of $1.1 \times 10^8$ viral particles, an increase of approximately 450% compared to the pDS CMV 3×Oi RHO 1/2 L5 vector. Further, it was observed that the pDS GRK1 RHO1/2 L5-14 vector having the tissue-specific GRK1 promoter had a viral titer of 8.4×107 viral particles, an increase of approximately 350% compared to the pDS CMV 3×Oi RHO 1/2 L5 vector.

4. Conclusions

It is evident from these experiments that the inclusion of a mechanism to suppress nuclease expression (e.g., the use of a repressor system, a tissue-specific promoter, etc.) allows for a substantial increase in the titer of intact, self-limiting viral vectors of the invention.

Example 5

Transduction of CHO Cells with Self-limiting Viral Vectors

1. Rationale

Experiments were conducted using the viral vectors prepared in Example 4 to demonstrate that they are self-limiting in a mammalian cell line. It was hypothesized that a control vector lacking the nuclease binding site would express and accumulate an encoded meganuclease, whereas the self-limiting viral vector would express and accumulate some meganuclease protein that would ultimately cleave the viral vectors and reduce further nuclease expression.

2. Transduction of Mammalian Cells

CHO cells were either mock transduced, or transduced with the pDS CMV 3×Oi RHO 1/2 L514 LacI vector (a self-limiting vector comprising a RHO 1/2 binding site) or the pDS CMV 3×Oi RHO 1/2 L514 vector (not self-limiting; no binding site). AAV vectors were incubated with CHO cells at 100,000 viral genomes/cells. Protein was collected at time points of 2, 6, 12, 24, 48, and 72 hours using M-Per reagents (Pierce) according to the manufacturer's instructions. For Western analysis, 50 μg of cell lysate was resolved on a 4-12% Bis-Tris gel (Invitrogen) according to the protocol previously described in Example 1 using the anti-I-CreI antibody at a dilution of 1:1000. A separate gel was stained for β-actin as a loading control. Signal detection was assessed by chemiluminescence.

3. Western Analysis

Figure 11:
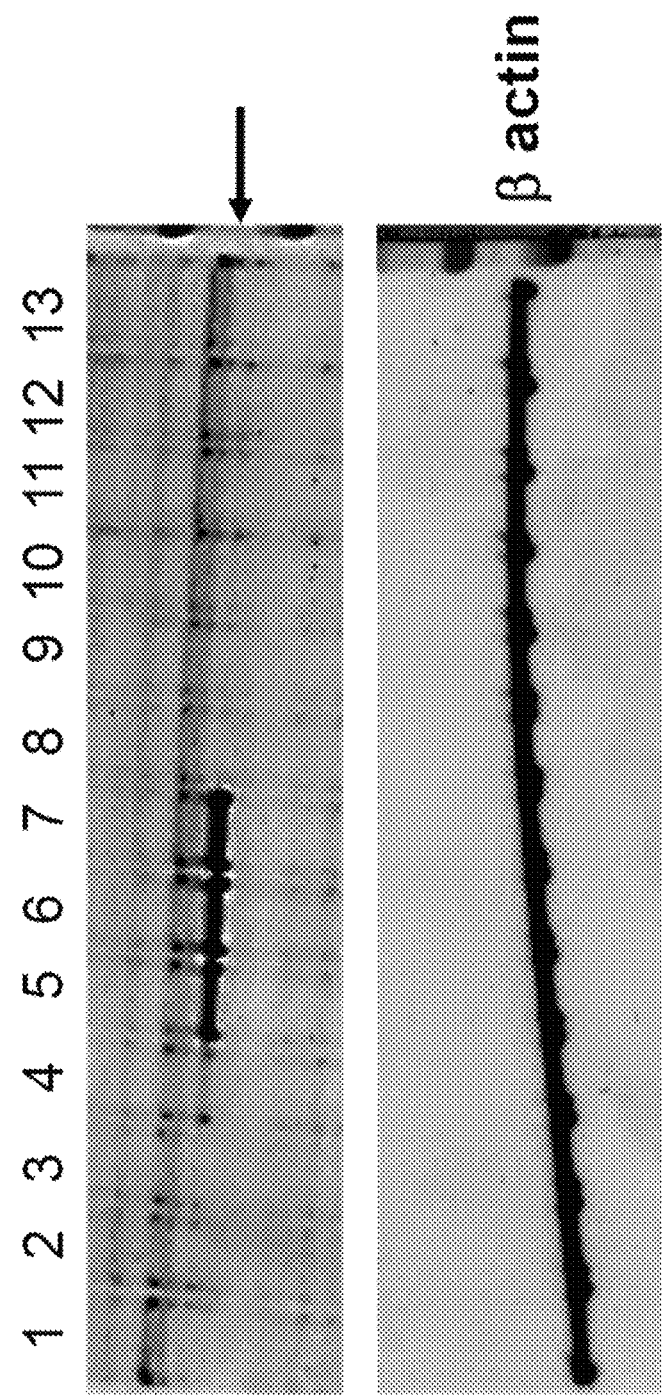
FIG. 11. Western blot analysis of RHO 1/2 meganuclease protein expression in transduced CHO cells. CHO cells were either mock transduced, or transduced with the pDS CMV 3×Oi RHO 1/2 L514 Lad vector (a self-limiting vector comprising a RHO 1/2 binding site) or the pDS CMV 3×Oi RHO 1/2 L514 vector (not self-limiting; no binding site). Protein was collected at time points of 2, 6, 12, 24, 48, and 72 hours and Western analysis was performed to detect RHO 1/2 meganuclease protein in cell lysates. The top panel shows detection of RHO 1/2 meganuclease protein in cell lysates at each time point. Lane 1 shows mock transduced cells. Lanes 2-7 show time points of 2, 6, 12, 24, 48, and 72 hours, respectively, for cells transduced with the pDS CMV 3×Oi RHO 1/2 L514 vector. Lanes 8-13 show time points of 2, 6, 12, 24, 48, and 72 hours, respectively, for cells transduced with the self-limiting pDS CMV 3×Oi RHO 1/2 L514 Lad vector. The arrow indicates the band associated with RHO 1/2 meganuclease protein. The bottom panel shows detection of a β-actin as a loading control.

Western analysis is shown in FIG. 11. The top panel shows detection of RHO 1/2 meganuclease protein in cell lysates at each time point. Lane 1 shows mock transduced cells. Lanes 2-7 show time points of 2, 6, 12, 24, 48, and 72 hours, respectively, for cells transduced with the pDS CMV 3×Oi RHO 1/2 L514 vector. Lanes 8-13 show time points of 2, 6, 12, 24, 48, and 72 hours, respectively, for cells transduced with the self-limiting pDS CMV 3×Oi RHO 1/2 L514 LacI vector. The arrow indicates the band associated with RHO 1/2 meganuclease protein. As shown, the RHO 1/2 meganuclease is expressed and continues to accumulate in CHO cells transduced with the pDS CMV 3×Oi RHO 1/2 L514 vector which is not self-limiting. By contrast, a low level of RHO 1/2 meganuclease expression is detectable by 12 hours in CHO cells transduced with the self-limiting pDS CMV 3×Oi RHO 1/2 L514 LacI vector, but this expression level appears to plateau, presumably because the expressed nuclease recognized and cleaved the binding site in the viral genomes, causing degradation of the viral vectors and preventing further expression of the protein.

4. PCR Analysis of Viral Vector Cleavage

To confirm that the self-limiting viral vectors were cleaved in transduced CHO cells, a PCR protocol was developed that utilizes an adapter protein which ligates to the RHO 1/2 cleavage site of the viral genome.

Briefly, CHO cells were transduced with the self-limiting pDS CMV 3×Oi RHO 1/2 L514 LacI vector as discussed above and DNA was isolated at 2, 6, 12, 24, 48, and 72 hours post-transduction as previously described. An adapter molecule was designed having a 3' overhang that matches the 3' overhang generated in the viral genome by the RHO 1/2 meganuclease. Thus, the adapter would specifically link to the viral genome at a cleaved RHO 1/2 recognition site. 800 ng of DNA was ligated with 2 pmol of adapter at 16° C. overnight. PCR was then performed with 200 ng ligated DNA and a pair of amplification primers, one matching the AAV sequence, and the other matching the adapter molecule sequence. The resulting PCR products were analyzed on gel. In case of AAV digestion by RHO 1/2 and ligation to adapter, a PCR band with size 585 bps was expected to be observed.

5. Results of PCR Analysis

Figure 12:
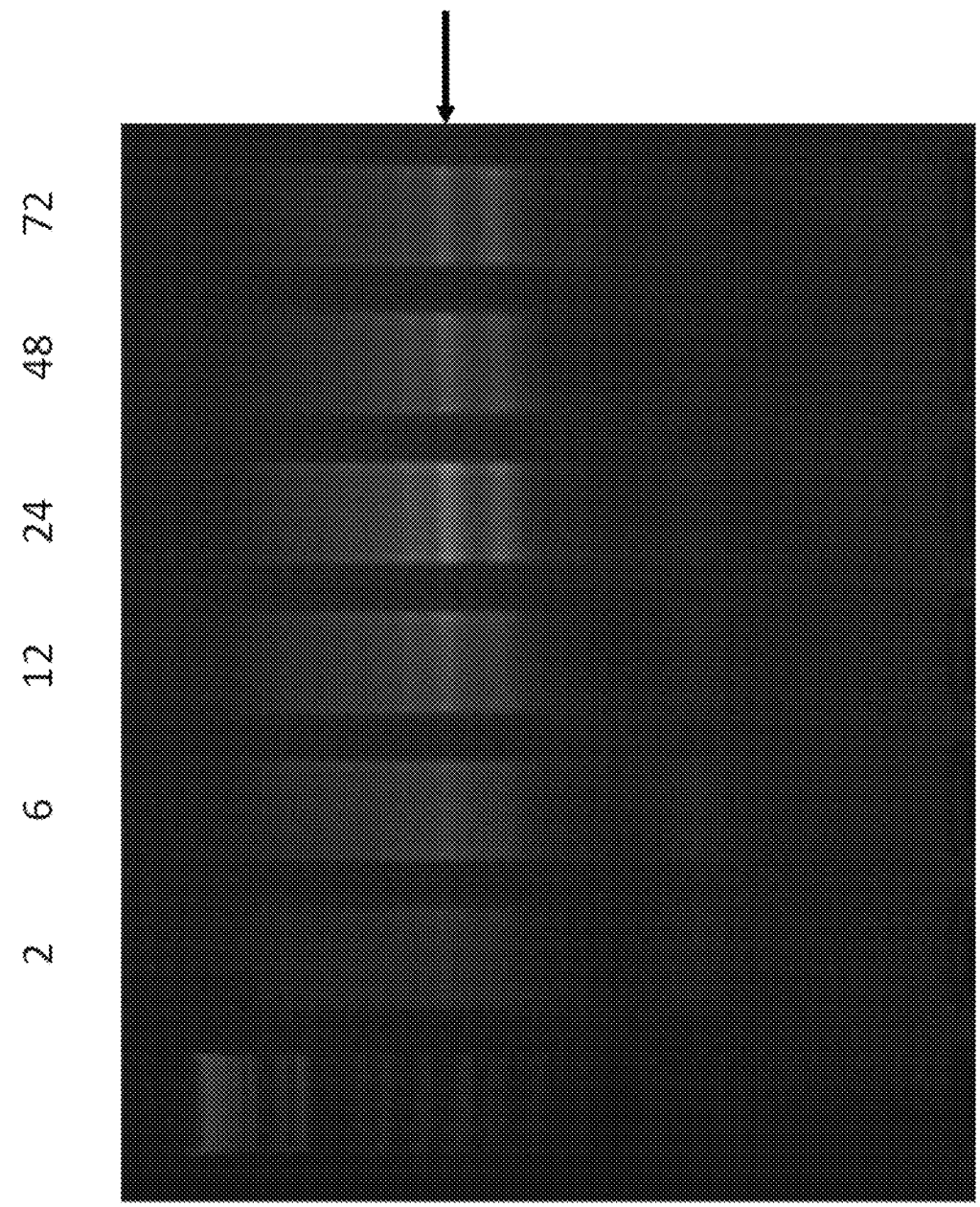
FIG. 12. PCR analysis of viral vector cleavage. CHO cells were transduced with the self-limiting pDS CMV 3×Oi RHO 1/2 L514 Lad vector and DNA was isolated at 2, 6, 12, 24, 48, and 72 hours post-transduction. An adapter molecule was designed having a 3' overhang that matches the 3' overhang generated in the viral genome by the RHO 1/2 meganuclease. PCR was then performed with adapter-ligated DNA and a pair of amplification primers, one matching the AAV sequence, and the other matching the adapter molecule sequence. The resulting PCR products were analyzed on gel. In case of AAV digestion by RHO 1/2 and ligation to adapter, a PCR band with size 585 bps was expected to be observed.

The results of the PCR analysis are shown in FIG. 12 for time points of 2, 26, 12, 24, 48, and 72 hours post-transduction. Bands of ~585 bps corresponding to the correct PCR product are indicated by the arrow. As shown, band intensity significantly increases from the basal level (2 hours) over time, with a maximum signal observed at 24 hours. Band intensity then appears to be reduced at the 48 and 72 hour time points. These PCR results suggest that the self-limiting viral vectors are cleaved by the expressed RHO 1/2 meganuclease in transduced CHO cells.

6. Conclusions

These experiments demonstrated that the persistence time of a self-limiting viral vector of the invention, as measured by nuclease protein expression, is lower in a transduced mammalian cell line than the persistence time of a comparable viral vector that is not self-limiting and does not comprise a nuclease binding site. This is supported by the observation that self-limiting viral vectors are cleaved at the RHO 1/2 recognition sequence within the viral genome.

What is claimed is:

1. A viral vector comprising:

(a) a first nucleic acid sequence encoding a first engineered nuclease and comprising, from 5' to 3', a first exon, an intron, and a second exon;

(b) a first promoter operably linked to said first nucleic acid sequence, wherein said first promoter is positioned 5' upstream of said first nucleic acid sequence and drives expression of said first engineered nuclease in a target cell; and (c) a first vector recognition sequence which is recognized and cleaved by said first engineered nuclease, wherein said first vector recognition sequence is positioned within said intron of said first nucleic acid sequence.

2. The viral vector of claim 1, wherein said viral vector further comprises a first polyA sequence positioned 3' downstream of said first nucleic acid sequence.

3. The viral vector of claim 1, wherein cleavage of said first vector recognition sequence by said first engineered nuclease in said target cell causes said viral vector to have a lower persistence time in said target cell when compared to a viral vector which does not comprise a vector recognition sequence cleaved by said first engineered nuclease but which is otherwise identical.

4. The viral vector of claim 1, wherein said first vector recognition sequence is identical to a first chromosomal recognition sequence present in the genome of said target cell.

5. The viral vector of claim 1, wherein said first vector recognition sequence is a sub-optimal recognition sequence which is recognized and cleaved by said first engineered nuclease.

6. The viral vector of claim 1, wherein said viral vector further comprises a transgene sequence, wherein said transgene sequence is flanked by sequences homologous to sequences flanking a region of interest in the genome of said target cell.

7. The viral vector of claim 6, wherein a first chromosomal recognition sequence is positioned within said region of interest in the genome of said target cell.

8. The viral vector of claim 1, wherein said viral vector further comprises a corrected gene sequence, wherein said corrected gene sequence does not comprise said first vector recognition sequence, and wherein said corrected gene sequence corresponds to a mutated gene sequence present in the genome of said target cell.

9. The viral vector of claim 8, wherein said mutated gene sequence differs from said corrected gene sequence by at least one nucleotide and comprises a first chromosomal recognition sequence.

10. The viral vector of claim 1, wherein said viral vector is an adeno-associated virus (AAV) vector, a retroviral vector, a lentiviral vector, or an adenoviral vector.

11. The viral vector of claim 1, wherein said viral vector is an AAV vector comprising a 5' inverted terminal repeat and a 3' inverted terminal repeat.

12. The viral vector of claim 11, wherein said AAV vector is a single-stranded AAV vector or a self-complementary AAV vector.

13. The viral vector of claim 1, wherein said first promoter is a tissue-specific promoter, a species-specific promoter, or an inducible promoter.

14. The viral vector of claim 1, wherein said engineered nuclease is an engineered meganuclease, a zinc finger nuclease (ZFN), a transcription activator-like effector nuclease (TALEN), a compact transcription activator-like effector nuclease (Compact TALEN), or a clustered regularly interspaced short palindromic repeats (CRISPR)/CRISPR-associated protein (CRISPR/Cas).

15. The viral vector of claim 1, wherein said engineered nuclease is an engineered meganuclease.

16. The viral vector of claim 1, wherein said first promoter comprises one or more binding sites for a transcription repressor that binds to and silences said first promoter.

17. The viral vector of claim 16, wherein said transcription repressor is a Tet repressor, a Lac repressor, a Cre repressor, or a Lambda repressor.

18. A recombinant DNA construct encoding said viral vector of claim 16, wherein said recombinant DNA construct further comprises a nucleic acid sequence encoding said transcription repressor.

19. The viral vector of claim 1, wherein said first promoter is an inducible promoter, and wherein said viral vector further comprises a nucleic acid sequence encoding a ligand-inducible transcription factor which regulates activation of said first promoter.

20. A recombinant DNA construct encoding said viral vector of claim 1.

21. An in vitro method for producing a viral vector, said method comprising:
(a) transforming a packaging cell with said recombinant DNA construct of claim 20;
(b) transforming said packaging cell with a second recombinant DNA construct comprising a cap gene and a rep gene; and
(c) transforming said packaging cell with a third recombinant DNA construct comprising adenoviral helper components;
wherein said packaging cell produces said viral vector.

* * * * *

SEQUENCE LISTING

<160> NUMBER OF SEQ ID NOS: 10

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro

<210> SEQ ID NO 2
<211> LENGTH: 260
<212> TYPE: DNA
<213> ORGANISM: Homo sapiens

<400> SEQUENCE: 2
gtaagcgccc ctaaaatccc tttgggcaca atgtgtcctg aggggagagg cagcgacctg      60
tagatgggac gggggcacta accctcaggt ttggggcttc tgaatgtgag tatcgccatg     120
taagcccagt atttggccaa tctcagaaag ctcctggtcc ctggagggat ggagagagaa     180
aaacaaacag ctcctggagc agggagagtg ctggcctctt gctctccggc tccctctgtt     240
gccctctggt ttctccccag                                                 260

<210> SEQ ID NO 3
<211> LENGTH: 346
<212> TYPE: DNA
<213> ORGANISM: Polyomavirus SV40

<400> SEQUENCE: 3
gtatttgctt cttccttaaa tcctggtgtt gatgcaatgt actgcaaaca atggcctgag      60
tgtgcaaaga aaatgtctgc taactgcata tgcttgctgt gcttactgag atgaagcat     120 gaaaatagaa aattatacag gaaagatcca cttgtgtggg ttgattgcta ctgcttcgat     180
tgctttagaa tgtggtttgg acttgatctt tgtgaaggaa ccttacttct gtggtgtgac     240
ataattggac aaactaccta cagagattta aagctctaag gtaaatataa aattttttaag   300 tgtataatgt gttaaactac tgattctaat tgtttgtgta ttttag                    346

<210> SEQ ID NO 4
<211> LENGTH: 9071
<212> TYPE: DNA
<213> ORGANISM: Artificial Sequence
<220> FEATURE:
<223> OTHER INFORMATION: Synthesized

<400> SEQUENCE: 4

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cagatcttca atattggcca     420
ttagccatat tattcattgg ttatatagca taaatcaata ttggctattg gccattgcat     480
acgttgtatc tatatcataa tatgtacatt tatattggct catgtccaat atgaccgcca     540
tgttggcatt gattattgac tagttattaa tagtaatcaa ttacggggtc attagttcat     600
agcccatata tggagttccg cgttacataa cttacggtaa atggcccgcc tggctgaccg     660
cccaacgacc cccgcccatt gacgtcaata atgacgtatg ttcccatagt aacgccaata     720
gggactttcc attgacgtca atgggtggag tatttacggt aaactgccca cttggcagta     780
catcaagtgt atcatatgcc aagtccgccc cctattgacg tcaatgacgg taaatggccc     840
gcctggcatt atgcccagta catgacctta cgggactttc ctacttggca gtacatctac     900
gtattagtca tcgctattac catgatgatg cggttttggc agtacaccaa tgggcgtgga     960
tagcggtttg actcacgggg atttccaagt ctccacccca ttgacgtcaa tgggagtttg    1020
ttttggcacc aaaatcaacg ggactttcca aaatgtcgta taaccccgc ccgttgacg      1080
caaatgggcg gtaggcgtgt acggtggag tctatataa gcagagctcg tttagtgaac       1140
cgtcagatca ctagaagctt aattgtgagc gctcacaatt gtgagactgc tgccgcagtc    1200
agtaattgtg agcgctcaca attgacctgg agctgcagga gttggtaatt gtgagcgctc    1260
acaattctcg agatatatat ctaggccacc atggcaccga agaagaagcg caaggtgcat    1320
atgaatacaa aatataataa ggtaagtatc aaggttacaa gacaggttta aggcgccaat    1380
agaagcttgg cttgtcgaga cagagaagac tcttgcgttt ctgataggca cctattggtc    1440
ttactgacat ccactttgcc tttctctcca caggagttct tactctactt agcagggttt    1500
gtagacggtg acggttccat ctttgcctgt atccatccta gtcaagcgta taagttcaag    1560
caccggctga ctctccattt cacggtcact cagaagacac agcgccgttg gttcctcgac    1620
aagctggtgg acgagatcgg tgtgggttac gtgcaggacg tgggcagcgt ctcccagtac    1680
cggctgtccc agatcaagcc tttgcataat tttttaacac aactacaacc ttttctaaaa    1740
ctaaaacaaa aacaagcaaa tttagttttta aaaattattg aacaacttcc gtcagcaaaa    1800
gaatccccgg acaaattctt agaagtttgt acatgggtgg atcaaattgc agctctgaat    1860
gattcgaaga cgcgtaaaac aacttctgaa accgttcgtg ctgtgctaga cagtttacca    1920
ggatccgtgg gaggtctatc gccatctcag gcatccagcg ccgcatcctc ggcttcctca    1980
agcccgggtt cagggatctc cgaagcactc agagctggag caggttccgg cactggatac    2040
```

```
aacaaggaat tcctgctcta cctggcgggc ttcgtcgacg gggacggctc catctctgcc    2100
actatcgctc cggctcagta tggtaagttc aagcactatc tggggctccg gttctatgtc    2160
agtcagaaga cacagcgccg ttggttcctc gacaagctgg tggacgagat cggtgtgggt    2220
tacgtgagtg accagggcag cgtctccagg tactgtctgt cccagatcaa gcctctgcac    2280
aacttcctga cccagctcca gcccttcctg aagctcaagc agaagcaggc caacctcgtg    2340
ctgaagatca tcgagcagct gccctccgcc aaggaatccc cggacaagtt cctggaggtg    2400
tgcacctggg tggaccagat cgccgctctg aacgactcca agacccgcaa gaccacttcc    2460
gaaaccgtcc gcgccgttct agacagtctc tccgagaaga agaagtcgtc ccctaaggt    2520 accattcgag cagacatgat aagatacatt gatgagtttg acaaaccac aactagaatg    2580 cagtgaaaaa aatgctttat ttgtgaaatt tgtgatgcta ttgctttatt tgtaaccatt    2640
ataagctgca ataaactagt tcaatattgg ccattagcca tattattcat tggttatata    2700
gcataaatca atattggcta ttggccattg catacgttgt atctatatca taatatgtac    2760
atttatattg gctcatgtcc aatatgaccg ccatgttggc attgattatt gactagttat    2820
taatagtaat caattacggg gtcattagtt catagcccat atatggagtt ccgcgttaca    2880
taacttacgg taaatggccc gcctggctga ccgcccaacg acccccgccc attgacgtca    2940
ataatgacgt atgttcccat agtaacgcca tagggacttt ccattgacg tcaatgggtg    3000 gagtatttac ggtaaactgc ccacttggca gtacatcaag tgtatcatat gccaagtccg    3060 cccccctattg acgtcaatga cggtaaatgg cccgcctggc attatgccca gtacatgacc    3120
ttacgggact ttcctacttg gcagtacatc tacgtattag tcatcgctat taccatgatg    3180
atgcggtttt ggcagtacac caatgggcgt ggatagcggt ttgactcacg ggatttcca    3240 agtctccacc ccattgacgt caatgggagt ttgttttggc accaaaatca acgggacttt    3300
ccaaaatgtc gtaataaccc cgccccgttg acgcaaatgg gcggtaggcg tgtacggtgg    3360
gaggtctata taagcagagc tcgtttagtg aaccgtcaga tcactagaag cttaattgtg    3420
agcgctcaca attgtgagac tgctgccgca gtcagtaatt gtgagcgctc acaattgacc    3480
tggagctgca ggagttggta attgtgagcg ctcacaattg catgcgatat atatctaggc    3540
caccatggcc cagtccaagc acggcctgac caaggagatg accatgaagt accgcatgga    3600
gggctgcgtg gacggccaca gttcgtgat caccggcgag ggcatcggct ccccttcaa    3660 gggcaagcag gtaagtatca aggttacaag acaggtttaa ggacatgcag ccttctgtga    3720
tttgaggaca tataagccgg acttgtcgag acagagaaga ctcttgcgtt tctgataggc    3780
acctattggt cttactgaca tccactttgc ctttctctcc acaggccatc aacctgtgcg    3840
tggtggaggg cggcccctg cccttcgccg aggacatctt gtccgccgcc ttcatgtacg    3900
gcaaccgcgt gttcaccgag tacccccagg acatcgtcga ctacttcaag aactcctgcc    3960
ccgccggcta cacctgggac cgctccttcc tgttcgagga cggcgccgtg tgcatctgca    4020
acgccgacat caccgtgagc gtggaggaga actgcatgta ccacgagtcc aagttctacg    4080
gcgtgaactt ccccgccgac ggccccgtga tgaagaagat gaccgacaac tgggagccct    4140
cctgcgagaa gatcatcccc gtgcccaagc agggcatctt gaaggcgac gtgagcatgt    4200 acctgctgct gaaggacggt ggccgcttgc gctgccagtt cgacaccgtg tacaaggcca    4260
agtccgtgcc ccgcaagatg cccgactgga cttcatcca gcacaagctg acccgcgagg    4320
accgcagcga cgccaagaac cagaagtggc acctgaccga gcacgccatc gcctccggct    4380
ccgccttgcc caagcttccg cggagccatg gcttcccgcc ggcggtggcg cgcaggatg    4440
```

```
atggcacgct gcccatgtct tgtgcccagg agagcgggat ggaccgtcac cctgcagcct    4500
gtgcttctgc taggatcaat gtgtagcggc cgcaagcttg gcgtaatcat ggtcatagct    4560
gtttcctgtg tgaaattgtt atccgctcac aattccacac aacatacgag ccggaagcat    4620
aaagtgtaaa gcctggggtg cctaatgagt gagctaactc acattaattg cgttgcgctc    4680
actgcccgct ttccagtcgg gaaacctgtc gtgccagctg cattaatgaa tcggccaacg    4740
cgcggggaga ggcggtttgc gtattgggcg ctcttccgct tcctcgctca ctgactcgct    4800
gcgctcggtc gttcggctgc ggcgagcggt atcagctcac tcaaaggcgg taatacggtt    4860
atccacagaa tcaggggata acgcaggaaa gaacatgttt attgcagctt ataatggtta    4920
caaataaagc aatagcatca caaatttcac aaataaagca ttttttttcac tgcattctag    4980 ttgtggtttg tccaaactca tcaatgtatc ttatcatgtc tgctcgaagc ggccgcggta    5040
cctcactgcc cgctttccag tcgggaaacc tgtcgtgcca gctgcattaa tgaatcggcc    5100
aacgcgcggg gagaggcggt ttgcgtattg ggcgccaggg tggttttttct tttcaccagt    5160 gagacgggca acagctgatt gcccttcacc gcctggccct gagagagttg cagcaagcgg    5220
tccacgctgg tttgccccag caggcgaaaa tcctgtttga tggtggttaa cggcgggata    5280
taacatgagc tgtcttcggt atcgtcgtat cccactaccg agatatccgc accaacgcgc    5340
agcccggact cggtaatggc gcgcattgcg cccagcgcca tctgatcgtt ggcaaccagc    5400
atcgcagtgg gaacgatgcc ctcattcagc atttgcatgg tttgttgaaa accggacatg    5460
gcactccagt cgccttcccg ttccgctatc ggctgaattt gattgcgagt gagatattta    5520
tgccagccag ccagacgcag acgcgccgag acagaactta atgggcccgc taacagcgcg    5580
atttgctggt gacccaatgc gaccagatgc tccacgccca gtcgcgtacc gtcttcatgg    5640
gagaaaataa tactgttgat gggtgtctgg tcagagacat caagaaataa cgccggaaca    5700
ttagtgcagg cagcttccac agcaatggca tcctggtcat ccagcggata gttaatgatc    5760
agcccactga cgcgttgcgc gagaagattg tgcaccgccg ctttacaggc ttcgacgccg    5820
cttcgttcta ccatcgacac caccacgctg gcacccagtt gatcggcgcg agatttaatc    5880
gccgcgacaa tttgcgacgg cgcgtgcagg gccagactgg aggtggcaac gccaatcagc    5940
aacgactgtt tgcccgccag ttgttgtgcc acgcggttgg gaatgtaatt cagctccgcc    6000
atcgccgctt ccacttttttc ccgcgttttc gcagaaacgt ggctggcctg gttcaccacg    6060
cgggaaacgg tctgataaga gacaccggca tactctgcga catcgtataa cgttactggt    6120
ttcaccatgg tggctcgagc tatagtgagt cgtattaagt actctagcct taagagctgt    6180
aattgaactg ggagtggaca cctgtggaga aaaggcaaa gtggatgtca gtaagaccaa    6240
taggtgccta tcagaaacgc aagagtcttc tctgtctcga caagcccagt ttctattggt    6300
ctccttaaac ctgtcttgta accttgatac ttacctgccc agtgcctcac gaccaacttc    6360
tgcagcttaa gttcgagact gttgtgtcag aagcactgac tgcgttagca atttaactgt    6420
gataaactac cgcaataaag cttctagtga tctgacggtt cactaaacga gctctgctta    6480
tatagacctc ccaccgtaca cgcctaccgc ccatttgcgt caacggggcg ggttattac    6540 gacattttgg aaagtcccgt tgattttggt gccaaaacaa actcccattg acgtcaatgg    6600
ggtggagact tggaaatccc cgtgagtcaa accgctatcc acgccattg gtgtactgcc    6660 aaaaccgcat caccatggta atagcgatga ctaatacgta gatgtactgc caagtaggaa    6720
agtcccgtaa ggtcatgtac tgggcataat gccaggcggg ccatttaccg tcattgacgt    6780
```

```
caatagggggg cggacttggc atatgataca cttgatgtac tgccaagtgg gcagtttacc    6840
gtaaatactc cacccattga cgtcaatgga aagtccctat tggcgttact atgggaacat    6900
acgtcattat tgacgtcaat gggcgggggt cgttgggcgg tcagccaggc gggccattta    6960
ccgtaagtta tgtaacgcgg aactccatat atgggctatg aactaatgac cccgtaattg    7020
attactatta ataactagtc aataatcaat gccaacatgg cggtcatatt ggacatgagc    7080
caatataaat gtacatatta tgatatagat acaacgtatg caatggccaa tagccaatat    7140
tgatttatgc tatataacca atgaataata tggctaatgg ccaatattga acatgtgagc    7200
aaaaggccag caaaaggcca ggaaccgtaa aaaggccgcg ttgctggcgt ttttccatag    7260
gctccgcccc cctgacgagc atcacaaaaa tcgacgctca agtcagaggt ggcgaaaccc    7320
gacaggacta taaagatacc aggcgtttcc ccctggaagc tccctcgtgc gctctcctgt    7380
tccgaccctg ccgcttaccg gatacctgtc cgcctttctc ccttcgggaa gcgtggcgct    7440
ttctcatagc tcacgctgta ggtatctcag ttcggtgtag gtcgttcgct ccaagctggg    7500
ctgtgtgcac gaaccccccg ttcagcccga ccgctgcgcc ttatccggta actatcgtct    7560
tgagtccaac ccggtaagac acgacttatc gccactggca gcagccactg gtaacaggat    7620
tagcagagcg aggtatgtag gcggtgctac agagttcttg aagtggtggc ctaactacgg    7680
ctacactaga agaacagtat ttggtatctg cgctctgctg aagccagtta ccttcggaaa    7740
aagagttggt agctcttgat ccggcaaaca aaccaccgct ggtagcggtg gtttttttgt    7800
ttgcaagcag cagattacgc gcagaaaaaa aggatctcaa gaagatcctt tgatcttttc    7860
tacgggtct gacgctcagt ggaacgaaaa ctcacgttaa gggattttgg tcatgagatt     7920
atcaaaaagg atcttcacct agatcctttt aaattaaaaa tgaagtttta aatcaatcta    7980
aagtatatat gagtaaactt ggtctgacag ttaccaatgc ttaatcagtg aggcacctat    8040
ctcagcgatc tgtctatttc gttcatccat agttgcctga ctccccgtcg tgtagataac    8100
tacgatacgg gagggcttac catctggccc cagtgctgca atgataccgc gagacccacg    8160
ctcaccggct ccagatttat cagcaataaa ccagccagcc ggaagggccg agcgcagaag    8220
tggtcctgca actttatccg cctccatcca gtctattaat tgttgccggg aagctagagt    8280
aagtagttcg ccagttaata gtttgcgcaa cgttgttgcc attgctacag gcatcgtggt    8340
gtcacgctcg tcgtttggta tggcttcatt cagctccggt tcccaacgat caaggcgagt    8400
tacatgatcc cccatgttgt gcaaaaaagc ggttagctcc ttcggtcctc cgatcgttgt    8460
cagaagtaag ttggccgcag tgttatcact catggttatg gcagcactgc ataattctct    8520
tactgtcatg ccatccgtaa gatgcttttc tgtgactggt gagtactcaa ccaagtcatt    8580
ctgagaatag tgtatgcggc gaccgagttg ctcttgcccg gcgtcaatac gggataatac    8640
cgcgccacat agcagaactt taaaagtgct catcattgga aaacgttctt cggggcgaaa    8700
actctcaagg atcttaccgc tgttgagatc cagttcgatg taacccactc gtgcacccaa    8760
ctgatcttca gcatctttta ctttcaccag cgtttctggg tgagcaaaaa caggaaggca    8820
aaatgccgca aaaaagggaa taagggcgac acggaaatgt tgaatactca tactcttcct    8880
ttttcaatat tattgaagca tttatcaggg ttattgtctc atgagcggat acatatttga    8940
atgtatttag aaaaataaac aaataggggt tccgcgcaca tttccccgaa aagtgccacc    9000
tgacgtctaa gaaaccatta ttatcatgac attaacctat aaaaataggc gtatcacgag    9060
gccctttcgt c                                                          9071
```

<210> SEQ ID NO 5
<211> LENGTH: 6773
<212> TYPE: DNA
<213> ORGANISM: Artificial Sequence
<220> FEATURE:
<223> OTHER INFORMATION: Synthesized

<400> SEQUENCE: 5

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcaggcgcg | tcagcgggtg | 120 |
| ttggcgggtg | tcgggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | cagatcttca | atattggcca | 420 |
| ttagccatat | tattcattgg | ttatatagca | taaatcaata | ttggctattg | gccattgcat | 480 |
| acgttgtatc | tatatcataa | tatgtacatt | tatattggct | catgtccaat | atgaccgcca | 540 |
| tgttggcatt | gattattgac | tagttattaa | tagtaatcaa | ttacggggtc | attagttcat | 600 |
| agcccatata | tggagttccg | cgttacataa | cttacggtaa | atggcccgcc | tggctgaccg | 660 |
| cccaacgacc | cccgcccatt | gacgtcaata | atgacgtatg | ttcccatagt | aacgccaata | 720 |
| gggactttcc | attgacgtca | atgggtggag | tatttacggt | aaactgccca | cttggcagta | 780 |
| catcaagtgt | atcatatgcc | aagtccgccc | cctattgacg | tcaatgacgg | taaatggccc | 840 |
| gcctggcatt | atgcccagta | catgacctta | cgggactttc | ctacttggca | gtacatctac | 900 |
| gtattagtca | tcgctattac | catgatgatg | cggttttggc | agtacaccaa | tgggcgtgga | 960 |
| tagcggtttg | actcacgggg | atttccaagt | ctccacccca | ttgacgtcaa | tgggagtttg | 1020 |
| ttttggcacc | aaaatcaacg | ggactttcca | aatgtcgta | ataaccccgc | ccgttgacg | 1080 |
| caaatgggcg | gtaggcgtgt | acggtgggag | gtctatataa | gcagagctcg | tttagtgaac | 1140 |
| cgtcagatca | ctagaagctt | aattgtgagc | gctcacaatt | gtgagactgc | tgccgcagtc | 1200 |
| agtaattgtg | agcgctcaca | attgacctgg | agctgcagga | gttggtaatt | gtgagcgctc | 1260 |
| acaattctcg | agatatatat | ctaggccacc | atggcaccga | agaagaagcg | caaggtgcat | 1320 |
| atgaatacaa | aatataataa | ggtaagtatc | aaggttacaa | gacaggttta | aggcgccaat | 1380 |
| agaagcttgg | cttgtcgaga | cagagaagac | tcttgcgttt | ctgataggca | cctattggtc | 1440 |
| ttactgacat | ccactttgcc | tttctctcca | caggagttct | tactctactt | agcagggttt | 1500 |
| gtagacggtg | acggttccat | ctttgcctgt | atccatccta | gtcaagcgta | taagttcaag | 1560 |
| caccggctga | ctctccattt | cacggtcact | cagaagacac | agcgccgttg | gttcctcgac | 1620 |
| aagctggtgg | acgagatcgg | tgtgggttac | gtgcaggacg | tgggcagcgt | ctcccagtac | 1680 |
| cggctgtccc | agatcaagcc | tttgcataat | ttttaacac | aactacaacc | ttttctaaaa | 1740 |
| ctaaaacaaa | acaagcaaa | tttagtttta | aaaattattg | aacaacttcc | gtcagcaaaa | 1800 |
| gaatccccgg | acaaattctt | agaagtttgt | acatgggtgg | atcaaattgc | agctctgaat | 1860 |
| gattcgaaga | cgcgtaaaac | aacttctgaa | accgttcgtg | ctgtgctaga | cagtttacca | 1920 |
| ggatccgtgg | gaggtctatc | gccatctcag | gcatccagcg | ccgcatcctc | ggcttcctca | 1980 |
| agcccgggtt | cagggatctc | cgaagcactc | agagctggag | caggttccgg | cactggatac | 2040 |
| aacaaggaat | tcctgctcta | cctggcgggc | ttcgtcgacg | gggacggctc | catctctgcc | 2100 |

```
actatcgctc cggctcagta tggtaagttc aagcactatc tggggctccg gttctatgtc   2160
agtcagaaga cacagcgccg ttggttcctc gacaagctgg tggacgagat cggtgtgggt   2220
tacgtgagtg accagggcag cgtctccagg tactgtctgt cccagatcaa gcctctgcac   2280
aacttcctga cccagctcca gcccttcctg aagctcaagc agaagcaggc caacctcgtg   2340
ctgaagatca tcgagcagct gccctccgcc aaggaatccc cggacaagtt cctggaggtg   2400
tgcacctggg tggaccagat cgccgctctg aacgactcca agacccgcaa gaccacttcc   2460
gaaaccgtcc gcgccgttct agacagtctc tccgagaaga agaagtcgtc cccctaaggt   2520
accattcgag cagacatgat aagatacatt gatgagtttg acaaaccac aactagaatg    2580
cagtgaaaaa aatgctttat ttgtgaaatt tgtgatgcta ttgctttatt tgtaaccatt   2640
ataagctgca ataaactagt tcaatattgg ccattagcca tattattcat tggttatata   2700
gcataaatca atattggcta ttggccattg catacgttgt atctatatca taatatgtac   2760
atttatattg gctcatgtcc aatatgaccg ccatgttggc attgattatt gactagttat   2820
taatagtaat caattacggg gtcattagtt catagcccat atatggagtt ccgcgttaca   2880
taacttacgg taaatggccc gcctggctga ccgcccaacg accccgccc attgacgtca    2940
ataatgacgt atgttcccat agtaacgcca atagggactt tccattgacg tcaatgggtg   3000
gagtatttac ggtaaactgc ccacttggca gtacatcaag tgtatcatat gccaagtccg   3060
cccctattg acgtcaatga cggtaaatgg cccgcctggc attatgccca gtacatgacc    3120
ttacgggact ttcctacttg gcagtacatc tacgtattag tcatcgctat taccatgatg   3180
atgcggtttt ggcagtacac caatgggcgt ggatagcggt ttgactcacg ggatttcca    3240
agtctccacc ccattgacgt caatgggagt ttgttttggc accaaaatca acgggacttt   3300
ccaaaatgtc gtaataaccc cgccccgttg acgcaaatgg gcggtaggcg tgtacggtgg   3360
gaggtctata taagcagagc tcgtttagtg aaccgtcaga tcactagaag cttaattgtg   3420
agcgctcaca attgtgagac tgctgccgca gtcagtaatt gtgagcgctc acaattgacc   3480
tggagctgca ggagttggta attgtgagcg ctcacaattg catgcgatat atatctaggc   3540
caccatggcc cagtccaagc acggcctgac caaggagatg accatgaagt accgcatgga   3600
gggctgcgtg gacggccaca gttcgtgat caccggcgag ggcatcggct accccttcaa    3660
gggcaagcag gtaagtatca aggttacaag acaggtttaa ggacatgcag ccttctgtga   3720
tttgaggaca tataagccgg acttgtcgag acagagaaga ctcttgcgtt tctgataggc   3780
acctattggt cttactgaca tccactttgc ctttctctcc acaggccatc aacctgtgcg   3840
tggtggaggg cggcccctg ccctcgccg aggacatctt gtccgccgcc ttcatgtacg     3900
gcaaccgcgt gttcaccgag taccccagg acatcgtcga ctacttcaag aactcctgcc    3960
ccgccggcta cacctgggac cgctccttcc tgttcgagga cggcgccgtg tgcatctgca   4020
acgccgacat caccgtgagc gtggaggaga ctgcatgta ccacgagtcc aagttctacg    4080
gcgtgaactt ccccgccgac ggccccgtga tgaagaagat gaccgacaac tgggagccct   4140
cctgcgagaa gatcatcccc gtgcccaagc agggcatctt gaagggcgac gtgagcatgt   4200
acctgctgct gaaggacggt ggccgcttgc gctgccagtt cgacaccgtg tacaaggcca   4260
agtccgtgcc ccgcaagatg cccgactggc acttcatcca gcacaagctg accgcgagg    4320
accgcagcga cgccaagaac cagaagtggc acctgaccga gcacgccatc gcctccggct   4380
ccgccttgcc caagcttccg cggagccatg gcttcccgcc ggcggtggcg cgcaggatg    4440
atggcacgct gcccatgtct tgtgcccagg agagcgggat ggaccgtcac cctgcagcct   4500
```

```
gtgcttctgc taggatcaat gtgtagcggc cgcaagcttg gcgtaatcat ggtcatagct    4560
gtttcctgtg tgaaattgtt atccgctcac aattccacac aacatacgag ccggaagcat    4620
aaagtgtaaa gcctggggtg cctaatgagt gagctaactc acattaattg cgttgcgctc    4680
actgcccgct ttccagtcgg gaaacctgtc gtgccagctg cattaatgaa tcggccaacg    4740
cgcggggaga ggcggtttgc gtattgggcg ctcttccgct tcctcgctca ctgactcgct    4800
gcgctcggtc gttcggctgc ggcgagcggt atcagctcac tcaaaggcgg taatacggtt    4860
atccacagaa tcaggggata acgcaggaaa gaacatgtga gcaaaaggcc agcaaaaggc    4920
caggaaccgt aaaaaggccg cgttgctggc gtttttccat aggctccgcc ccctgacga    4980 gcatcacaaa aatcgacgct caagtcagag gtggcgaaac ccgacaggac tataaagata    5040
ccaggcgttt cccctggaa gctccctcgt gcgctctcct gttccgaccc tgccgcttac    5100
cggatacctg tccgcctttc tcccttcggg aagcgtggcg ctttctcata gctcacgctg    5160
taggtatctc agttcggtgt aggtcgttcg ctccaagctg ggctgtgtgc acgaaccccc    5220
cgttcagccc gaccgctgcg ccttatccgg taactatcgt cttgagtcca acccggtaag    5280
acacgactta tcgccactgg cagcagccac tggtaacagg attagcagag cgaggtatgt    5340
aggcggtgct acagagttct tgaagtggtg gcctaactac ggctacacta agaacagt    5400 atttggtatc tgcgctctgc tgaagccagt taccttcgga aaagagttg gtagctcttg    5460 atccggcaaa caaccaccg ctggtagcgg tggtttttt gtttgcaagc agcagattac    5520
gcgcagaaaa aaggatctc aagaagatcc tttgatcttt tctacggggt ctgacgctca    5580
gtggaacgaa aactcacgtt aagggatttt ggtcatgaga ttatcaaaaa ggatcttcac    5640
ctagatcctt ttaaattaaa aatgaagttt taaatcaatc taaagtatat atgagtaaac    5700
ttggtctgac agttaccaat gcttaatcag tgaggcacct atctcagcga tctgtctatt    5760
tcgttcatcc atagttgcct gactccccgt cgtgtagata actacgatac gggagggctt    5820
accatctggc cccagtgctg caatgatacc gcgagaccca cgctcaccgg ctccagattt    5880
atcagcaata accagccag ccggaagggc cgagcgcaga agtggtcctg caactttatc    5940
cgcctccatc cagtctatta attgttgccg ggaagctaga gtaagtagtt cgccagttaa    6000
tagtttcgcc aacgttgttg ccattgctac aggcatcgtg gtgtcacgct cgtcgtttgg    6060
tatggcttca ttcagctccg gttcccaacg atcaaggcga gttacatgat cccccatgtt    6120
gtgcaaaaaa gcggttagct ccttcggtcc tccgatcgtt gtcagaagta agttggccgc    6180
agtgttatca ctcatggtta tggcagcact gcataattct cttactgtca tgccatccgt    6240
aagatgcttt tctgtgactg gtgagtactc aaccaagtca ttctgagaat agtgtatgcg    6300
gcgaccgagt tgctcttgcc cggcgtcaat acgggataat accgcgccac atagcagaac    6360
tttaaaagtg ctcatcattg gaaaacgttc ttcggggcga aaactctcaa ggatcttacc    6420
gctgttgaga tccagttcga tgtaacccac tcgtgcaccc aactgatctt cagcatcttt    6480
tactttcacc agcgtttctg ggtgagcaaa aacaggaagg caaaatgccg caaaaaggg    6540 aataagggcg acacggaaat gttgaatact catactcttc cttttcaat attattgaag    6600 catttatcag ggttattgtc tcatgagcgg atacatattt gaatgtattt agaaaataa    6660 acaaataggg gttccgcgca catttccccg aaaagtgcca cctgacgtct aagaaccat    6720 tattatcatg acattaacct ataaaaatag gcgtatcacg aggccctttc gtc           6773
```

<210> SEQ ID NO 6

<211> LENGTH: 5741
<212> TYPE: DNA
<213> ORGANISM: Artificial Sequence
<220> FEATURE:
<223> OTHER INFORMATION: Synthesized

<400> SEQUENCE: 6

| | | | | | |
|---|---|---|---|---|---|
| cagcagctgg | cgtaatagcg | aagaggcccg | caccgatcgc | ccttcccaac | agttgcgcag | 60 |
| cctgaatggc | gaatggaatt | ccagacgatt | gagcgtcaaa | atgtaggtat | ttccatgagc | 120 |
| gtttttcctg | ttgcaatggc | tggcggtaat | attgttctgg | atattaccag | caaggccgat | 180 |
| agtttgagtt | cttctactca | ggcaagtgat | gttattacta | atcaaagaag | tattgcgaca | 240 |
| acggttaatt | tgcgtgatgg | acagactctt | ttactcggtg | gcctcactga | ttataaaaac | 300 |
| acttctcagg | attctggcgt | accgttcctg | tctaaaatcc | ctttaatcgg | cctcctgttt | 360 |
| agctcccgct | ctgattctaa | cgaggaaagc | acgttatacg | tgctcgtcaa | agcaaccata | 420 |
| gtacgcgccc | tgtagcggcg | cattaagcgc | ggcgggtgtg | gtggttacgc | gcagcgtgac | 480 |
| cgctacactt | gccagcgccc | tagcgcccgc | tcctttcgct | ttcttccctt | cctttctcgc | 540 |
| cacgttcgcc | ggctttcccc | gtcaagctct | aaatcggggg | ctccctttag | ggttccgatt | 600 |
| tagtgcttta | cggcacctcg | accccaaaaa | acttgattag | ggtgatggtt | cacgtagtgg | 660 |
| gccatcgccc | tgatagacgg | tttttcgccc | tttgacgttg | gagtccacgt | tctttaatag | 720 |
| tggactcttg | ttccaaactg | gaacaacact | caacccatc | tcggtctatt | cttttgattt | 780 |
| ataaggggatt | tgccgatttt | cggcctattg | gttaaaaaat | gagctgattt | aacaaaaatt | 840 |
| taacgcgaat | tttaacaaaa | tattaacgtt | acaatttaa | atatttgctt | atacaatctt | 900 |
| cctgtttttg | ggcttttct | gattatcaac | cggggtacat | atgattgaca | tgctagtttt | 960 |
| acgattaccg | ttcatcgccc | tgcgcgctcg | ctcgctcact | gaggccgccc | gggcaaagcc | 1020 |
| cgggcgtcgg | gcgacctttg | gtcgcccggc | ctcagtgagc | gagcgagcgc | gcagagaggg | 1080 |
| agtggaattc | acgcgtgggc | cccagaagcc | tggtggttgt | ttgtccttct | caggggaaaa | 1140 |
| gtgaggcggc | cccttggagg | aaggggccgg | gcagaatgat | ctaatcggat | tccaagcagc | 1200 |
| tcaggggatt | gtcttttct | agcaccttct | tgccactcct | aagcgtcctc | cgtgaccccg | 1260 |
| gctgggattt | agcctggtgc | tgtgtcagcc | ccgggctccc | aggggcttcc | cagtggtccc | 1320 |
| caggaacccct | cgacagggcc | agggcgtctc | tctcgtccag | caagggcagg | gacgggccac | 1380 |
| aggccaaggg | caagcttggc | tagccaccat | ggcaccgaag | aagaagcgca | aggtgcatat | 1440 |
| gaatacaaaa | tataataagg | taagtatcaa | ggttacaaga | caggtttaag | gcgccaatag | 1500 |
| aaacgggtgt | ggtacgcagc | cactggcttg | tcgagacaga | gaagactctt | gcgtttctga | 1560 |
| taggcaccta | ttggtcttac | tgacatccac | tttgcctttc | tctccacagg | agttcttact | 1620 |
| ctacttagca | gggtttgtag | acggtgacgg | ttccatctat | gcccgtatct | ttaagggtca | 1680 |
| acattggaag | ttcaagcact | atattcgttt | gaccttctgt | gtgcggcaga | agacacagcg | 1740 |
| ccgttggttc | ctcgacaagc | tggtggacga | gatcggtgtg | ggttacgtga | ctgactctgg | 1800 |
| cagcgttttcc | gcttactatc | tgtccgagat | caagcctttg | cataattttt | taacacaact | 1860 |
| acaacctttt | ctaaaactaa | aacaaaaaca | agcaaattta | gttttaaaaa | ttattgaaca | 1920 |
| acttccgtca | gcaaaagaat | ccccggacaa | attcttagaa | gtttgtacat | gggtggatca | 1980 |
| aattgcagct | ctgaatgatt | cgaagacgcg | taaaacaact | tctgaaaccg | ttcgtgctgt | 2040 |
| gctagacagt | ttaccaggat | ccgtgggagg | tctatcgcca | tctcaggcat | ccagcgccgc | 2100 |
| atcctcggct | tcctcaagcc | cgggttcagg | gatctccgaa | gcactcagag | ctggagcagg | 2160 |

```
ttccggcact ggatacaaca aggaattcct gctctacctg gcgggcttcg tcgacgggga    2220
cggctccatc tgggcctcga tcattcctga gcaaggttat aagttcaagc acaggctgcg    2280
tctctctttc actgtcgctc agaagacaca gcgccgttgg ttcctcgaca agctggtgga    2340
cgagatcggt gtgggttacg tggttgacca gggcagcgtc tccgagtaca ggctgtccga    2400
gatcaagcct ctgcacaact tcctgaccca gctccagccc ttcctgaagc tcaagcagaa    2460
gcaggccaac ctcgtgctga agatcatcga gcagctgccc tccgccaagg aatccccgga    2520
caagttcctg gaggtgtgca cctgggtgga ccagatcgcc gctctgaacg actccaagac    2580
ccgcaagacc acttccgaaa ccgtccgcgc cgttctagac agtctctccg agaagaagaa    2640
gtcgtccccc taagcggccg cgactctaga tcataatcag ccataccaca tttgtagagg    2700
ttttacttgc tttaaaaaac ctcccacacc tccccctgaa cctgaaacat aaaatgaatg    2760
caattgttgt tgttaacttg tttattgcag cttataatgg ttacaaataa agcaatagca    2820
tcacaaattt cacaaataaa gcatttttt cactgcattc tagttgtggt ttgtccaaac    2880
tcatcaatgt atcttaaggc gggaattgat ctaggaaccc ctagtgatgg agttggccac    2940
tccctctctg cgcgctcgct cgctcactga ggccgcccgg gcaaagcccg ggcgtcgggc    3000
gacctttggt cgcccggcct cagtgagcga gcgagcgcgc agagagggag tggccaaccc    3060
cccccccccc ccccggcga ttctcttgtt tgctccagac tctcaggcaa tgacctgata    3120
gcctttgtag agacctctca aaaatagcta ccctctccgg catgaattta tcagctagaa    3180
cggttgaata tcatattgat ggtgatttga ctgtctccgg cctttctcac ccgtttgaat    3240
ctttacctac acattactca ggcattgcat ttaaaatata tgagggttct aaaaatttt    3300 atccttgcgt tgaaataaag gcttctcccg caaaagtatt acagggtcat aatgtttttg    3360
gtacaaccga tttagcttta tgctctgagg ctttattgct taattttgct aattctttgc    3420
cttgcctgta tgatttattg gatgttggaa ttcctgatgc ggtattttct ccttacgcat    3480
ctgtgcggta tttcacaccg catatggtgc actctcagta caatctgctc tgatgccgca    3540
tagttaagcc agccccgaca cccgccaaca cccgctgacg cgccctgacg gcttgtctg     3600 ctcccggcat ccgcttacag acaagctgtg accgtctccg ggagctgcat gtgtcagagg    3660
ttttcaccgt catcaccgaa acgcgcgaga cgaaagggcc tcgtgatacg cctatttta    3720 taggttaatg tcatgataat aatggtttct tagacgtcag gtggcacttt tcggggaaat    3780
gtgcgcggaa cccctatttg tttatttttc taaatacatt caaatatgta tccgctcatg    3840
agacaataac cctgataaat gcttcaataa tattgaaaaa ggaagagtat gagtattcaa    3900
catttccgtg tcgcccttat ccctttttt gcggcatttt gccttcctgt ttttgctcac    3960
ccagaaacgc tggtgaaagt aaaagatgct gaagatcagt tgggtgcacg agtgggttac    4020
atcgaactgg atctcaacag cggtaagatc cttgagagtt ttcgccccga agaacgtttt    4080
ccaatgatga gcacttttaa agttctgcta tgtggcgcgg tattatcccg tattgacgcc    4140
gggcaagagc aactcggtcg ccgcatacac tattctcaga atgacttggt tgagtactca    4200
ccagtcacag aaaagcatct tacggatggc atgacagtaa gagaattatg cagtgctgcc    4260
ataaccatga gtgataacac tgcggccaac ttacttctga caacgatcgg aggaccgaag    4320
gagctaaccg cttttttgca acatggggg gatcatgtaa ctcgccttga tcgttgggaa    4380
ccggagctga atgaagccat accaaacgac gagcgtgaca ccacgatgcc tgtagcaatg    4440
gcaacaacgt tgcgcaaact attaactggc gaactactta ctctagcttc ccggcaacaa    4500
```

| | |
|---|---|
| ttaatagact ggatggaggc ggataaagtt gcaggaccac ttctgcgctc ggcccttccg | 4560 |
| gctggctggt ttattgctga taaatctgga gccggtgagc gtgggtctcg cggtatcatt | 4620 |
| gcagcactgg ggccagatgg taagccctcc cgtatcgtag ttatctacac gacggggagt | 4680 |
| caggcaacta tggatgaacg aaatagacag atcgctgaga taggtgcctc actgattaag | 4740 |
| cattggtaac tgtcagacca agtttactca tatatacttt agattgattt aaaacttcat | 4800 |
| ttttaattta aaaggatcta ggtgaagatc cttttttgata atctcatgac caaaatccct | 4860 |
| taacgtgagt tttcgttcca ctgagcgtca gaccccgtag aaaagatcaa aggatcttct | 4920 |
| tgagatcctt ttttttctgcg cgtaatctgc tgcttgcaaa caaaaaaacc accgctacca | 4980 |
| gcggtggttt gtttgccgga tcaagagcta ccaactcttt ttccgaaggt aactggcttc | 5040 |
| agcagagcgc agataccaaa tactgtcctt ctagtgtagc cgtagttagg ccaccacttc | 5100 |
| aagaactctg tagcaccgcc tacatacctc gctctgctaa tcctgttacc agtggctgct | 5160 |
| gccagtggcg ataagtcgtg tcttaccggg ttggactcaa gacgatagtt accggataag | 5220 |
| gcgcagcggt cgggctgaac ggggggttcg tgcacacagc ccagcttgga gcgaacgacc | 5280 |
| tacaccgaac tgagatacct acagcgtgag ctatgagaaa gcgccacgct tcccgaaggg | 5340 |
| agaaaggcgg acaggtatcc ggtaagcggc agggtcggaa caggagagcg cacgagggag | 5400 |
| cttccagggg gaaacgcctg gtatctttat agtcctgtcg ggtttcgcca cctctgactt | 5460 |
| gagcgtcgat ttttgtgatg ctcgtcaggg gggcggagcc tatggaaaaa cgccagcaac | 5520 |
| gcggcctttt tacggttcct ggccttttgc tggccttttg ctcacatgtt ctttcctgcg | 5580 |
| ttatcccctg attctgtgga taaccgtatt accgcctttg agtgagctga taccgctcgc | 5640 |
| cgcagccgaa cgaccgagcg cagcgagtca gtgagcgagg aagcggaaga gcgcccaata | 5700 |
| cgcaaaccgc ctctccccgc gcgttggccg attcattaat g | 5741 |

<210> SEQ ID NO 7
<211> LENGTH: 6335
<212> TYPE: DNA
<213> ORGANISM: Artificial Sequence
<220> FEATURE:
<223> OTHER INFORMATION: Synthesized

<400> SEQUENCE: 7

| | |
|---|---|
| cagcagctgg cgtaatagcg aagaggcccg caccgatcgc ccttcccaac agttgcgcag | 60 |
| cctgaatggc gaatggaatt ccagacgatt gagcgtcaaa atgtaggtat ttccatgagc | 120 |
| gttttttcctg ttgcaatggc tggcggtaat attgttctgg atattaccag caaggccgat | 180 |
| agtttgagtt cttctactca ggcaagtgat gttattacta atcaaagaag tattgcgaca | 240 |
| acggttaatt tgcgtgatgg acagactctt ttactcggtg gcctcactga ttataaaaac | 300 |
| acttctcagg attctggcgt accgttcctg tctaaaatcc ctttaatcgg cctcctgttt | 360 |
| agctcccgct ctgattctaa cgaggaaagc acgttatacg tgctcgtcaa agcaaccata | 420 |
| gtacgcgccc tgtagcggcg cattaagcgc ggcgggtgtg gtggttacgc gcagcgtgac | 480 |
| cgctacactt gccagcgccc tagcgcccgc tcctttcgct ttcttccctt cctttctcgc | 540 |
| cacgttcgcc ggctttcccc gtcaagctct aaatcggggg ctcccttag ggttccgatt | 600 |
| tagtgcttta cggcacctcg accccaaaaa acttgattag ggtgatggtt cacgtagtgg | 660 |
| gccatcgccc tgatagacgg ttttcgccc tttgacgttg gagtccacgt tctttaatag | 720 |
| tggactcttg ttccaaactg gaacaacact caacccatc tcggtctatt cttttgattt | 780 |
| ataagggatt ttgccgattt cggcctattg gttaaaaaat gagctgattt aacaaaaatt | 840 |

```
taacgcgaat tttaacaaaa tattaacgtt tacaatttaa atatttgctt atacaatctt      900
cctgttttg gggcttttct gattatcaac cggggtacat atgattgaca tgctagtttt      960
acgattaccg ttcatcgccc tgcgcgctcg ctcgctcact gaggccgccc gggcaaagcc     1020
cgggcgtcgg gcgacctttg gtcgcccggc ctcagtgagc gagcgagcgc gcagagaggg     1080
agtggaattc acgcgtggat cttaatagta atcaattacg ggtcattag ttcatagccc      1140
atatatggag ttccgcgtta cataacttac ggtaaatggc ccgcctggct gaccgcccaa     1200
cgacccccgc ccattgacgt caataatgac gtatgttccc atagtaacgc caatagggac     1260
tttccattga cgtcaatggg tggagtattt acggtaaact gcccacttgg cagtacatca     1320
agtgtatcat atgccaagtc cgccccctat tgacgtcaat gacggtaaat ggcccgcctg     1380
gcattatgcc cagtacatga ccttacggga ctttcctact ggcagtaca tctacgtatt      1440
agtcatcgct attaccatgg tgatgcggtt ttggcagtac accaatgggc gtggatagcg     1500
gtttgactca cggggatttc caagtctcca ccccattgac gtcaatggga gtttgttttg     1560
gcaccaaaat caacgggact ttccaaaatg tcgtaataac cccgccccgt tgacgcaaat     1620
gggcggtagg cgtgtacggt gggaggtcta tataagcaga gctcgtttag tgaaccgtca     1680
gatcactaga agctttattg cggtagttta tcacagttaa attgctaacg cagtcagtgc     1740
ttctgacaca acagtctcga acttaagctg cagaagttgg tcgtgaggca ctgggcaggt     1800
gtccactccc agttcaatta cagctcttaa ggctagagta cttaatacga ctcactatag     1860
gctagccacc atggcaccga agaagaagcg caaggtgcat atgaatacaa aatataataa     1920
agagttctta ctctacttag cagggtaagc gcccctaaaa tccctttggg cacaatgtgt     1980
cctgagggga gaggcagcga cctgtagatg ggacacgggt gtggtacgca gccactgggg     2040
gcactaaccc tcaggtttgg ggcttctgaa tgtgagtatc gccatgtaag cccagtattt     2100
ggccaatctc agaaagctcc tggtccctgg agggatggag agagaaaaac aaacagctcc     2160
tggagcaggg agagtgctgg cctcttgctc tccggctccc tctgttgccc tctggtttct     2220
ccccaggttt gtagacggtg acggttccat ctatgcccgt atctttaagg gtcaacattg     2280
gaagttcaag cactatattc gtttgacctt ctgtgtgcgg cagaagacac agcgccgttg     2340
gttcctcgac aagctggtgg acgagatcgg tgtgggttac gtgactgact ctggcagcgt     2400
ttccgcttac tatctgtccg agatcaagcc tttgcataat tttttaacac aactacaacc     2460
ttttctaaaa ctaaaacaaa aacaagcaaa tttagtttta aaattattg aacaacttcc      2520
gtcagcaaaa gaatccccgg acaaattctt agaagtttgt acatgggtgg atcaaattgc     2580
agctctgaat gattcgaaga cgcgtaaaac aacttctgaa accgttcgtg ctgtgctaga     2640
cagtttacca ggatccgtgg gaggtctatc gccatctcag gcatccagcg ccgcatcctc     2700
ggcttcctca agcccgggtt cagggatctc cgaagcactc agagctggag caggttccgg     2760
cactggatac aacaaggaat tcctgctcta cctggcgggc ttcgtcgacg ggacggctc      2820
catctgggcc tcgatcattc ctgagcaagg ttataagttc aagcacaggc tgcgtctctc     2880
tttcactgtc gctcagaaga cacagcgccg ttggttcctc gacaagctgg tggacgagat     2940
cggtgtgggt tacgtggttg accagggcag cgtctccgag tacaggctgt ccgagatcaa     3000
gcctctgcac aacttcctga cccagctcca gccttcctg aagctcaagc agaagcaggc      3060
caacctcgtg ctgaagatca tcgagcagct gccctccgcc aaggaatccc cggacaagtt     3120
cctggaggtg tgcacctggg tggaccagat cgccgctctg aacgactcca agacccgcaa     3180
```

-continued

```
gaccacttcc gaaaccgtcc gcgccgttct agacagtctc tccgagaaga agaagtcgtc      3240
cccctaagcg gccgcgactc tagatcataa tcagccatac cacatttgta gaggttttac      3300
ttgctttaaa aaacctccca cacctccccc tgaacctgaa acataaaatg aatgcaattg      3360
ttgttgttaa cttgtttatt gcagcttata atggttacaa ataaagcaat agcatcacaa      3420
atttcacaaa taaagcattt ttttcactgc attctagttg tggtttgtcc aaactcatca      3480
atgtatctta aggcgggaat tgatctagga accctagtg atggagttgg ccactccctc       3540
tctgcgcgct cgctcgctca ctgaggccgc ccgggcaaag cccgggcgtc gggcgacctt      3600
tggtcgcccg gcctcagtga gcgagcgagc gcgcagagag ggagtggcca accccccccc      3660 ccccccccg gcgattctct tgtttgctcc agactctcag gcaatgacct gatagccttt       3720
gtagagacct ctcaaaaata gctaccctct ccggcatgaa tttatcagct agaacggttg      3780
aatatcatat tgatggtgat ttgactgtct ccggcctttc tcacccgttt gaatctttac      3840
ctacacatta tcaggcatt gcatttaaaa tatatgaggg ttctaaaaat ttttatcctt       3900
gcgttgaaat aaaggcttct cccgcaaaag tattacaggg tcataatgtt tttggtacaa      3960
ccgatttagc tttatgctct gaggctttat tgcttaattt tgctaattct ttgccttgcc      4020
tgtatgattt attggatgtt ggaattcctg atgcggtatt ttctccttac gcatctgtgc      4080
ggtatttcac accgcatatg gtgcactctc agtacaatct gctctgatgc cgcatagtta      4140
agccagcccc gacacccgcc aacacccgct gacgcgccct gacgggcttg tctgctcccg      4200
gcatccgctt acagacaagc tgtgaccgtc tccgggagct gcatgtgtca gaggttttca      4260
ccgtcatcac cgaaacgcgc gagacgaaag gcctcgtga tacgcctatt tttataggtt       4320
aatgtcatga taataatggt ttcttagacg tcaggtggca cttttcgggg aaatgtgcgc      4380 ggaacccta tttgtttatt tttctaaata cattcaaata tgtatccgct catgagacaa       4440
taaccctgat aaatgcttca ataatattga aaaggaaga gtatgagtat tcaacatttc       4500
cgtgtcgccc ttattccctt ttttgcggca ttttgcctc ctgttttgc tcacccagaa        4560 acgctggtga agtaaaaga tgctgaagat cagttgggtg cacgagtggg ttacatcgaa       4620
ctggatctca acagcggtaa gatccttgag agttttcgcc ccgaagaacg ttttccaatg      4680
atgagcactt ttaaagttct gctatgtggc gcggtattat cccgtattga cgccgggcaa     4740
gagcaactcg gtcgccgcat acactattct cagaatgact tggttgagta ctcaccagtc     4800
acagaaaagc atcttacgga tggcatgaca gtaagagaat tatgcagtgc tgccataacc     4860
atgagtgata acactgcggc caacttactt ctgacaacga tcggaggacc gaaggagcta    4920
accgcttttt tgcacaacat gggggatcat gtaactcgcc ttgatcgttg ggaaccggag    4980
ctgaatgaag ccataccaaa cgacgagcgt gacaccacga tgcctgtagc aatggcaaca    5040
acgttgcgca aactattaac tggcgaacta cttactctag cttcccggca acaattaata    5100
gactggatgg aggcggataa agttgcagga ccacttctgc gctcggccct tccggctggc    5160
tggtttattg ctgataaatc tggagccggt gagcgtgggt ctcgcggtat cattgcagca    5220
ctggggccag atggtaagcc ctcccgtatc gtagttatct acacgacggg gagtcaggca    5280
actatggatg aacgaaatag acagatcgct gagataggtg cctcactgat taagcattgg    5340
taactgtcag accaagttta ctcatatata ctttagattg atttaaaact tcattttaa    5400 tttaaaagga tctaggtgaa gatccttttt gataatctca tgaccaaaat cccttaacgt    5460
gagttttcgt tccactgagc gtcagacccc gtagaaaaga tcaaaggatc ttcttgagat    5520 ccttttttc tgcgcgtaat ctgctgcttg caaacaaaaa aaccaccgct accagcggtg    5580
```

```
gtttgtttgc cggatcaaga gctaccaact cttttttccga aggtaactgg cttcagcaga    5640
gcgcagatac caaatactgt ccttctagtg tagccgtagt taggccacca cttcaagaac    5700
tctgtagcac cgcctacata cctcgctctg ctaatcctgt taccagtggc tgctgccagt    5760
ggcgataagt cgtgtcttac cgggttggac tcaagacgat agttaccgga taaggcgcag    5820
cggtcgggct gaacggggggg ttcgtgcaca gcccagct tggagcgaac gacctacacc      5880
gaactgagat acctacagcg tgagctatga aaagcgcca cgcttcccga agggagaaag    5940
gcggacaggt atccggtaag cggcagggtc ggaacaggag agcgcacgag ggagcttcca    6000
gggggaaacg cctggtatct ttatagtcct gtcgggtttc gccacctctg acttgagcgt    6060
cgatttttgt gatgctcgtc agggggggcgg agcctatgga aaaacgccag caacgcggcc    6120 ttttttacggtt tcctggcctt ttgctggcct tttgctcaca tgttctttcc tgcgttatcc    6180
cctgattctg tggataaccg tattaccgcc tttgagtgag ctgataccgc tcgccgcagc    6240
cgaacgaccg agcgcagcga gtcagtgagc gaggaagcgg aagagcgccc aatacgcaaa    6300
ccgcctctcc ccgcgcgttg gccgattcat taatg                                 6335

<210> SEQ ID NO 8
<211> LENGTH: 6421
<212> TYPE: DNA
<213> ORGANISM: Artificial Sequence
<220> FEATURE:
<223> OTHER INFORMATION: Synthesized

<400> SEQUENCE: 8
cagcagctgg cgtaatagcg aagaggcccg caccgatcgc ccttcccaac agttgcgcag      60
cctgaatggc gaatggaatt ccagacgatt gagcgtcaaa atgtaggtat ttccatgagc     120 gttttttcctg ttgcaatggc tggcggtaat attgttctgg atattaccag caaggccgat    180
agtttgagtt cttctactca ggcaagtgat gttattacta atcaaagaag tattgcgaca    240
acggttaatt tgcgtgatgg acagactctt ttactcggtg gcctcactga ttataaaaac    300
acttctcagg attctggcgt accgttcctg tctaaaatcc ctttaatcgg cctcctgttt    360
agctcccgct ctgattctaa cgaggaaagc acgttatacg tgctcgtcaa gcaaccata    420 gtacgcgccc tgtagcggcg cattaagcgc ggcgggtgtg gtggttacgc gcagcgtgac    480
cgctacactt gccagcgccc tagcgcccgc tcctttcgct ttcttccctt cctttctcgc    540
cacgttcgcc ggctttcccc gtcaagctct aaatcggggg ctccctttag ggttccgatt    600
tagtgcttta cggcacctcg accccaaaaa acttgattag ggtgatggtt cacgtagtgg    660
gccatcgccc tgatagacgg ttttttcgccc tttgacgttg gagtccacgt tctttaatag    720
tggactcttg ttccaaactg gaacaacact caacccctatc tcggtctatt cttttgattt    780
ataagggatt ttgccgattt cggcctattg gttaaaaaat gagctgattt aacaaaaatt    840
taacgcgaat tttaacaaaa tattaacgtt tacaatttaa atatttgctt atacaatcttt    900 cctgtttttg ggcttttctt gattatcaac cggggtacat atgattgaca tgctagtttt    960
acgattaccg ttcatcgccc tgcgcgctcg ctcgctcact gaggccgccc gggcaaagcc   1020
cgggcgtcgg gcgacctttg gtcgcccggc ctcagtgagc gagcgagcgc gcagagaggg   1080
agtggaattc acgcgtggat cttaatagta atcaattacg gggtcattag ttcatagccc   1140
atatatggag ttccgcgtta cataacttac ggtaaatggc ccgcctggct gaccgcccaa   1200 cgaccccccgc ccattgacgt caataatgac gtatgttccc atagtaacgc caatagggac   1260
```

-continued

```
tttccattga cgtcaatggg tggagtattt acggtaaact gcccacttgg cagtacatca    1320
agtgtatcat atgccaagtc cgccccctat tgacgtcaat gacggtaaat ggcccgcctg    1380
gcattatgcc cagtacatga ccttacggga ctttcctact tggcagtaca tctacgtatt    1440
agtcatcgct attaccatgg tgatgcggtt ttggcagtac accaatgggc gtggatagcg    1500
gtttgactca cggggatttc caagtctcca ccccattgac gtcaatggga gtttgttttg    1560
gcaccaaaat caacgggact ttccaaaatg tcgtaataac cccgcccgt tgacgcaaat    1620 gggcggtagg cgtgtacggt gggaggtcta taagcaga gctcgtttag tgaaccgtca    1680
gatcactaga agctttattg cggtagttta tcacagttaa attgctaacg cagtcagtgc    1740
ttctgacaca acagtctcga acttaagctg cagaagttgg tcgtgaggca ctgggcaggt    1800
gtccactccc agttcaatta cagctcttaa ggctagagta cttaatacga ctcactatag    1860
gctagccacc atggcaccga agaagaagcg caaggtgcat atgaatacaa aatataataa    1920
agagttctta ctctacttag cagggtattt gcttcttcct taaatcctgg tgttgatgca    1980
atgtactgca aacaatggcc tgagtgtgca aagaaaatgt ctgctaactg catatgcttg    2040
ctgtgcttac tgaggatgaa gcatgaaaat agaaaattat acaggaaaga tccacttgtg    2100
tgggttgatt gctactgctt cgattgcttt agaatgtggt ttggacgggt gtggtacgca    2160
gccactactt gatctttgtg aaggaacctt acttctgtgg tgtgacataa ttggacaaac    2220
tacctacaga gatttaaagc tctaaggtaa atataaaatt tttaagtgta taatgtgtta    2280
aactactgat tctaattgtt tgtgtatttt aggtttgtag acggtgacgg ttccatctat    2340
gcccgtatct ttaagggtca acattggaag ttcaagcact atattcgttt gaccttctgt    2400
gtgcggcaga agacacagcg ccgttggttc ctcgacaagc tggtggacga atcggtgtg    2460 ggttacgtga ctgactctgg cagcgtttcc gcttactatc tgtccagat caagcctttg    2520 cataattttt taacacaact acaaccttt ctaaaactaa aacaaaaaca agcaaattta    2580
gttttaaaaa ttattgaaca acttccgtca gcaaagaat ccccggacaa attcttagaa    2640
gtttgtacat gggtggatca aattgcagct ctgaatgatt cgaagacgcg taaaacaact    2700
tctgaaaccg ttcgtgctgt gctagacagt ttaccaggat ccgtgggagg tctatcgcca    2760
tctcaggcat ccagcgccgc atcctcggct tcctcaagcc cgggttcagg gatctccgaa    2820
gcactcagag ctggagcagg ttccggcact ggatacaaca aggaattcct gctctacctg    2880
gcgggcttcg tcgacgggga cggctccatc tgggcctcga tcattcctga gcaaggttat    2940
aagttcaagc acaggctgcg tctctctttc actgtcgctc agaagacaca gcgccgttgg    3000
ttcctcgaca agctggtgga cgagatcggt gtgggttacg tggttgacca gggcagcgtc    3060
tccgagtaca ggctgtccga gatcaagcct ctgcacaact tcctgaccca gctccagccc    3120
ttcctgaagc tcaagcagaa gcaggccaac ctcgtgctga gatcatcga gcagctgccc    3180 tccgccaagg aatccccgga caagttcctg gaggtgtgca cctgggtgga ccagatcgcc    3240
gctctgaacg actccaagac ccgcaagacc acttccgaaa ccgtccgcgc cgttctagac    3300
agtctctccg agaagaagaa gtcgtcccc taagcggccg cgactctaga tcataatcag    3360
ccataccaca tttgtagagg ttttacttgc tttaaaaaac ctcccacacc tccccctgaa    3420
cctgaaacat aaaatgaatg caattgttgt tgttaacttg tttattgcag cttataatgg    3480
ttacaaataa agcaatagca tcacaaattt cacaaataaa gcatttttt cactgcattc    3540 tagttgtggt ttgtccaaac tcatcaatgt atcttaaggc gggaattgat ctaggaaccc    3600
ctagtgatgg agttggccac tccctctctg cgcgctcgct cgctcactga ggccgcccgg    3660
```

-continued

```
gcaaagcccg ggcgtcgggc gacctttggt cgcccggcct cagtgagcga gcgagcgcgc    3720
agagagggag tggccaaccc ccccccccc ccccggcga ttctcttgtt tgctccagac      3780
tctcaggcaa tgacctgata gcctttgtag agacctctca aaaatagcta ccctctccgg    3840
catgaattta tcagctagaa cggttgaata tcatattgat ggtgatttga ctgtctccgg    3900
cctttctcac ccgtttgaat ctttacctac acattactca ggcattgcat ttaaaatata    3960
tgagggttct aaaaattttt atccttgcgt tgaaataaag gcttctcccg caaaagtatt    4020
acagggtcat aatgttttttg gtacaaccga tttagcttta tgctctgagg ctttattgct   4080
taattttgct aattctttgc cttgcctgta tgatttattg gatgttggaa ttcctgatgc    4140
ggtattttct ccttacgcat ctgtgcggta tttcacaccg catatggtgc actctcagta    4200
caatctgctc tgatgccgca tagttaagcc agccccgaca cccgccaaca cccgctgacg    4260
cgccctgacg ggcttgtctg ctcccggcat ccgcttacag acaagctgtg accgtctccg    4320
ggagctgcat gtgtcagagg ttttcaccgt catcaccgaa acgcgcgaga cgaaagggcc    4380
tcgtgatacg cctatttta taggttaatg tcatgataat aatggtttct tagacgtcag     4440
gtggcacttt tcggggaaat gtgcgcggaa cccctatttg tttatttttc taaatacatt    4500
caaatatgta tccgctcatg agacaataac cctgataaat gcttcaataa tattgaaaaa    4560
ggaagagtat gagtattcaa catttccgtg tcgcccttat tccctttttt gcggcatttt    4620
gccttcctgt ttttgctcac ccagaaacgc tggtgaaagt aaaagatgct gaagatcagt    4680
tgggtgcacg agtgggttac atcgaactgg atctcaacag cggtaagatc cttgagagtt    4740
ttcgccccga agaacgtttt ccaatgatga gcacttttaa agttctgcta tgtggcgcgg    4800
tattatcccg tattgacgcc gggcaagagc aactcggtcg ccgcatacac tattctcaga    4860
atgacttggt tgagtactca ccagtcacag aaaagcatct tacggatggc atgacagtaa    4920
gagaattatg cagtgctgcc ataaccatga gtgataacac tgcggccaac ttacttctga    4980
caacgatcgg aggaccgaag gagctaaccg cttttttgca aacatgggg gatcatgtaa     5040 ctcgccttga tcgttgggaa ccggagctga atgaagccat accaaacgac gagcgtgaca    5100
ccacgatgcc tgtagcaatg gcaacaacgt tgcgcaaact attaactggc gaactactta    5160
ctctagcttc ccggcaacaa ttaatagact ggatggaggc ggataaagtt gcaggaccac    5220
ttctgcgctc ggcccttccg gctggctggt ttattgctga taaatctgga gccggtgagc    5280
gtgggtctcg cggtatcatt gcagcactgg ggccagatgg taagccctcc cgtatcgtag    5340
ttatctacac gacggggagt caggcaacta tggatgaacg aaatagacag atcgctgaga    5400
taggtgcctc actgattaag cattggtaac tgtcagacca agtttactca tatatacttt    5460
agattgattt aaaacttcat ttttaattta aaaggatcta ggtgaagatc cttttttgata   5520 atctcatgac caaaatccct taacgtgagt tttcgttcca ctgagcgtca gaccccgtag    5580
aaaagatcaa aggatcttct tgagatcctt ttttctgcg cgtaatctgc tgcttgcaaa     5640
caaaaaaacc accgctacca gcggtggttt gtttgccgga tcaagagcta ccaactcttt    5700
ttccgaaggt aactggcttc agcagagcgc agataccaaa tactgtcctt ctagtgtagc    5760
cgtagttagg ccaccacttc aagaactctg tagcaccgcc tacatacctc gctctgctaa    5820
tcctgttacc agtggctgct gccagtggcg ataagtcgtg tcttaccggg ttggactcaa    5880
gacgatagtt accggataag gcgcagcggt cgggctgaac ggggggttcg tgcacacagc    5940
ccagcttgga gcgaacgacc tacaccgaac tgagatacct acagcgtgag ctatgagaaa    6000
```

```
gcgccacgct tcccgaaggg agaaaggcgg acaggtatcc ggtaagcggc agggtcggaa      6060
caggagagcg cacgagggag cttccagggg gaaacgcctg gtatctttat agtcctgtcg      6120
ggtttcgcca cctctgactt gagcgtcgat ttttgtgatg ctcgtcaggg gggcggagcc      6180
tatggaaaaa cgccagcaac gcggcctttt tacggttcct ggccttttgc tggccttttg      6240
ctcacatgtt ctttcctgcg ttatcccctg attctgtgga taaccgtatt accgcctttg      6300
agtgagctga taccgctcgc cgcagccgaa cgaccgagcg cagcgagtca gtgagcgagg      6360
aagcggaaga gcgcccaata cgcaaaccgc ctctccccgc gcgttggccg attcattaat      6420
g                                                                     6421

<210> SEQ ID NO 9
<211> LENGTH: 8620
<212> TYPE: DNA
<213> ORGANISM: Artificial Sequence
<220> FEATURE:
<223> OTHER INFORMATION: Synthesized

<400> SEQUENCE: 9
cagcagctgg cgtaatagcg aagaggcccg caccgatcgc ccttcccaac agttgcgcag        60
cctgaatggc gaatggaatt ccagacgatt gagcgtcaaa atgtaggtat ttccatgagc       120 gttttcctg ttgcaatggc tggcggtaat attgttctgg atattaccag caaggccgat        180
agtttgagtt cttctactca ggcaagtgat gttattacta tcaaagaag tattgcgaca        240 acggttaatt tgcgtgatgg acagactctt ttactcggtg gcctcactga ttataaaaac       300
acttctcagg attctggcgt accgttcctg tctaaaatcc ctttaatcgg cctcctgttt       360
agctcccgct ctgattctaa cgaggaaagc acgttatacg tgctcgtcaa agcaaccata       420
gtacgcgccc tgtagcggcg cattaagcgc ggcgggtgtg gtggttacgc gcagcgtgac       480
cgctacactt gccagcgccc tagcgcccgc tcctttcgct ttcttccctt cctttctcgc       540
cacgttcgcc ggctttcccc gtcaagctct aaatcggggg ctccctttag ggttccgatt       600
tagtgcttta cggcacctcg accccaaaaa acttgattag ggtgatggtt cacgtagtgg       660
gccatcgccc tgatagacgg ttttcgccc tttgacgttg gagtccacgt tctttaatag       720
tggactcttg ttccaaactg gaacaacact caaccctatc tcggtctatt cttttgattt       780
ataagggatt ttgccgattt cggcctattg gttaaaaaat gagctgattt aacaaaaatt       840
taacgcgaat tttaacaaaa tattaacgtt tacaatttaa atatttgctt atacaatctt       900 cctgttttg gggcttttct gattatcaac cggggtacat atgattgaca tgctagtttt       960
acgattaccg ttcatcgccc tgcgcgctcg ctcgctcact gaggccgccc gggcaaagcc      1020
cgggcgtcgg cgaccttttg gtcgcccggc ctcagtgagc gagcgagcgc gcagagaggg      1080
agtggaattc acgcgtgggc ccctcaatat tggccattag ccatattatt cattggttat      1140
atagcataaa tcaatattgg ctattggcca ttgcatacgt tgtatctata tcataatatg      1200
tacatttata ttggctcatg tccaatatga ccgccatgtt ggcattgatt attgactagt      1260
tattaatagt aatcaattac ggggtcatta gttcatagcc catatatgga gttccgcgtt      1320
acataactta cggtaaatgg cccgcctggc tgaccgccca acgacccccg cccattgacg      1380
tcaataatga cgtatgttcc catagtaacg ccaatagggg ctttccattg acgtcaatgg      1440
gtggagtatt tacggtaaac tgcccacttg gcagtacatc aagtgtatca tatgccaagt      1500
ccgcccccta ttgacgtcaa tgacggtaaa tggcccgcct ggcattatgc ccagtacatg      1560
accttacggg actttcctac ttggcagtac atctacgtat tagtcatcgc tattaccatg      1620
```

```
atgatgcggt tttggcagta caccaatggg cgtggatagc ggtttgactc acggggattt   1680
ccaagtctcc accccattga cgtcaatggg agtttgtttt ggcaccaaaa tcaacgggac   1740
tttccaaaat gtcgtaataa ccccgccccg ttgacgcaaa tgggcggtag gcgtgtacgg   1800
tgggaggtct atataagcag agctcgttta gtgaaccgtc agatcactag aagcttaatt   1860
gtgagcgctc acaattgtga gactgctgcc gcagtcagta attgtgagcg ctcacaattg   1920
acctggagct gcaggagttg gtaattgtga gcgctcacaa ttcgtgaggc actgggcagg   1980
ctagccacca tggcaccgaa gaagaagcgc aaggtgcata tgaatacaaa atataataag   2040
gtaagtatca aggttacaag acaggtttaa ggcgccaata gaaacgggtg tggtacgcag   2100
ccactggctt gtcgagacag agaagactct tgcgtttctg ataggcacct attggtctta   2160
ctgacatcca ctttgccttt ctctccacag gagttcttac tctacttagc agggtttgta   2220
gacggtgacg gttccatcta tgcccgtatc tttaagggtc aacattggaa gttcaagcac   2280
tatattcgtt tgaccttctg tgtgcggcag aagacacagc gccgttggtt cctcgacaag   2340
ctggtggacg agatcggtgt gggttacgtg actgactctg gcagcgtttc cgcttactat   2400
ctgtccgaga tcaagccttt gcataatttt ttaacacaac tacaaccttt tctaaaacta   2460
aaacaaaaac aagcaaattt agttttaaaa attattgaac aacttccgtc agcaaaagaa   2520
tccccggaca aattcttaga agtttgtaca tgggtggatc aaattgcagc tctgaatgat   2580
tcgaagacgc gtaaaacaac ttctgaaacc gttcgtgctg tgctagacag tttaccagga   2640
tccgtgggag gtctatcgcc atctcaggca tccagcgccg catcctcggc ttcctcaagc   2700
ccgggttcag ggatctccga agcactcaga gctggagcag gttccggcac tggatacaac   2760
aaggaattcc tgctctacct ggcgggcttc gtcgacgggg acggctccat ctgggcctcg   2820
atcattcctg agcaaggtta taagttcaag cacaggctgc gtctctcttt cactgtcgct   2880
cagaagacac agcgccgttg gttcctcgac aagctggtgg acgagatcgg tgtgggttac   2940
gtggttgacc agggcagcgt ctccgagtac aggctgtccg agatcaagcc tctgcacaac   3000
ttcctgaccc agctccagcc cttcctgaag ctcaagcaga agcaggccaa cctcgtgctg   3060
aagatcatcg agcagctgcc ctccgccaag gaatccccgg acaagttcct ggaggtgtgc   3120
acctgggtgg accagatcgc cgctctgaac gactccaaga cccgcaagac cacttccgaa   3180
accgtccgcg ccgttctaga cagtctctcc gagaagaaga agtcgtcccc ctaagcggcc   3240
gcgactctag atcataatca gccataccac atttgtagag gttttacttg ctttaaaaaa   3300
cctcccacac ctccccctga acctgaaaca taaaatgaat gcaattgttg ttgttaactt   3360
gtttattgca gcttataatg gttacaaata agcaatagc atcacaaatt tcacaaataa   3420
agcattttt tcactgcatt ctagttgtgg tttgtccaaa ctcatcaatg tatcttaagg   3480
cgggaattga tctaggaacc cctagtgatg gagttggcca ctccctctct gcgcgctcgc   3540
tcgctcactg aggccgcccg ggcaaagccc gggcgtcggg cgacctttgg tcgcccggcc   3600
tcagtgagcg agcgagcgcg cagagaggga gtggccaacc cccccccccc cccccggcg   3660
attctcttgt ttgctccaga ctctcaggca atgacctgat agcctttgta gagacctctc   3720
aaaaatagct accctctccg gcatgaattt atcagctaga acggttgaat atcatattga   3780
tggtgatttg actgtctccg gcctttctca cccgtttgaa tctttaccta cacattactc   3840
aggcattgca tttaaaatat atgagggttc taaaaatttt tatccttgcg ttgaaataaa   3900
ggcttctccc gcaaaagtat tacagggtca taatgttttt ggtacaaccg atttagcttt   3960
```

```
atgctctgag gctttattgc ttaattttgc taattctttg ccttgcctgt atgatttatt      4020
ggatgttgga attcctgatg cggtattttc tccttacgca tctgtgcggt atttcacacc      4080
gcatatggtg cactctcagt acaatctgct ctgatgccgc atagttaagc cagccccgac      4140
acccgccaac acccgctgac gcgccctgac gggcttgtct gctcccggca tccgcttaca      4200
gacaagctgt gaccgtctcc gggagctgca tgtgtcagag gttttcaccg tcatcaccga      4260
aacgcgcgag acgaaagggc ctcgtgatac gcctattttt ataggttaat gtcatgataa      4320
taatggtttc ttagacgtca ggtggcactt ttcggggaaa tgtgcgcgga accectattt      4380
gtttattttt ctaaatacat tcaaatatgt atccgctcat gagacaataa ccctgataaa      4440
tgcttcaata atattgaaaa aggaagagta tgagtattca acatttccgt gtcgccctta      4500
ttcccttttt tgcggcattt tgccttcctg tttttgctca cccagaaacg ctggtgaaag      4560
taaaagatgc tgaagatcag ttgggtgcac gagtgggtta catcgaactg gatctcaaca      4620
gcggtaagat ccttgagagt tttcgccccg aagaacgttt tccaatgatg agcactttta      4680
aagttctgct atgtggcgcg gtattatccc gtattgacgc cgggcaagag caactcggtc      4740
gccgcataca ctattctcag aatgacttgg ttgagtactc accagtcaca gaaaagcatc      4800
ttacggatgg catgacagta agagaattat gcagtgctgc cataaccatg agtgataaca      4860
ctgcggccaa cttacttctg acaacgatcg gaggaccgaa ggagctaacc gcttttttgc      4920
acaacatggg ggatcatgta actcgccttg atcgttggga accggagctg aatgaagcca      4980
taccaaacga cgagcgtgac accacgatgc ctgtagcaat ggcaacaacg ttgcgcaaac      5040
tattaactgg cgaactactt actctagctt cccggcaaca attaatagac tggatggagg      5100
cggataaagt tgcaggacca cttctgcgct cggcccttcc ggctggctgg tttattgctg      5160
ataaatctgg agccggtgag cgtgggtctc gcggtatcat tgcagcactg gggccagatg      5220
gtaagccctc ccgtatcgta gttatctaca cgacggggag tcaggcaact atggatgaac      5280
gaaatagaca gatcgctgag ataggtgcct cactgattaa gcattggtaa ctgtcagacc      5340
aagtttactc atatatactt tagattgatt taaaacttca tttttaattt aaaaggatct      5400
aggtgaagat cctttttgat aatctcatga ccaaaatccc ttaacgtgag ttttcgttcc      5460
actgagcgtc agaccccgta gaaaagatca aaggatcttc ttgagatcct ttttttctgc      5520
gcgtaatctg ctgcttgcaa acaaaaaaac caccgctacc agcggtggtt tgtttgccgg      5580
atcaagagct accaactctt tttccgaagg taactggctt cagcagagcg cagataccaa      5640
atactgtcct tctagtgtag ccgtagttag gccaccactt caagaactct gtagcaccgc      5700
ctacatacct cgctctgcta atcctgttac cagtggctgc tgccagtggc gataagtcgt      5760
gtcttaccgg gttggactca agacgatagt taccggataa ggcgcagcgg tcgggctgaa      5820
cggggggttc gtgcacacag cccagcttgg agcgaacgac ctacaccgaa ctgagatacc      5880
tacagcgtga gctatgagaa agcgccacgc ttcccgaagg gagaaaggcg gacaggtatc      5940
cggtaagcgg cagggtcgga acaggagagc gcacgaggga gcttccaggg ggaaacgcct      6000
ggtatcttta tagtcctgtc gggtttcgcc acctctgact tgagcgtcga tttttgtgat      6060
gctcgtcagg gggcggagc ctatggaaaa acgccagcaa cgcggccttt ttacggttcc      6120
tggccttttg ctggcctttt gctcacatgt ttattgcagc ttataatggt tacaaataaa      6180
gcaatagcat cacaaatttc acaaataaag catttttttc actgcattct agttgtggtt      6240
tgtccaaact catcaatgta tcttatcatg tctgctcgaa gcggccgcgg tacctcactg      6300
cccgctttcc agtcgggaaa cctgtcgtgc cagctgcatt aatgaatcgg ccaacgcgcg      6360
```

```
gggagaggcg gtttgcgtat tgggcgccag ggtggttttt cttttcacca gtgagacggg   6420
caacagctga ttgcccttca ccgcctggcc ctgagagagt tgcagcaagc ggtccacgct   6480
ggtttgcccc agcaggcgaa aatcctgttt gatggtggtt aacggcggga tataacatga   6540
gctgtcttcg gtatcgtcgt atcccactac cgagatatcc gcaccaacgc gcagcccgga   6600
ctcggtaatg gcgcgcattg cgcccagcgc catctgatcg ttggcaacca gcatcgcagt   6660
gggaacgatg ccctcattca gcatttgcat ggtttgttga aaaccggaca tggcactcca   6720
gtcgccttcc cgttccgcta tcggctgaat ttgattgcga gtgagatatt tatgccagcc   6780
agccagacgc agacgcgccg agacagaact taatgggccc gctaacagcg cgatttgctg   6840
gtgacccaat gcgaccagat gctccacgcc cagtcgcgta ccgtcttcat gggagaaaat   6900
aatactgttg atgggtgtct ggtcagagac atcaagaaat aacgccggaa cattagtgca   6960
ggcagcttcc acagcaatgg catcctggtc atccagcgga tagttaatga tcagcccact   7020
gacgcgttgc gcgagaagat tgtgcaccgc cgctttacag gcttcgacgc cgcttcgttc   7080
taccatcgac accaccacgc tggcacccag ttgatcggcg cgagatttaa tcgccgcgac   7140
aatttgcgac ggcgcgtgca gggccagact ggaggtggca acgccaatca gcaacgactg   7200
tttgcccgcc agttgttgtg ccacgcggtt gggaatgtaa ttcagctccg ccatcgccgc   7260
ttccactttt tcccgcgttt tcgcagaaac gtggctggcc tggttcacca cgcgggaaac   7320
ggtctgataa gagacaccgg catactctgc gacatcgtat aacgttactg gtttcaccat   7380
ggtggctcga gctatagtga gtcgtattaa gtactctagc cttaagagct gtaattgaac   7440
tgggagtgga cacctgtgga gagaaaggca agtggatgt cagtaagacc aataggtgcc   7500
tatcagaaac gcaagagtct tctctgtctc gacaagccca gttctattg gtctccttaa   7560 acctgtcttg taaccttgat acttacctgc ccagtgcctc acgaccaact tctgcagctt   7620
aagttcgaga ctgttgtgtc agaagcactg actgcgttag caatttaact gtgataaact   7680
accgcaataa agcttctagt gatctgacgg ttcactaaac gagctctgct tatatagacc   7740
tcccaccgta cacgcctacc gcccatttgc gtcaacgggg cggggttatt acgacatttt   7800
ggaaagtccc gttgattttg gtgccaaaac aaactcccat tgacgtcaat ggggtggaga   7860
cttggaaatc cccgtgagtc aaaccgctat ccacgcccat tggtgtactg ccaaaaccgc   7920
atcaccatgg taatagcgat gactaatacg tagatgtact gccaagtagg aaagtcccgt   7980
aaggtcatgt actgggcata atgccaggcg ggccatttac cgtcattgac gtcaataggg   8040
ggcggacttg gcatatgata cacttgatgt actgccaagt gggcagttta ccgtaaaatac   8100 tccacccatt gacgtcaatg gaaagtccct attggcgtta ctatgggaac atacgtcatt   8160
attgacgtca atgggcgggg gtcgttggc ggtcagccag gcgggccatt taccgtaagt   8220
tatgtaacgc ggaactccat atatgggcta tgaactaatg accccgtaat tgattactat   8280
taataactag tcaataatca atgccaacat ggcggtcata ttggacatga gccaatataa   8340
atgtacatat tatgatatag atacaacgta tgcaatggcc aatagccaat attgatttat   8400
gctatataac caatgaataa tatggctaat ggccaatatt gaacatgttc tttcctgcgt   8460
tatcccctga ttctgtggat aaccgtatta ccgcctttga gtgagctgat accgctcgcc   8520
gcagccgaac gaccgagcgc agcgagtcag tgagcgagga agcggaagag cgcccaatac   8580
gcaaaccgcc tctccccgcg cgttggccga ttcattaatg                         8620
```

<210> SEQ ID NO 10

<211> LENGTH: 6609
<212> TYPE: DNA
<213> ORGANISM: Artificial Sequence
<220> FEATURE:
<223> OTHER INFORMATION: Synthesized

<400> SEQUENCE: 10

| | | | | | |
|---|---|---|---|---|---|
| cagcagctgg | cgtaatagcg | aagaggcccg | caccgatcgc | ccttcccaac | agttgcgcag | 60 |
| cctgaatggc | gaatggaatt | ccagacgatt | gagcgtcaaa | atgtaggtat | ttccatgagc | 120 |
| gtttttcctg | ttgcaatggc | tggcggtaat | attgttctgg | atattaccag | caaggccgat | 180 |
| agtttgagtt | cttctactca | ggcaagtgat | gttattacta | atcaaagaag | tattgcgaca | 240 |
| acggttaatt | tgcgtgatgg | acagactctt | ttactcggtg | gcctcactga | ttataaaaac | 300 |
| acttctcagg | attctggcgt | accgttcctg | tctaaaatcc | ctttaatcgg | cctcctgttt | 360 |
| agctcccgct | ctgattctaa | cgaggaaagc | acgttatacg | tgctcgtcaa | agcaaccata | 420 |
| gtacgcgccc | tgtagcggcg | cattaagcgc | ggcgggtgtg | gtggttacgc | gcagcgtgac | 480 |
| cgctacactt | gccagcgccc | tagcgcccgc | tcctttcgct | ttcttccctt | cctttctcgc | 540 |
| cacgttcgcc | ggctttcccc | gtcaagctct | aaatcggggg | ctccctttag | ggttccgatt | 600 |
| tagtgcttta | cggcacctcg | accccaaaaa | acttgattag | ggtgatggtt | cacgtagtgg | 660 |
| gccatcgccc | tgatagacgg | tttttcgccc | tttgacgttg | gagtccacgt | tctttaatag | 720 |
| tggactcttg | ttccaaactg | gaacaacact | caacccatc | tcggtctatt | cttttgattt | 780 |
| ataagggatt | ttgccgattt | cggcctattg | gttaaaaaat | gagctgattt | aacaaaaatt | 840 |
| taacgcgaat | tttaacaaaa | tattaacgtt | tacaatttaa | atatttgctt | atacaatctt | 900 |
| cctgttttg | ggcttttct | gattatcaac | cggggtacat | atgattgaca | tgctagtttt | 960 |
| acgattaccg | ttcatcgccc | tgcgcgctcg | ctcgctcact | gaggccgccc | gggcaaagcc | 1020 |
| cgggcgtcgg | gcgacctttg | gtcgcccggc | ctcagtgagc | gagcgagcgc | gcagagaggg | 1080 |
| agtggaattc | acgcgtgggc | ccctcaatat | tggccattag | ccatattatt | cattggttat | 1140 |
| atagcataaa | tcaatattgg | ctattggcca | ttgcatacgt | tgtatctata | tcataatatg | 1200 |
| tacatttata | ttggctcatg | tccaatatga | ccgccatgtt | ggcattgatt | attgactagt | 1260 |
| tattaatagt | aatcaattac | ggggtcatta | gttcatagcc | catatatgga | gttccgcgtt | 1320 |
| acataactta | cggtaaatgg | cccgcctggc | tgaccgccca | acgacccccg | cccattgacg | 1380 |
| tcaataatga | cgtatgttcc | catagtaacg | ccaataggga | ctttccattg | acgtcaatgg | 1440 |
| gtggagtatt | tacggtaaac | tgcccacttg | gcagtacatc | aagtgtatca | tatgccaagt | 1500 |
| ccgcccccta | ttgacgtcaa | tgacggtaaa | tggcccgcct | ggcattatgc | ccagtacatg | 1560 |
| accttacggg | actttcctac | ttggcagtac | atctacgtat | tagtcatcgc | tattaccatg | 1620 |
| atgatgcggt | tttggcagta | caccaatggg | cgtggatagc | ggtttgactc | acggggattt | 1680 |
| ccaagtctcc | accccattga | cgtcaatggg | agtttgtttt | ggcaccaaaa | tcaacgggac | 1740 |
| tttccaaaat | gtcgtaataa | ccccgccccg | ttgacgcaaa | tgggcggtag | gcgtgtacgg | 1800 |
| tgggaggtct | atataagcag | agctcgttta | gtgaaccgtc | agatcactag | aagcttaatt | 1860 |
| gtgagcgctc | acaattgtga | gactgctgcc | gcagtcagta | attgtgagcg | ctcacaattg | 1920 |
| acctggagct | gcaggagttg | gtaattgtga | gcgctcacaa | ttcgtgaggc | actgggcagg | 1980 |
| ctagccacca | tggcaccgaa | gaagaagcgc | aaggtgcata | tgaatacaaa | atataataag | 2040 |
| gtaagtatca | aggttacaag | acaggtttaa | ggcgccaata | gaaacgggtg | tggtacgcag | 2100 |
| ccactggctt | gtcgagacag | agaagactct | tgcgtttctg | ataggcacct | attggtctta | 2160 |

```
ctgacatcca ctttgccttt ctctccacag gagttcttac tctacttagc agggtttgta    2220
gacggtgacg gttccatcta tgcccgtatc tttaagggtc aacattggaa gttcaagcac    2280
tatattcgtt tgaccttctg tgtgcggcag aagacacagc gccgttggtt cctcgacaag    2340
ctggtggacg agatcggtgt gggttacgtg actgactctg gcagcgtttc cgcttactat    2400
ctgtccgaga tcaagccttt gcataatttt ttaacacaac tacaacctttt tctaaaacta    2460 aaacaaaaac aagcaaattt agttttaaaa attattgaac aacttccgtc agcaaaagaa    2520
tccccggaca aattcttaga agtttgtaca tgggtggatc aaattgcagc tctgaatgat    2580
tcgaagacgc gtaaaacaac ttctgaaacc gttcgtgctg tgctagacag tttaccagga    2640
tccgtgggag gtctatcgcc atctcaggca tccagcgccg catcctcggc ttcctcaagc    2700
ccgggttcag ggatctccga agcactcaga gctggagcag gttccggcac tggatacaac    2760
aaggaattcc tgctctacct ggcgggcttc gtcgacgggg acggctccat ctgggcctcg    2820
atcattcctg agcaaggtta taagttcaag cacaggctgc gtctctcttt cactgtcgct    2880
cagaagacac agcgccgttg gttcctcgac aagctggtgg acgagatcgg tgtgggttac    2940
gtggttgacc agggcagcgt ctccgagtac aggctgtccg agatcaagcc tctgcacaac    3000
ttcctgaccc agctccagcc cttcctgaag ctcaagcaga agcaggccaa cctcgtgctg    3060
aagatcatcg agcagctgcc ctcgccaag gaatccccgg acaagttcct ggaggtgtgc    3120
acctgggtgg accagatcgc cgctctgaac gactccaaga cccgcaagac cacttccgaa    3180
accgtccgcg ccgttctaga cagtctctcc gagaagaaga agtcgtcccc ctaagcggcc    3240
gcgactctag atcataatca gccataccac atttgtagag gttttacttg ctttaaaaaa    3300
cctcccacac ctccccctga acctgaaaca taaaatgaat gcaattgttg ttgttaactt    3360
gtttattgca gcttataatg gttacaaata aagcaatagc atcacaaatt tcacaaataa    3420 agcattttt tcactgcatt ctagttgtgg tttgtccaaa ctcatcaatg tatcttaagg    3480
cgggaattga tctaggaacc cctagtgatg gagttggcca ctccctctct gcgcgctcgc    3540
tcgctcactg aggccgcccg ggcaaagccc gggcgtcggg cgacctttgg tcgcccggcc    3600
tcagtgagcg agcgagcgcg cagagaggga gtggccaacc cccccccccc ccccccggcg    3660
attctcttgt ttgctccaga ctctcaggca atgacctgat agcctttgta gagacctctc    3720
aaaaatagct accctctccg gcatgaattt atcagctaga acggttgaat atcatattga    3780
tggtgatttg actgtctccg gcctttctca cccgtttgaa tctttaccta cacattactc    3840
aggcattgca tttaaaatat atgagggttc taaaaatttt tatccttgcg ttgaaataaa    3900
ggcttctccc gcaaaagtat tacagggtca taatgttttt ggtacaaccg atttagcttt    3960
atgctctgag gctttattgc ttaattttgc taattctttg ccttgcctgt atgatttatt    4020
ggatgttgga attcctgatg cggtattttc tccttacgca tctgtgcggt atttcacacc    4080
gcatatggtg cactctcagt acaatctgct ctgatgccgc atagttaagc cagccccgac    4140
acccgccaac acccgctgac gcgccctgac gggcttgtct gctcccggca tccgcttaca    4200
gacaagctgt gaccgtctcc gggagctgca tgtgtcagag gttttcaccg tcatcaccga    4260
aacgcgcgag acgaaagggc ctcgtgatac gcctattttt ataggttaat gtcatgataa    4320
taatggtttc ttagacgtca ggtggcactt ttcggggaaa tgtgcgcgga acccctattt    4380 gtttatttt ctaaatacat tcaaatatgt atccgctcat gagacaataa ccctgataaa    4440
tgcttcaata atattgaaaa aggaagagta tgagtattca acatttccgt gtcgccctta    4500
```

```
ttcccttttt tgcggcattt tgccttcctg tttttgctca cccagaaacg ctggtgaaag    4560
taaaagatgc tgaagatcag ttgggtgcac gagtgggtta catcgaactg gatctcaaca    4620
gcggtaagat ccttgagagt tttcgccccg aagaacgttt tccaatgatg agcactttta    4680
aagttctgct atgtggcgcg gtattatccc gtattgacgc cgggcaagag caactcggtc    4740
gccgcataca ctattctcag aatgacttgg ttgagtactc accagtcaca gaaaagcatc    4800
ttacggatgg catgacagta agagaattat gcagtgctgc cataaccatg agtgataaca    4860
ctgcggccaa cttacttctg acaacgatcg gaggaccgaa ggagctaacc gcttttttgc    4920
acaacatggg ggatcatgta actcgccttg atcgttggga accggagctg aatgaagcca    4980
taccaaacga cgagcgtgac accacgatgc ctgtagcaat ggcaacaacg ttgcgcaaac    5040
tattaactgg cgaactactt actctagctt cccggcaaca attaatagac tggatggagg    5100
cggataaagt tgcaggacca cttctgcgct cggcccttcc ggctggctgg tttattgctg    5160
ataaatctgg agccggtgag cgtgggtctc gcggtatcat tgcagcactg gggccagatg    5220
gtaagccctc ccgtatcgta gttatctaca cgacggggag tcaggcaact atggatgaac    5280
gaaatagaca gatcgctgag ataggtgcct cactgattaa gcattggtaa ctgtcagacc    5340
aagtttactc atatatactt tagattgatt taaaacttca tttttaattt aaaaggatct    5400
aggtgaagat cctttttgat aatctcatga ccaaaatccc ttaacgtgag ttttcgttcc    5460
actgagcgtc agacccgta gaaaagatca aggatcttc ttgagatcct ttttttctgc    5520
gcgtaatctg ctgcttgcaa acaaaaaaac caccgctacc agcggtggtt tgtttgccgg    5580
atcaagagct accaactctt tttccgaagg taactggctt cagcagagcg cagataccaa    5640
atactgtcct tctagtgtag ccgtagttag gccaccactt caagaactct gtagcaccgc    5700
ctacatacct cgctctgcta atcctgttac cagtggctgc tgccagtggc gataagtcgt    5760
gtcttaccgg gttggactca agacgatagt taccggataa ggcgcagcgg tcgggctgaa    5820
cggggggttc gtgcacacag cccagcttgg agcgaacgac ctacaccgaa ctgagatacc    5880
tacagcgtga gctatgagaa agcgccacgc ttcccgaagg gagaaaggcg gacaggtatc    5940
cggtaagcgg cagggtcgga acaggagagc gcacgaggga gcttccaggg ggaaacgcct    6000
ggtatcttta tagtcctgtc gggtttcgcc acctctgact tgagcgtcga ttttttgtgat   6060
gctcgtcagg gggcggagc ctatggaaaa acgccagcaa cgcggccttt ttacggttcc    6120
tggccttttg ctggccttt gctcacatgt ttattgcagc ttataatggt tacaaataaa    6180
gcaatagcat cacaaatttc acaaataaag cattttttc actgcattct agttgtggtt    6240
tgtccaaact catcaatgta tcttatcatg tctgctcgaa gcggccgcgg taccaacatg    6300
gcggtcatat tggacatgag ccaatataaa tgtacatatt atgatataga tacaacgtat    6360
gcaatggcca atagccaata ttgatttatg ctatataacc aatgaataat atggctaatg    6420
gccaatattg aacatgttct ttcctgcgtt atcccctgat tctgtggata accgtattac    6480
cgcctttgag tgagctgata ccgctcgccg cagccgaacg accgagcgca gcgagtcagt    6540
gagcgaggaa gcggaagagc gcccaatacg caaaccgcct ctccccgcgc gttggccgat    6600
tcattaatg                                                            6609
```